US012600981B2

(12) United States Patent
Bean et al.

(10) Patent No.: US 12,600,981 B2
(45) Date of Patent: Apr. 14, 2026

(54) INSECT INHIBITORY PROTEINS

(71) Applicant: Monsanto Technology LLC, St. Louis, MO (US)

(72) Inventors: Gregory J. Bean, St. Louis, MO (US); David J. Bowen, Wildwood, MO (US); Catherine A. Chay, Ballwin, MO (US); Arlene R. Howe, Clarkson Valley, MO (US); Jason S. Milligan, Troy, IL (US); Yong Yin, Creve Coeur, MO (US)

(73) Assignee: Monsanto Technology LLC, St. Louis, MO (US)

( * ) Notice: Subject to any disclaimer, the term of this patent is extended or adjusted under 35 U.S.C. 154(b) by 184 days.

(21) Appl. No.: 18/426,976

(22) Filed: Jan. 30, 2024

(65) Prior Publication Data

US 2024/0287539 A1     Aug. 29, 2024

Related U.S. Application Data

(60) Division of application No. 17/485,853, filed on Sep. 27, 2021, now Pat. No. 11,920,145, which is a division of application No. 16/205,426, filed on Nov. 30, 2018, now Pat. No. 11,130,964, which is a continuation-in-part of application No. 14/945,140, filed on Nov. 18, 2015, now Pat. No. 10,662,439.

(60) Provisional application No. 62/082,504, filed on Nov. 20, 2014.

(51) Int. Cl.
*C12N 15/82* (2006.01)
*A01N 63/50* (2020.01)
*C07K 14/195* (2006.01)

(52) U.S. Cl.
CPC ......... *C12N 15/8286* (2013.01); *A01N 63/50* (2020.01); *C07K 14/195* (2013.01)

(58) Field of Classification Search
None
See application file for complete search history.

(56) References Cited

U.S. PATENT DOCUMENTS

| | | | |
|---|---|---|---|
| 5,880,275 | A | 3/1999 | Fischhoff et al. |
| 6,033,874 | A | 3/2000 | Baum et al. |
| 6,501,009 | B1 | 12/2002 | Romano |
| 6,692,705 | B2 | 2/2004 | Gupta et al. |
| 6,713,063 | B1 | 3/2004 | Malvar et al. |
| 7,064,249 | B2 | 6/2006 | Corbin et al. |
| 7,070,982 | B2 | 7/2006 | Malvar et al. |
| 7,510,878 | B2 | 3/2009 | Abad et al. |
| 7,772,465 | B2 | 8/2010 | Abad et al. |
| 7,812,129 | B1 | 10/2010 | Abad et al. |
| 8,461,415 | B2 | 6/2013 | Sampson et al. |
| 8,586,027 | B2 | 11/2013 | Escobar et al. |
| 8,609,936 | B2 | 12/2013 | Baum et al. |
| 11,130,964 | B2 | 9/2021 | Bean et al. |
| 11,193,138 | B2 | 12/2021 | Bean et al. |
| 11,198,888 | B2 | 12/2021 | Bean et al. |
| 11,920,145 | B2 | 3/2024 | Bean et al. |
| 2002/0199215 | A1 | 12/2002 | Boets et al. |
| 2005/0155103 | A1 | 7/2005 | Baum et al. |
| 2006/0112447 | A1 | 5/2006 | Bogdanova et al. |
| 2008/0172762 | A1 | 7/2008 | Cerf et al. |
| 2009/0313721 | A1 | 12/2009 | Abad et al. |
| 2010/0017914 | A1 | 1/2010 | Kruse |
| 2010/0077507 | A1 | 3/2010 | Abad et al. |
| 2010/0077508 | A1 | 3/2010 | Abad et al. |
| 2010/0192256 | A1 | 7/2010 | Abad et al. |
| 2010/0269221 | A1 | 10/2010 | Abad et al. |
| 2011/0030093 | A1 | 2/2011 | Dhugga |
| 2011/0030096 | A1 * | 2/2011 | Sampson ........... C12N 15/8286 514/4.5 |

(Continued)

FOREIGN PATENT DOCUMENTS

| | | |
|---|---|---|
| CL | 1395-2009 | 6/2009 |
| EP | 2079314 B1 | 3/2010 |

(Continued)

OTHER PUBLICATIONS

Argolo-Filho et al, Insects (2014) 5:62-91. (Year: 2024).*
Ruiu, Insects (2013) 4:476-492. (Year: 2013).*
De Oliveira et al (2004) 70:6657-6654. (Year: 2004).*
Yin, Y., "Novel MTX2-like Proteins for Insect Control", presentation at the 47th Annual Meeting of the Society for Invertebrate Pathology, Mainz, Germany, Aug. 2014 [PowerPoint presentation]. 14 slides.
Crickmore, N., et al., "Revision of the nomenclature for the Bacillus thuringiensis pesticidal crystal proteins." Microbiol Mol Biol Rev. 1998;62(3):807-13.

(Continued)

*Primary Examiner* — Mykola V. Kovalenko
(74) *Attorney, Agent, or Firm* — Dentons US LLP; David Lanzotti

(57) ABSTRACT

Insecticidal proteins exhibiting toxic activity against Coleopteran and Lepidopteran pest species are disclosed, and include, but are not limited to, TIC3668, TIC3669, TIC3670, TIC4076, TIC4078, TIC4260, TIC4346, TIC4826, TIC4861, TIC4862, TIC4863, TIC11239, TIC11243, TIC11256, TIC4544, TIC4545, TIC6871, TIC7429, TIC7497, TIC7511, TIC7513, TIC7518, TIC7524, TIC7526, TIC7528, TIC7535 and TIC-3668-type proteins. DNA molecules and constructs are provided which contain a polynucleotide sequence encoding one or more of the disclosed TIC3668-type proteins. Transgenic plants, plant cells, seed, and plant parts resistant to Lepidopteran and Coleopteran infestation are provided which contain polynucleotide sequences encoding the insecticidal proteins of the present invention. Methods for detecting the presence of the polynucleotides or the proteins of the present invention in a biological sample, and methods of controlling Coleopteran and Lepidopteran species pests using any of the TIC3668-type insecticidal proteins are also provided.

20 Claims, 3 Drawing Sheets

Specification includes a Sequence Listing.

(56)                    References Cited

U.S. PATENT DOCUMENTS

| | | | |
|---|---|---|---|
| 2011/0055968 | A1 | 3/2011 | Cerf et al. |
| 2011/0112013 | A1 | 5/2011 | Abad et al. |
| 2011/0154536 | A1 | 6/2011 | Abad et al. |
| 2011/0191900 | A1 | 8/2011 | Song et al. |
| 2012/0047606 | A1 | 2/2012 | Abad et al. |
| 2012/0117690 | A1 | 5/2012 | Cerf et al. |
| 2012/0167259 | A1 | 6/2012 | Liu et al. |
| 2012/0192310 | A1 | 7/2012 | Abad et al. |
| 2012/0233726 | A1 | 9/2012 | Abad et al. |
| 2013/0097735 | A1 | 4/2013 | Bowen et al. |
| 2013/0116170 | A1 | 5/2013 | Graser et al. |
| 2013/0269060 | A1 | 10/2013 | Baum et al. |
| 2014/0007292 | A1 | 1/2014 | Cerf et al. |
| 2014/0033361 | A1 | 1/2014 | Altier et al. |
| 2020/0157561 | A1 | 5/2020 | Bean et al. |
| 2020/0157562 | A1 | 5/2020 | Bean et al. |

FOREIGN PATENT DOCUMENTS

| | | | |
|---|---|---|---|
| EP | 1947184 | | 3/2011 |
| EP | 2455392 | A2 | 5/2012 |
| EP | 2671951 | A2 | 12/2013 |
| ES | 2203310 | | 6/2005 |
| RU | 251286 | C2 | 4/2014 |
| UA | 98770 | C2 | 6/2012 |
| WO | 1991016434 | | 10/1991 |
| WO | 2001019859 | | 3/2001 |
| WO | 2002014517 | | 2/2002 |
| WO | 2002022662 | | 3/2002 |
| WO | 2009088735 | | 7/2009 |
| WO | 2010099365 | | 9/2010 |
| WO | 2010142055 | | 12/2010 |
| WO | 2011014749 | | 2/2011 |
| WO | 2011041256 | | 4/2011 |
| WO | 2014008054 | | 1/2014 |
| WO | 2014045131 | | 3/2014 |
| WO | 2014102697 | | 7/2014 |

OTHER PUBLICATIONS

Palma, L., et al., "Bacillus thuringiensis toxins: an overview of their biocidal activity," Toxins (Basel), Dec. 11, 2014;6(12):3296-325.

Moar, W., et al., "The structure/function of new insecticidal proteins and regulatory challenges for commercialization". Journal of Invertebrate Pathology, 2017, 142:1-4.

Maagd, R., "Structure, diversity, and evolution of protein toxins from spore-forming entomopathogenic bacteria," Annu Rev Genet. 2003;37:409-33.

Ruiu, L., "Emerging entomoathogenic bacteria for insect pest management," Bulletin of Insectology 66 (2): 181-186, 2013.

Bacillus thuringiensis Toxin Nomenclature, Full list of delta-endotoxins. Retrieved from http://www.lifesci.sussex.ac.uk/home/Neil_Crickmore/Bt/toxins2.html on Nov. 28, 2018.

International Search Report and Written Opinion regarding International Application No. PCT/US2015/061371, dated Mar. 9, 2016.

Ruiu, "Brevibacillus laterosporus, a Pathogen of Invertebrates and a Broad-Spectrum Antimicrobial Species," Insects 4:476-492, 2013.

Office Action regarding Chilean Application No. 1298-2017, dated Jun. 19, 2018.

USPTO: Non-Final Office Action regarding U.S. Application No. 14/945, 140, dated Feb. 25, 2019.

Campbell et al., "Codon Usage in Higher Plants, Green Algae, and Cyanobacteria," Plant Physiol. 92:1-11, 1990.

De Oliveira et al., "Molecular Characterization of Brevibacillus laterosporus and Its Potential Use in Biological Control," Applied and Environmental Microbiology 70:6657-6654, 2004.

Declaration of David J. Bowen under 37 C.F.R. § 1.132, dated Nov. 30, 2018.

Response to Non-Final Office Action regarding U.S. Appl. No. 16/205,426, dated Jun. 21, 2019.

GenBank Accession No. WP_003343676, Jul. 21, 2013.

Sharma et al., "Genome Sequence of Brevibacillus latersporis Strain GI-9", Journal of Bacteriology, p. 1279, 2012.

Thanabalu et al., "A Bacillus sphaericus gene encoding a novel type of mosquitocidal toxin of 31.8 kDa", Institute of Molecular and Cell Biology, National University of Singapore, pp. 85-89, 1996.

Petit et al., "Clostridium perfringens Epsilon Toxin Induces a Rapid Change of Cell Membrane Permeability to Ions and Forms Channels in Artificial Lipid Bilayers*", The Journal of Biological Chemistry, 276(19):15736-15740, 2001.

GenPept Accession No. WP_003335736, Jan. 13, 2020.

GenPept Accession No. WP_022584503, Jan. 13, 2020.

USPTO: Notice of Allowance regarding U.S. Appl. No. 14/945,140 dated Mar. 10, 2020.

USPTO: Non-Final Office Action regarding U.S. Appl. No. 16/684,007, issued Mar. 16, 2021.

USPTO: Non-Final Office Action regarding U.S. Appl. No. 16/684,029, issued Apr. 1, 2021.

USPTO: Notice of Allowance regarding U.S. Appl. No. 16/684,029, issued Jul. 26, 2021.

USPTO: Notice of Allowance regarding U.S. Appl. No. 16/684,008, issued Aug. 9, 2021.

Artholo-Filho et al., Insects (2014) 5:62-91.

UniProt Accession No. HOUDD3, integrated into UniProt on Feb. 22, 2012.

UniProt Accession No. A0A075R7H4, integrated into UniProt on Oct. 29, 2014.

UniProt Accession No. A0A1777XJY5, integrated into the database on Sep. 7, 2016.

GenBank Accession No. CP007806, dated Jul. 22, 2014.

GenBank Accession No. WP_104065135.1, dated Jul. 29, 2021.

GenBank Accession No. WP_197245544.1, dated Aug. 2, 2021.

GenBank Accession No. MF490290.1, dated Sep. 13, 2017.

GenBank Accession No. ASY04851.1, dated Sep. 13, 2017.

* cited by examiner

SEQ ID NO:   Toxin Protein

24

| SEQ ID NO | Toxin Protein | | | | | | | | | |
|---|---|---|---|---|---|---|---|---|---|---|
| 2 | TIC3668 | mkkfaslilt | svflfsstqf | vhaSSXDVQE | RLRDLAREXE | AGTXNXAWNT | NFKPSDEQQF | SYSPTEGXXF | LTPPKNVIGE | 80 |
| 4 | TIC3669 | mkkfaslilt | svflfsstqf | vhaSSXDVQE | RLRDLAREXE | AGTXNXAWNT | NFKPSDEQQF | SYSPTEGXXF | LTPPKNVIGE | 80 |
| 6 | TIC3670 | mkkfaslilt | svflfsstqf | vhaSSXDVQE | RLRDLAREXE | AGTXNXAWNT | NFKPSDEQQF | SYSPTEGXXF | LTPPKNVIGE | 80 |
| 8 | TIC4076 | mkkfaslilt | svflfsstqf | vhaSSXDVQE | RLRDLAREXE | AGTXNXAWNT | NFKPSDEQQF | SYSPTEGXXF | LTPPKNVIGE | 80 |
| 10 | TIC4078 | mkkfaslilt | svflfsstqf | vhaSSXDVQE | RLRDLAREXE | AGTXNXAWNT | NFKPSDEQQF | SYSPTEGXXF | LTPPKNVIGE | 80 |
| 12 | TIC4260 | mkkfaslilt | svflfsstqf | vhaSSXDVQE | RLRDLAREXE | AGTXNXAWNT | NFKPSDEQQF | SYSPTEGXXF | LTPPKNVIGE | 80 |
| 2 | TIC3668 | RRISXYKVNN | AWATLXGSPT | EXSGTPLYAG | XNVLDNSKGT | MDQEXLTPEF | XYTYTEXTSN | TXTHGLKXGV | KTTATMKFPI | 160 |
| 4 | TIC3669 | RRISXYKVNN | AWATLXGSPT | EXSGTPLYAG | XNVLDNSKGT | XDQEXLTPEF | XYTYTEXTSN | TXTHGLKXGV | KTTATMKFPI | 160 |
| 6 | TIC3670 | RRISXYKVNN | AWATLXGSPT | EXSGTPLYAG | XNVLDNSKGT | XDQEXLTPEF | XYTYTEXTSN | TXTHGLKXGV | KTTATMKFPI | 160 |
| 8 | TIC4076 | RRISXYKVNN | AWATLXGSPT | EXSGTPLYAG | XNVLDNSKGT | SDQEXLTPEF | XYTYTEXTSN | TXTHGLKXGV | KTTATMKFPI | 160 |
| 10 | TIC4078 | RRISXYKVNN | AWATLXGSPT | EXSGTPLYAG | XNVLDNSKGT | XDQEXLTPEF | XYTYTEXTSN | TXTHGLKXGV | KTTATMKFPI | 160 |
| 12 | TIC4260 | RRISXYKVNN | AWATLXGSPT | EXSGTPLYAG | XNVLDNSKGT | XDQEXLTPEF | XYTYTEXTSN | TXTHGLKXGV | KTTATMKFPI | 160 |
| 2 | TIC3668 | AQGSMEASTE | YNFQNSSTDT | KTKQVSYKSP | SQKIKVPAGK | TXRVLAYLNT | GSISGEANLY | ANVGGXAWXV | XPGYPNGGGV | 240 |
| 4 | TIC3669 | AQGSMEASTE | YNFQNSSTDT | KTKQVSYKSP | SQKIKVPAGK | TXRVLAYLNT | GSISGEANLY | ANVGGXAWXV | XPGYPNGGGV | 240 |
| 6 | TIC3670 | AQGSMEASTE | YNFQNSSTDT | KTKQVSYKSP | SQKIKVPAGK | TXRVLAYLNT | GSISGEANLY | ANVGGXAWXV | XPGYPNGGGV | 240 |
| 8 | TIC4076 | AQGSMEASTE | YNFQNSSTDT | KTKQVSYKSP | SQKIKVPAGK | TXRVLAYLNT | GSISGEANLY | ANVGGXAWXV | XPGYPNGGGV | 240 |
| 10 | TIC4078 | AQGSMEASTE | YNFQNSSTDT | KTKQVSYKSP | SQKIKVPAGK | TXRVLAYLNT | GSISGEANLY | ANVGGXAWXV | XPGYPNGGGV | 240 |
| 12 | TIC4260 | AQGSMEASTE | YNFQNSSTDT | KTKQVSYKSP | SQKIKVPAGK | TXRVLAYLNT | GSISGEANLY | ANVGGXAWXV | XPGYPNGGGV | 240 |
| 2 | TIC3668 | NIGAVLTKCQ | QKGWGDFRNF | QPSGRDVIVK | GQGTFXSNYG | TDFILKIEDI | TDSKLRNNNG | SGTVVQEIKV | PLIRTEI | 317 |
| 4 | TIC3669 | NIGAVLTKCQ | QKGWGDFRNF | QPSGRDVIVK | GQGTFXSNYG | TDFILKIEDI | TDSKLRNNNG | SGTVVQEIKV | PLIRTEI | 317 |
| 6 | TIC3670 | NIGAVLTKCQ | QKGWGDFRNF | QPSGRDVIVK | GQGTFXSNYG | TDFILKIEDI | TDSKLRNNNG | SGTVVQEIKV | PLIRTEI | 317 |
| 8 | TIC4076 | NIGAVLTKCQ | QKGWGDFRNF | QPSGRDVIVK | GQGTFXSNYG | TDFILKIEDI | TDSKLRNNNG | SGTVVQEIKV | PLIRTEI | 317 |
| 10 | TIC4078 | NIGAVLTKCQ | QKGWGDFRNF | QPSGRDVIVK | GQGTFXSNYG | TDFILKIEDI | TDSKLRNNNG | SGTVVQEIKV | PLIRTEI | 317 |
| 12 | TIC4260 | NIGAVLTKCQ | QKGWGDFRNF | QPSGRDVIVK | GQGTFXSNYG | TDFILKIEDI | TDSKLRNNNG | SGTVVQEIKV | PLIRTEI | 317 |

FIGURE 1

SEQUENCE LISTING

```
Sequence total quantity: 132
SEQ ID NO: 1              moltype = DNA  length = 954
FEATURE                   Location/Qualifiers
misc_feature              1..954
                          note = A recombinant polynucleotide sequence obtained from
                          a Brevibacillus laterosporus species encoding a TIC3668
                          protein from an open reading frame at nucleotide position
                          1-951 and a translation termination codon.
source                    1..954
                          mol_type = other DNA
                          organism = Brevibacillus laterosporus
SEQUENCE: 1
atgaaaaaat ttgcaagttt aattcttaca agtgtgttcc ttttttcgag tacgcaattt   60
gttcatgcgt catccacaga tgttcaagaa agattacggg acttggcaag agaagatgaa   120
gctggaacct ttaatgaagc atggaatact aacttcaaac ccagtgatga acaacaattc   180
tcgtatagtc caactgaagg aattgttttc ttaacaccac ctaaaaatgt tattggcgaa   240
agaagaattt cacagtataa agtaaataat gcatgggcta cattagtagg aagtccaacc   300
gaagcatcgg ggacaccttt atatgcggga aaaaacgtat tagataactc aaaaggaaca   360
atggatcaag agctgttaac acccgagttt aactatacct atacggaaag cacttcaaat   420
acaataactc atggattaaa attaggagtc aaaaccactg ctaccatgaa attcccgatt   480
gctcagggta gcatggaagc ttctactgaa tataactttc aaaattcttc cactgatact   540
aaaactaaac aagtatcata taaaagccca tcacaaaaaa ttaaagtacc agcaggtaaa   600
acctatagag ttttagcata cctaaatact ggatctattt caggtgaagc taaccttac    660
gcaaatgttg ggggtatagc ttggagggtt tcaccaggtt atcccaatgg cggaggagta   720
aatataggtg ctgtacttac caaatgccaa caaaaaggat ggggagattt cagaaacttt   780
caacctagtg gaagagatgt aatcgttaaa ggccaaggta cttcaaatc taattatgga    840
acggacttca ttttaaaaat tgaagacatc acagattcaa agttacgaaa caataacggg   900
agtggaactg tcgttcaaga gattaaagtt ccactaatta gaactgaaat atag           954

SEQ ID NO: 2              moltype = AA  length = 317
FEATURE                   Location/Qualifiers
REGION                    1..317
                          note = The amino acid sequence translation of the TIC3668
                          precursor protein from the open reading frame as set forth
                          in SEQ ID NO:1.
source                    1..317
                          mol_type = protein
                          organism = Brevibacillus laterosporus
SEQUENCE: 2
MKKFASLILT SVFLFSSTQF VHASSTDVQE RLRDLAREDE AGTFNEAWNT NFKPSDEQQF   60
SYSPTEGIVF LTPPKNVIGE RRISQYKVNN AWATLVGSPT EASGTPLYAG KNVLDNSKGT   120
MDQELLTPEF NYTYTESTSN TITHGLKLGV KTTATMKFPI AQGSMEASTE YNFQNSSTDT   180
KTKQVSYKSP SQKIKVPAGK TYRVLAYLNT GSISGEANLY ANVGGIAWRV SPGYPNGGGV   240
NIGAVLTKCQ QKGWGDFRNF QPSGRDVIVK GQGTFKSNYG TDFILKIEDI TDSKLRNNNG   300
SGTVVQEIKV PLIRTEI                                                    317

SEQ ID NO: 3              moltype = DNA  length = 954
FEATURE                   Location/Qualifiers
misc_feature              1..954
                          note = A recombinant polynucleotide sequence obtained from
                          a Brevibacillus laterosporus species encoding a TIC3669
                          protein from an open reading frame at nucleotide position
                          1-951 and a translation termination codon.
source                    1..954
                          mol_type = other DNA
                          organism = Brevibacillus laterosporus
SEQUENCE: 3
atgaaaaaat ttgcaagttt aattcttata agtgtgttcc ttttttcgag tacgcaattt   60
gttcatgcgt catccacaga tgttcaagaa agattacggg acttggcaag agaagatgaa   120
gctggaacct ttaatgaagc atggaatact aacttcaaac ccagtgatga acaacaattc   180
tcgtatagtc caactgaagg aattgttttc ttaacaccac ctaaaaatgt tattggcgaa   240
agaagaattt cacagtataa agtaaataat gcatgggcta cattagaagg aagtccaacc   300
gaagtatcgg ggacaccttt atatgcggga aaaaacgtat tagataactc aaaaggaaca   360
```

```
atcgatcaag agctgttaac acccgagttt agttatacct atacggaaag cacttcaaat  420
acaacaactc atggattaaa agtaggagtc aaaaccactg ctaccatgaa attcccgatt  480
gctcagggta gcatggaagc ttctactgaa tataactttc aaaattcttc cactgatact  540
aaaactaaac aagtatcata taaaagccca tcacaaaaaa ttaaagtacc agcaggtaaa  600
acctatagag ttttagcata cctaaatact ggatctattt caggtgaagc taacctttac  660
gcaaatgttg ggggtatagc ttggagggtt tcaccaggtt atcccaatgg cggaggagta  720
aatataggtg ctgtacttac caaatgccaa caaaaaggat ggggagattt cagaaacttt  780
caacctagtg gaagagatgt aatcgttaaa ggccaaggta ctttcaaatc taattatgga  840
acggacttca ttttaaaaat tgaagacatc acagattcaa agttacgaaa caataacggg  900
agtggaactg tcgttcaaga gattaaagtt ccactaatta gaactgaaat atag         954
```

```
SEQ ID NO: 4              moltype = AA   length = 317
FEATURE                   Location/Qualifiers
REGION                    1..317
                          note = The amino acid sequence translation of the TIC3669
                           precursor protein from the open reading frame as set forth
                           in SEQ ID NO:3.
source                    1..317
                          mol_type = protein
                          organism = Brevibacillus laterosporus
SEQUENCE: 4
MKKFASLILI SVFLFSSTQF VHASSTDVQE RLRDLAREDE AGTFNEAWNT NFKPSDEQQF  60
SYSPTEGIVF LTPPKNVIGE RRISQYKVNN AWATLEGSPT EVSGTPLYAG KNVLDNSKGT  120
IDQELLTPEF SYTYTESTSN TTTHGLKVGV KTTATMKFPI AQGSMEASTE YNFQNSSTDT  180
KTKQVSYKSP SQKIKVPAGK TYRVLAYLNT GSISGEANLY ANVGGIAWRV SPGYPNGGGV  240
NIGAVLTKCQ QKGWGDFRNF QPSGRDVIVK GQGTFKSNYG TDFILKIEDI TDSKLRNNNG  300
SGTVVQEIKV PLIRTEI                                                  317
```

```
SEQ ID NO: 5              moltype = DNA   length = 954
FEATURE                   Location/Qualifiers
misc_feature             1..954
                          note = A recombinant polynucleotide sequence obtained from
                           a Brevibacillus laterosporus species encoding a TIC3670
                           protein from an open reading frame at nucleotide position
                           1-951 and a translation termination codon.
source                    1..954
                          mol_type = other DNA
                          organism = Brevibacillus laterosporus
SEQUENCE: 5
atgaaaaaat ttgcaagttt aattcttaca agtgtgttcc tttttcgag tacgcaattt  60
gttcatgcgt catccacaga tgttcaagaa agattacggg acttggcaag agaagatgaa  120
gctggaacct ttaatgaagc atggaatact aacttcaaac ccagtgatga acaacaattc  180
tcttatagtc caactgaagg aattgttttc ttaacaccac ctaaaaatgt tattggcgaa  240
agaagaattt cacagtataa agtaaataat gcatgggcta cattagaagg aagtccaacc  300
gaagcatcgg ggacaccttt atatgcggga aaaaacgtat tagataactc aaaaggaaca  360
atggatcaag agctgttaac acccgagttt aactatacct atacggaaag cacttcaaat  420
acaacaaccc atggattaaa attaggagtc aaaaccactg ctaccatgaa attcccgatt  480
gctcagggta gcatggaagc ttctactgaa tataactttc aaaattcttc cactgatact  540
aaaactaaac aagtatcata taaaagccca tcacaaaaaa ttaaagtacc agcaggtaaa  600
acctatagag ttttagcata cctaaatact ggatctattt caggtgaagc taacctttac  660
gcaaatgttg ggggtatagc ttggagggtt tcaccaggtt atcccaatgg cggaggagta  720
aatataggtg ctgtacttac caaatgccaa caaaaaggat ggggagattt cagaaacttt  780
caacctagtg gaagagatgt aatcgttaaa ggccaaggta ctttcaaatc taattatgga  840
acggacttca ttttaaaaat tgaagacatc acagattcaa agttacgaaa caataacggg  900
agtggaactg tcgttcaaga gattaaagtt ccactaatta gaactgaaat atag         954
```

```
SEQ ID NO: 6              moltype = AA   length = 317
FEATURE                   Location/Qualifiers
REGION                    1..317
                          note = The amino acid sequence translation of the TIC3670
                           precursor protein from the open reading frame as set forth
                           in SEQ ID NO:5.
source                    1..317
                          mol_type = protein
                          organism = Brevibacillus laterosporus
SEQUENCE: 6
MKKFASLILT SVFLFSSTQF VHASSTDVQE RLRDLAREDE AGTFNEAWNT NFKPSDEQQF  60
SYSPTEGIVF LTPPKNVIGE RRISQYKVNN AWATLEGSPT EASGTPLYAG KNVLDNSKGT  120
MDQELLTPEF NYTYTESTSN TTTHGLKLGV KTTATMKFPI AQGSMEASTE YNFQNSSTDT  180
KTKQVSYKSP SQKIKVPAGK TYRVLAYLNT GSISGEANLY ANVGGIAWRV SPGYPNGGGV  240
NIGAVLTKCQ QKGWGDFRNF QPSGRDVIVK GQGTFKSNYG TDFILKIEDI TDSKLRNNNG  300
SGTVVQEIKV PLIRTEI                                                  317
```

```
SEQ ID NO: 7              moltype = DNA   length = 954
FEATURE                   Location/Qualifiers
misc_feature             1..954
                          note = A recombinant polynucleotide sequence obtained from
                           a Brevibacillus laterosporus species encoding a TIC4076
                           protein from an open reading frame at nucleotide position
```

```
                        1-951 and a translation termination codon.
source                  1..954
                        mol_type = other DNA
                        organism = Brevibacillus laterosporus
SEQUENCE: 7
atgaaaaaat ttgcaagttt aattcttata agtgtgttcc ttttttcgag tacgcaattt   60
gttcatgcgt catccacaga tgttcaagaa agattacggg acttggcaag agaaaatgaa  120
gctggaaccc ttaatgaagc atggaatact aacttcaaac ccagtgatga acaacaattc  180
tcttatagtc caactgaagg tattgttttc ttaacaccac ctaaaaatgt tattggcgaa  240
agaagaattt cacagtataa agtaaataat gcatgggcta cattagaagg aagtccaacc  300
gaaatgtcgg ggacaccttt atatgcggga aaaaacgtat tagataactc aaaaggaaca  360
agcgatcaag agctgttaac acccgagttt acctatacct atacggaaag cacttcaaat  420
acaacaactc atggattaaa attaggagtc aaaaccactg ctaccatgaa attcccgatt  480
gctcagggta gcatggaagc ttctactgaa tataactttc aaaattcttc cactgatact  540
aaaactaaac aagtatcata taaaagccca tcacaaaaga ttaaagtacc agcaggtaaa  600
acctttagag ttttagcata cctaaatact ggatctattt caggtgaagc taacctttac  660
gcaaatgttg ggggtatagc ttggggggtt ttaccaggtt atcccaatgg cggaggagta  720
aatataggtg ctgtacttac caaatgccaa caaaaaggat ggggagattt cagaaacttt  780
caacctagtg gaagagatgt aatcgttaaa ggccaaggta ctttcacatc taattatgga  840
acggacttca ttttaaaaat tgaagacatc acagattcaa agttacgaaa caataacggg  900
agtggaactg tcgttcaaga gattaaagtt ccactaatta gaactgaaat atag        954
```

```
SEQ ID NO: 8            moltype = AA  length = 317
FEATURE                 Location/Qualifiers
REGION                  1..317
                        note = The amino acid sequence translation of the TIC4076
                         precursor protein from the open reading frame as set forth
                         in SEQ ID NO:7.
source                  1..317
                        mol_type = protein
                        organism = Brevibacillus laterosporus
SEQUENCE: 8
MKKFASLILI SVFLFSSTQF VHASSTDVQE RLRDLARENE AGTLNEAWNT NFKPSDEQQF   60
SYSPTEGIVF LTPPKNVIGE RRISQYKVNN AWATLEGSPT EMSGTPLYAG KNVLDNSKGT  120
SDQELLTPEF TYTYTESTSN TTTHGLKLGV KTTATMKFPI AQGSMEASTE YNFQNSSTDT  180
KTKQVSYKSP SQKIKVPAGK TFRVLAYLNT GSISGEANLY ANVGGIAWGV LPGYPNGGGV  240
NIGAVLTKCQ QKGWGDFRNF QPSGRDVIVK GQGTFTSNYG TDFILKIEDI TDSKLRNNNG  300
SGTVVQEIKV PLIRTEI                                                 317
```

```
SEQ ID NO: 9            moltype = DNA  length = 954
FEATURE                 Location/Qualifiers
misc_feature            1..954
                        note = A recombinant polynucleotide sequence obtained from
                         a Brevibacillus laterosporus species encoding a TIC4078
                         protein from an open reading frame at nucleotide position
                         1-951 and a translation termination codon.
source                  1..954
                        mol_type = other DNA
                        organism = Brevibacillus laterosporus
SEQUENCE: 9
atgaaaaaat ttgcaagttt aattcttaca agtgtgttcc ttttttcgag tacacaattt   60
gttcatgcgt catccacaga tgttcaagaa agattacggg acttggcaag agaaaatgaa  120
gctggaaccc ttaatgtagc atggaatact aacttcaaac ccagtgatga acaacaattc  180
tcttatagtc caactgaagg tttttatttc ttaacaccac ctaaaaatgt tattggcgaa  240
agaagaattt cacattataa agtaaataat gcatgggcta cattagaagg aagtccaacc  300
gaagtatcgg ggacaccttt atatgcggga agaaacgtat tagataactc aaaaggaaca  360
atagatcaag agatgttaac acccgagttt aactatacct atacggaagg cacttcaaat  420
acaacaactc atggattaaa attaggagtc aaaaccactg ctaccatgaa attcccgatt  480
gctcagggta gcatggaagc ttctactgaa tataactttc aaaattcttc cactgatact  540
aaaactaaac aagtatcata taaaagccca tcacaaaaaa ttaaagtacc agcaggtaaa  600
acctttagag ttttagcata cctaaatact ggatctattt caggtgaagc taacctttac  660
gcaaatgttg ggggtgtagc ttggggggtt ttaccaggtt atcccaatgg cggaggagta  720
aatataggtg ctgtacttac caaatgccaa caaaaaggat ggggagattt cagaaacttt  780
caacctagtg gaagagatgt aatcgttaaa ggccaaggta ctttcacatc taattatgga  840
acggacttca ttttaaaaat tgaagacatc acagattcaa agttacgaaa caataacggg  900
agtggaactg tcgttcaaga gattaaagtt ccactaatta gaactgaaat atag        954
```

```
SEQ ID NO: 10           moltype = AA  length = 317
FEATURE                 Location/Qualifiers
REGION                  1..317
                        note = The amino acid sequence translation of the TIC4078
                         precursor protein from the open reading frame as set forth
                         in SEQ ID NO:9.
source                  1..317
                        mol_type = protein
                        organism = Brevibacillus laterosporus
SEQUENCE: 10
MKKFASLILT SVFLFSSTQF VHASSTDVQE RLRDLARENE AGTLNVAWNT NFKPSDEQQF   60
SYSPTEGFIF LTPPKNVIGE RRISHYKVNN AWATLEGSPT EVSGTPLYAG RNVLDNSKGT  120
```

```
IDQEMLTPEF NYTYTEGTSN TTTHGLKLGV KTTATMKFPI AQGSMEASTE YNFQNSSTDT   180
KTKQVSYKSP SQKIKVPAGK TFRVLAYLNT GSISGEANLY ANVGGVAWGV LPGYPNGGGV   240
NIGAVLTKCQ QKGWGDFRNF QPSGRDVIVK GQGTFTSNYG TDFILKIEDI TDSKLRNNNG   300
SGTVVQEIKV PLIRTEI                                                  317

SEQ ID NO: 11              moltype = DNA   length = 954
FEATURE                    Location/Qualifiers
misc_feature               1..954
                           note = A recombinant polynucleotide sequence encoding a
                             collage TIC4260 protein created by combining the natural
                             sequence variation from six native sequences from a
                             Brevibacillus laterosporus species.
source                     1..954
                           mol_type = other DNA
                           organism = synthetic construct SEQUENCE: 11
atgaaaaaat ttgcaagttt aattcttaca agtgtgttcc tttttttcgag tacgcaattt   60
gttcatgcgt catccataga tgttcaagaa agattacgag acttggcaag agaagatgaa   120
gctggaacct ttaatgtagc atggaatact aacttcaaac ccagtgatga acaacaattc   180
tcgtatagtc caactgaagg tttttattttc ttaacaccac ctaaaaatgt tattggcgaa   240
agaagaattt cacattataa agtaaataat gcatgggcta cattagtagg aagtccaacc   300
gaagcatcgg ggacaccttt atatgcggga agaaacgtat tagataactc aaaaggaaca   360
atggatcaag agatgttaac acccgagttt agttatacct atacggaagg cacttcaaat   420
acaataactc atggattaaa agtaggagtc aaaaccactg ctaccatgaa attcccgatt   480
gctcagggta gcatggaagc ttctactgaa tataactttc aaaattcttc cactgatact   540
aaaactaaac aagtatcata taaaagccca tcacaaaaaa ttaaagtacc agcaggtaaa   600
acctatagag ttttagcata cctaaatact ggatctattt caggtgaagc taacctttac   660
gcaaatgttg ggggtgtagc ttggagggtt tcaccaggtt atcccaatgg cggaggagta   720
aatataggtg ctgtacttac caaatgccaa caaaaaggat ggggagattt cagaaacttt   780
caacctagtg gaagagatgt aatcgttaaa ggccaagtca ctttcacatc taattatgga   840
acggacttca tttttaaaaat tgaagacatc acagattcaa agttacgaaa caataacggg   900
agtggaactg tcgttcaaga gattaaagtt ccactaatta gaactgaaat atag           954

SEQ ID NO: 12              moltype = AA   length = 317
FEATURE                    Location/Qualifiers
REGION                     1..317
                           note = The amino acid sequence translation of the open
                             reading frame as set forth in SEQ ID NO:11.
source                     1..317
                           mol_type = protein
                           organism = synthetic construct SEQUENCE: 12
MKKFASLILT SVFLFSSTQF VHASSIDVQE RLRDLAREDE AGTFNVAWNT NFKPSDEQQF   60
SYSPTEGFIF LTPPKNVIGE RRISHYKVNN AWATLVGSPT EASGTPLYAG RNVLDNSKGT   120
MDQEMLTPEF SYTYTEGTSN TITHGLKVGV KTTATMKFPI AQGSMEASTE YNFQNSSTDT   180
KTKQVSYKSP SQKIKVPAGK TYRVLAYLNT GSISGEANLY ANVGGVAWRV SPGYPNGGGV   240
NIGAVLTKCQ QKGWGDFRNF QPSGRDVIVK GQGTFTSNYG TDFILKIEDI TDSKLRNNNG   300
SGTVVQEIKV PLIRTEI                                                  317

SEQ ID NO: 13              moltype = DNA   length = 954
FEATURE                    Location/Qualifiers
misc_feature               1..954
                           note = A recombinant polynucleotide sequence obtained from
                             a Brevibacillus laterosporus species encoding a TIC4346
                             protein from an open reading frame at nucleotide position
                             1-951 and a translation termination codon.
source                     1..954
                           mol_type = other DNA
                           organism = Brevibacillus laterosporus SEQUENCE: 13
atgaaaaaat ttgcaagttt aattcttata agtgtgttcc tttttttcgag tacgcaattt   60
gttcatgcgt catccacaga tgttcaagaa agattacggg acttagcaag agaaaatgaa   120
gctggaaccc ttaatgaagc atggaatact aacttcaaac ccagtgatga acaacaattc   180
tcttatagtc caactgaagg aattgttttc ttaacaccac ctaaaaatgt tattggcgaa   240
agaagaattt cacagtataa agtaaataat gcatgggcta cattagaagg aagtccaacc   300
gaagtatcgg ggacaccttt atatgcggga aaaaacgtat tagataactc aaaaggaaca   360
atggatcaag agctgttaac acccgagttt aactatacct atacggaaag cacttcaaat   420
acaataactc atggattaaa attaggagtc aaaaccactg ctaccatgaa attcccgatt   480
gctcagggta gcatggaagc ttctactgaa tataactttc aaaattcttc cactgatact   540
aaaactaaac aagtatcata taaaagccca tcacaaaaaa ttaaagtacc agcaggtaaa   600
acctttagag ttttagcata cctaaatact ggatctattt caggtgaagc taacctttac   660
gcaaatgttg ggggtatagc ttgggggggtt ttaccaggtt atcccaatgg cggaggagta   720
aatataggtg ctgtacttac caaatgccaa caaaaaggat ggggagattt cagaaacttt   780
caacctagtg gaagagatgt aatcgttaaa ggccaagtca ctttcacatc taattatgga   840
acggacttca tttttaaaaat tgaagacatc acagattcaa agttacgaaa caataacggg   900
agtggaactg tcgttcaaga gattaaagtt ccactaatta gaactgaaat atag           954

SEQ ID NO: 14              moltype = AA   length = 317
FEATURE                    Location/Qualifiers
```

```
REGION                    1..317
                          note = The amino acid sequence translation of the TIC4346
                           precursor protein from the open reading frame as set forth
                           in SEQ ID NO:13.
source                    1..317
                          mol_type = protein
                          organism = Brevibacillus laterosporus
SEQUENCE: 14
MKKFASLILI SVFLFSSTQF VHASSTDVQE RLRDLARENE AGTLNEAWNT NFKPSDEQQF   60
SYSPTEGIVF LTPPKNVIGE RRISQYKVNN AWATLEGSPT EVSGTPLYAG KNVLDNSKGT  120
MDQELLTPEF NYTYTESTSN TITHGLKLGV KTTATMKFPI AQGSMEASTE YNFQNSSTDT  180
KTKQVSYKSP SQKIKVPAGK TFRVLAYLNT GSISGEANLY ANVGGIAWGV LPGYPNGGGV  240
NIGAVLTKCQ QKGWGDFRNF QPSGRDVIVK GQGTFESNYG TDFILKIEDI TDSKLRNNNG  300
SGTVVQEIKV PLIRTEI                                                 317

SEQ ID NO: 15             moltype = DNA   length = 954
FEATURE                   Location/Qualifiers
misc_feature              1..954
                          note = A recombinant polynucleotide sequence obtained from
                           a Brevibacillus laterosporus species encoding a TIC4826
                           protein from an open reading frame at nucleotide position
                           1-951 and a translation termination codon.
source                    1..954
                          mol_type = other DNA
                          organism = Brevibacillus laterosporus
SEQUENCE: 15
atgaaaaaat ttgcaagttt aattcttata agtgtgttcc ttttttcgag tacgcaattt   60
gttcatgcgt catccacaga tgttcaagaa agattacggg acttggcaag agaaaatgaa  120
gctggaaccc ttaatgaagc atggaatact aacttcaaac ccagtgatga acaacaattc  180
tcttatagtc ccactgaagg tattgttttc ttaacaccac ctaaaaatgt tattggcgaa  240
agaagaattt cacagtataa agtaaataat gcatgggcta cattagaagg aagtccaacc  300
gaagtatcgg ggacaccttt atatgcggga aaaaacgtat tagataactc aaaaggaaca  360
atggatcaag agctgttaac acccgagttt aactatacct atacgaaaag cacttcaaat  420
acaacaactc atggattaaa attaggagtc aaaaccactc ctaccatgaa attcccgatt  480
gctcagggta gcatggaagc ttctactgaa tataactttc aaaattcttc cactgatact  540
aaaactaaac aagtatcata taaaagccca tcacaaaaaa ttaaagtacc agcaggtaaa  600
acctatagag ttttagcata cctaaatact ggatctatat caggtgaagc taacctttac  660
gcaaatgttg ggggtatagc ttggggggtt ttaccaggtt atcccaatgg cggaggaata  720
aatataggtg ctgtacttac caaatgccaa caaaaagat ggggagattt cagaaacttt  780
caacctagtg gaagagatgt aatcgttaaa ggccaaggta ctttcaaatc taattatgga  840
acggacttca ttttaaaaat tgaagacatc acagattcaa agttacgaaa caataacggg  900
agtggaactg tcgttcaaga gattaaagtt ccactaatta gaactgaaat atag         954

SEQ ID NO: 16             moltype = AA   length = 317
FEATURE                   Location/Qualifiers
REGION                    1..317
                          note = The amino acid sequence translation of the TIC4826
                           precursor protein from the open reading frame as set forth
                           in SEQ ID NO:15.
source                    1..317
                          mol_type = protein
                          organism = Brevibacillus laterosporus
SEQUENCE: 16
MKKFASLILI SVFLFSSTQF VHASSTDVQE RLRDLARENE AGTLNEAWNT NFKPSDEQQF   60
SYSPTEGIVF LTPPKNVIGE RRISQYKVNN AWATLEGSPT EVSGTPLYAG KNVLDNSKGT  120
MDQELLTPEF NYTYTESTSN TTTHGLKLGV KTTATMKFPI AQGSMEASTE YNFQNSSTDT  180
KTKQVSYKSP SQKIKVPAGK TYRVLAYLNT GSISGEANLY ANVGGIAWGV LPGYPNGGGI  240
NIGAVLTKCQ QKGWGDFRNF QPSGRDVIVK GQGTFKSNYG TDFILKIEDI TDSKLRNNNG  300
SGTVVQEIKV PLIRTEI                                                 317

SEQ ID NO: 17             moltype = DNA   length = 921
FEATURE                   Location/Qualifiers
misc_feature              1..921
                          note = A recombinant polynucleotide sequence obtained from
                           a Brevibacillus laterosporus species encoding a TIC4861
                           protein from an open reading frame at nucleotide position
                           1-918 and a translation termination codon.
source                    1..921
                          mol_type = other DNA
                          organism = Brevibacillus laterosporus
SEQUENCE: 17
atgttccttt tttcgagtac gcaatttgtt catgcgtcat ccacagatgt tcaagaacga   60
ttacgggact tggcaagaga aaatgaagct ggaacccta atgaagcatg gaatactaac  120
ttcaaaccca gtgatgaaca acaattctct tatagtccaa ctgaaggtat tgtttttcttta  180
acaccaccta aaaatgttat tggcgaaaga agaatttcac agtataaagt aaataatgca  240
tgggctacat tagaaggaag tccaaccgaa gtatcgggga cactttata tgcgggaaaa  300
aacgtattag ataactcaaa agggacaagc gatcaagagc tgttaacacc cgagtttaac  360
tatacctata cggaaagcac ttcaaataca acaactcatg gattaaaatt aggagtcaaa  420
accactgcta ccatgaaatt cccgattgct cagggtagca tggaagcttc tactgaatat  480
```

```
aactttcaaa attcttccac tgatactaaa actaaacaag tatcatataa aagcccatca  540
caaaaaatta aagtaccagc aggtaaaacc tatagagttt tagcatacct aaatactgga  600
tctatttcag gtgaagctaa cctttacgca aatattgggg gtatagcttg gggggggttta 660
ccaggttatc ccaatggcgg aggagtaaat ataggtgctg tacttaccaa atgccaacaa  720
aaaggatggg gagatttcag aaactttcaa cctagtgcaa gagatgtaat cgttaaaggc  780
caaggtactt tcaaatctaa ttatggaacg gacttcattt taaaaattga agacatcaca  840
gattcaaagt tacgaaacaa taacgggagt ggaactgtcg ttcaagagat taaagttcca  900
ctaattagaa ctgaaatata g                                            921
```

```
SEQ ID NO: 18            moltype = AA  length = 306
FEATURE                  Location/Qualifiers
REGION                   1..306
                         note = The amino acid sequence translation of the TIC4861
                          precursor protein from the open reading frame as set forth
                          in SEQ ID NO:17.
source                   1..306
                         mol_type = protein
                         organism = Brevibacillus laterosporus
SEQUENCE: 18
MFLFSSTQFV HASSTDVQER LRDLARENEA GTLNEAWNTN FKPSDEQQFS YSPTEGIVFL  60
TPPKNVIGER RISQYKVNNA WATLEGSPTE VSGTPLYAGK NVLDNSKGTS DQELLTPEFN  120
YTYTESTSNT TTHGLKLGVK TTATMKFPIA QGSMEASTEY NFQNSSTDTK TKQVSYKSPS  180
QKIKVPAGKT YRVLAYLNTG SISGEANLYA NIGGIAWGGL PGYPNGGGVN IGAVLTKCQQ  240
KGWGDFRNFQ PSGRDVIVKG QGTFKSNYGT DFILKIEDIT DSKLRNNNGS GTVVQEIKVP  300
LIRTEI                                                             306
```

```
SEQ ID NO: 19            moltype = DNA  length = 948
FEATURE                  Location/Qualifiers
misc_feature             1..948
                         note = A recombinant polynucleotide sequence obtained from
                          a Brevibacillus laterosporus species encoding a TIC4862
                          protein from an open reading frame at nucleotide position
                          1-945 and a translation termination codon.
source                   1..948
                         mol_type = other DNA
                         organism = Brevibacillus laterosporus
SEQUENCE: 19
atgtttgcaa gtttaattct tataagtgtg ttccttttt cgagtacgca atttgttcat   60
gcgtcatcca cagatgttca agaacgatta cgggacttgg caagagaaaa tgaagctgga  120
acccttaatg aagcatggaa tactaacttc aaacccagtg atgaacaaca attctcttat  180
agtccaactg aaggtattgt tttcttaaca ccacctaaaa atgttattgg cgaaagaaga  240
atttcacagt ataaagtaaa taatgcatgg gctacattag aaggaagtcc aaccgaagta  300
tcggggacac ctttatatgc gggaaaaaac gtattagtaa actcaaaagg gacaagcgat  360
caagagctgt taacacccga gtttaactat acctatacgg aaagcacttc aaatacaaca  420
actcatggat taaaattagg agtcaaaacc actgctacca tgaaattccc gattgctcag  480
ggtagcatgg aagcttctac tgaatataac tttcaaaatt cttccactga tactaaaact  540
aaacaagtat catataaaag cccatcacaa aaaattaaag taccagcagg taaaacctaa  600
agagtttttag catacctaaa tactggatct atttcaggtg aagctaacct ttacgcaaat  660
attgggggta gcttggggg gggtttacca ggttatccca atggcggagg agtaaatata  720
ggtgctgtac ttaccaaatg ccaacaaaaa ggatggggag atttcagaaa ctttcaacct  780
agtgcaagag atgtaatcgt taaaggccaa ggtactttca aatctaatta tggaacggac  840
ttcattttaa aaattgaaga catcacagat tcaaagttac gaaacaataa cgggagtgga  900
actgtcgttc aagagattaa agttccacta attagaactg aaatatag              948
```

```
SEQ ID NO: 20            moltype = AA  length = 315
FEATURE                  Location/Qualifiers
REGION                   1..315
                         note = The amino acid sequence translation of the TIC4862
                          precursor protein from the open reading frame as set forth
                          in SEQ ID NO:19.
source                   1..315
                         mol_type = protein
                         organism = Brevibacillus laterosporus
SEQUENCE: 20
MFASLILISV FLFSSTQFVH ASSTDVQERL RDLARENEAG TLNEAWNTNF KPSDEQQFSY  60
SPTEGIVFLT PPKNVIGERR ISQYKVNNAW ATLEGSPTEV SGTPLYAGKN VLDNSKGTSD  120
QELLTPEFNY TYTESTSNTT THGLKLGVKT TATMKFPIAQ GSMEASTEYN FQNSSTDTKT  180
KQVSYKSPSQ KIKVPAGKTY RVLAYLNTGS ISGEANLYAN IGGIAWGGLP GYPNGGGVNI  240
GAVLTKCQQK GWGDFRNFQP SGRDVIVKGQ GTFKSNYGTD FILKIEDITD SKLRNNNGSG  300
TVVQEIKVPL IRTEI                                                   315
```

```
SEQ ID NO: 21            moltype = DNA  length = 954
FEATURE                  Location/Qualifiers
misc_feature             1..954
                         note = A recombinant polynucleotide sequence obtained from
                          a Brevibacillus laterosporus species encoding a TIC4863
                          protein from an open reading frame at nucleotide position
                          1-951 and a translation termination codon.
source                   1..954
```

```
                          mol_type = other DNA
                          organism = Brevibacillus laterosporus
SEQUENCE: 21
atgaaaaaat ttgcaagttt aattcttata agtgtgttcc tttttttcgag tacgcaattt   60
gttcatgcgt catccacaga tgttcaagaa cgattacggg acttggcaag agaaaatgaa   120
gctggaaccc ttaatgaagc atggaatact aacttcaaac ccagtgatga acaacaattc   180
tcttatagtc caactgaagg tattgtttte ttaacaccac ctaaaaatgt tattggcgaa   240
agaagaattt cacagtataa agtaaataat gcatgggcta cattagaagg aagtccaacc   300
gaagtatcgg ggacaccttt atatgcggga aaaaacgtat tagataactc aaaagggaca   360
agcgatcaag agctgttaac acccgagttt aactatacct atacggaaag cacttcaaat   420
acaacaactc atggattaaa attaggagtc aaaaccactg ctaccatgaa attcccgatt   480
gctcagggta gcatggaagc ttctactgaa tataactttc aaaattcttc cactgatact   540
aaaactaaac aagtatcata taaaagccca tcacaaaaaa ttaaagtacc agcaggtaaa   600
acctatagag ttttagcata cctaaatact ggatctattt caggtgaagc taacctttac   660
gcaaatattg ggggtatagc ttggggggggg ttaccaggtt atcccaatgg cggaggagta   720
aatataggtg ctgtacttac caaatgccaa caaaaaggat ggggagattt cagaaacttt   780
caacctagtg gaagagatgt aatcgttaaa ggccaaggta ctttcaaatc taattatgga   840
acggacttca ttttaaaaat tgaagacatc acagattcaa agttacgaaa caataacggg   900
agtggaactg tcgttcaaga gattaaagtt ccactaatta gaactgaaat atag         954

SEQ ID NO: 22               moltype = AA   length = 317
FEATURE                     Location/Qualifiers
REGION                      1..317
                            note = The amino acid sequence translation of the TIC4863
                            precursor protein from the open reading frame as set forth
                            in SEQ ID NO:21.
source                      1..317
                            mol_type = protein
                            organism = Brevibacillus laterosporus
SEQUENCE: 22
MKKFASLILI SVFLFSSTQF VHASSTDVQE RLRDLARENE AGTLNEAWNT NFKPSDEQQF   60
SYSPTEGIVF LTPPKNVIGE RRISQYKVNN AWATLEGSPT EVSGTPLYAG KNVLDNSKGT   120
SDQELLTPEF NYTYTESTSN TTTHGLKLGV KTTATMKFPI AQGSMEASTE YNFQNSSTDT   180
KTKQVSYKSP SQKIKVPAGK TYRVLAYLNT GSISGEANLY ANIGGIAWGG LPGYPNGGGV   240
NIGAVLTKCQ QKGWGDFRNF QPSGRDVIVK GQGTFKSNYG TDFILKIEDI TDSKLRNNNG   300
SGTVVQEIKV PLIRTEI                                                  317

SEQ ID NO: 23               moltype = AA   length = 295
FEATURE                     Location/Qualifiers
REGION                      1..295
                            note = An amino acid sequence of a mature TIC3668 protein,
                            mTIC3688.
source                      1..295
                            mol_type = protein
                            organism = synthetic construct
SEQUENCE: 23
MSSTDVQERL RDLAREDEAG TFNEAWNTNF KPSDEQQFSY SPTEGIVFLT PPKNVIGERR   60
ISQYKVNNAW ATLVGSPTEA SGTPLYAGKN VLDNSKGTMD QELLTPEFNY TYTESTSNTI   120
THGLKLGVKT TATMKFPIAQ GSMEASTEYN FQNSSTDTKT KQVSYKSPSQ KIKVPAGKTY   180
RVLAYLNTGS ISGEANLYAN VGGIAWRVSP GYPNGGGVNI GAVLTKCQQK GWGDFRNFQP   240
SGRDVIVKGQ GTFKSNYGTD FILKIEDITD SKLRNNNGSG TVVQEIKVPL IRTEI        295

SEQ ID NO: 24               moltype = AA   length = 295
FEATURE                     Location/Qualifiers
REGION                      1..295
                            note = An amino acid sequence of a mature TIC3669 protein
                            mTIC3669.
source                      1..295
                            mol_type = protein
                            organism = synthetic construct
SEQUENCE: 24
MSSTDVQERL RDLAREDEAG TFNEAWNTNF KPSDEQQFSY SPTEGIVFLT PPKNVIGERR   60
ISQYKVNNAW ATLEGSPTEV SGTPLYAGKN VLDNSKGTID QELLTPEFSY TYTESTSNTT   120
THGLKVGVKT TATMKFPIAQ GSMEASTEYN FQNSSTDTKT KQVSYKSPSQ KIKVPAGKTY   180
RVLAYLNTGS ISGEANLYAN VGGIAWRVSP GYPNGGGVNI GAVLTKCQQK GWGDFRNFQP   240
SGRDVIVKGQ GTFKSNYGTD FILKIEDITD SKLRNNNGSG TVVQEIKVPL IRTEI        295

SEQ ID NO: 25               moltype = AA   length = 295
FEATURE                     Location/Qualifiers
REGION                      1..295
                            note = An amino acid sequence of a mature TIC3670 protein,
                            mTIC3670.
source                      1..295
                            mol_type = protein
                            organism = synthetic construct
SEQUENCE: 25
MSSTDVQERL RDLAREDEAG TFNEAWNTNF KPSDEQQFSY SPTEGIVFLT PPKNVIGERR   60
ISQYKVNNAW ATLEGSPTEA SGTPLYAGKN VLDNSKGTMD QELLTPEFNY TYTESTSNTT   120
THGLKLGVKT TATMKFPIAQ GSMEASTEYN FQNSSTDTKT KQVSYKSPSQ KIKVPAGKTY   180
```

-continued

```
RVLAYLNTGS ISGEANLYAN VGGIAWRVSP GYPNGGGVNI GAVLTKCQQK GWGDFRNFQP    240
SGRDVIVKGQ GTFKSNYGTD FILKIEDITD SKLRNNNGSG TVVQEIKVPL IRTEI          295

SEQ ID NO: 26                moltype = AA  length = 295
FEATURE                      Location/Qualifiers
REGION                       1..295
                             note = An amino acid sequence of a mature TIC4076 protein,
                             mTIC4076.
source                       1..295
                             mol_type = protein
                             organism = synthetic construct
SEQUENCE: 26
MSSTDVQERL RDLARENEAG TLNEAWNTNF KPSDEQQFSY SPTEGIVFLT PPKNVIGERR    60
ISQYKVNNAW ATLEGSPTEM SGTPLYAGKN VLDNSKGTSD QELLTPEFTY TYTESTSNTT    120
THGLKLGVKT TATMKFPIAQ GSMEASTEYN FQNSSTDTKT KQVSYKSPSQ KIKVPAGKTF    180
RVLAYLNTGS ISGEANLYAN VGGIAWGVLP GYPNGGGVNI GAVLTKCQQK GWGDFRNFQP    240
SGRDVIVKGQ GTFTSNYGTD FILKIEDITD SKLRNNNGSG TVVQEIKVPL IRTEI          295

SEQ ID NO: 27                moltype = AA  length = 295
FEATURE                      Location/Qualifiers
REGION                       1..295
                             note = An amino acid sequence of a mature TIC4078 protein,
                             mTIC4078.
source                       1..295
                             mol_type = protein
                             organism = synthetic construct
SEQUENCE: 27
MSSTDVQERL RDLARENEAG TLNVAWNTNF KPSDEQQFSY SPTEGFIFLT PPKNVIGERR    60
ISHYKVNNAW ATLEGSPTEV SGTPLYAGRN VLDNSKGTID QEMLTPEFNY TYTEGTSNTT    120
THGLKLGVKT TATMKFPIAQ GSMEASTEYN FQNSSTDTKT KQVSYKSPSQ KIKVPAGKTF    180
RVLAYLNTGS ISGEANLYAN VGGVAWGVLP GYPNGGGVNI GAVLTKCQQK GWGDFRNFQP    240
SGRDVIVKGQ GTFTSNYGTD FILKIEDITD SKLRNNNGSG TVVQEIKVPL IRTEI          295

SEQ ID NO: 28                moltype = AA  length = 295
FEATURE                      Location/Qualifiers
REGION                       1..295
                             note = An amino acid sequence of a mature TIC4260 protein,
                             mTIC4260.
source                       1..295
                             mol_type = protein
                             organism = synthetic construct
SEQUENCE: 28
MSSIDVQERL RDLAREDEAG TFNVAWNTNF KPSDEQQFSY SPTEGFIFLT PPKNVIGERR    60
ISHYKVNNAW ATLVGSPTEA SGTPLYAGRN VLDNSKGTMD QEMLTPEFSY TYTEGTSNTI    120
THGLKVGVKT TATMKFPIAQ GSMEASTEYN FQNSSTDTKT KQVSYKSPSQ KIKVPAGKTY    180
RVLAYLNTGS ISGEANLYAN VGGVAWRVSP GYPNGGGVNI GAVLTKCQQK GWGDFRNFQP    240
SGRDVIVKGQ GTFTSNYGTD FILKIEDITD SKLRNNNGSG TVVQEIKVPL IRTEI          295

SEQ ID NO: 29                moltype = AA  length = 295
FEATURE                      Location/Qualifiers
REGION                       1..295
                             note = An amino acid sequence of a mature TIC4346 protein,
                             mTIC4346.
source                       1..295
                             mol_type = protein
                             organism = synthetic construct
SEQUENCE: 29
MSSTDVQERL RDLARENEAG TLNEAWNTNF KPSDEQQFSY SPTEGIVFLT PPKNVIGERR    60
ISQYKVNNAW ATLEGSPTEV SGTPLYAGKN VLDNSKGTMD QELLTPEFNY TYTESTSNTI    120
THGLKLGVKT TATMKFPIAQ GSMEASTEYN FQNSSTDTKT KQVSYKSPSQ KIKVPAGKTF    180
RVLAYLNTGS ISGEANLYAN VGGIAWGVLP GYPNGGGVNI GAVLTKCQQK GWGDFRNFQP    240
SGRDVIVKGQ GTFESNYGTD FILKIEDITD SKLRNNNGSG TVVQEIKVPL IRTEI          295

SEQ ID NO: 30                moltype = AA  length = 295
FEATURE                      Location/Qualifiers
REGION                       1..295
                             note = An amino acid sequence of a mature TIC4826 protein,
                             mTIC4826.
source                       1..295
                             mol_type = protein
                             organism = synthetic construct
SEQUENCE: 30
MSSTDVQERL RDLARENEAG TLNEAWNTNF KPSDEQQFSY SPTEGIVFLT PPKNVIGERR    60
ISQYKVNNAW ATLEGSPTEV SGTPLYAGKN VLDNSKGTMD QELLTPEFNY TYTESTSNTT    120
THGLKLGVKT TATMKFPIAQ GSMEASTEYN FQNSSTDTKT KQVSYKSPSQ KIKVPAGKTY    180
RVLAYLNTGS ISGEANLYAN VGGIAWGVLP GYPNGGGINI GAVLTKCQQK GWGDFRNFQP    240
SGRDVIVKGQ GTFKSNYGTD FILKIEDITD SKLRNNNGSG TVVQEIKVPL IRTEI          295

SEQ ID NO: 31                moltype = AA  length = 295
```

-continued

```
FEATURE            Location/Qualifiers
REGION             1..295
                   note = An amino acid sequence of a mature TIC4861 protein,
                   mTIC4861.
source             1..295
                   mol_type = protein
                   organism = synthetic construct
SEQUENCE: 31
MSSTDVQERL RDLARENEAG TLNEAWNTNF KPSDEQQFSY SPTEGIVFLT PPKNVIGERR  60
ISQYKVNNAW ATLEGSPTEV SGTPLYAGKN VLDNSKGTSD QELLTPEFNY TYTESTSNTT  120
THGLKLGVKT TATMKFPIAQ GSMEASTEYN FQNSSTDTKT KQVSYKSPSQ KIKVPAGKTY  180
RVLAYLNTGS ISGEANLYAN IGGIAWGGLP GYPNGGGVNI GAVLTKCQQK GWGDFRNFQP  240
SGRDVIVKGQ GTFKSNYGTD FILKIEDITD SKLRNNNGSG TVVQEIKVPL IRTEI       295

SEQ ID NO: 32      moltype = DNA   length = 954
FEATURE            Location/Qualifiers
misc_feature       1..954
                   note = A synthetic nucleotide sequence encoding a TIC3668
                    protein designed for expression in plants.
source             1..954
                   mol_type = other DNA
                   organism = synthetic construct
SEQUENCE: 32
atgaagaagt tcgcgtcgct gatcctcacc agcgtgttcc tgtttagtag cacgcagttc  60
gtccacgcct catccacgga cgtgcaagag cgcctgcggg acttggcgcg cgaagacgag  120
gcgggaacgt tcaacgaggc ttggaacacc aacttcaagc cgtcggacga gcagcaattc  180
agctactcgc cgacggaggg aattgtcttc ctcacgccgc ctaagaacgt catcggtgag  240
cggcgcatct cccagtacaa ggtgaacaat gcctgggcaa ctctggtggg ctctcccacc  300
gaggcgagcg gtacgccgtt gtacgcgggc aagaatgtac tggacaactc gaaaggcaca  360
atggaccagg agttgcttac acccgagttc aactacacct acggagagag cgagcaac    420
acgatcacgc acggcctcaa actcggcgtg aagaccaccg cgaccatgaa gttccctatc  480
gctcaaggct cgatggaggc gagcaccgag tacaatttcc agaactcctc caccgatacc  540
aagaccaaac aagtgtctta caagtctccg agccagaaga ttaaggttcc tgcgggcaag  600
acgtaccgcg tgctggcgta cctgaacacc ggctctatct ctggcgaggc taacctgtac  660
gcgaacgtcg gcggcatcgc gtggcgggtc tcgccaggct atcctaacgg cggcggcgtg  720
aacatcggcg ctgtcctgac caagtgccag cagaagggtt ggggcgactt ccgcaacttc  780
cagccctccg ggcgcgacgt catcgtgaag ggtcagggca ccttcaagtc caactacggc  840
accgacttca tccttaagat tgaggacatc accgacagca agctccgcaa caacaacggc  900
tccgggacgg tcgtacagga gatcaaggtg ccactcatcc gcaccgagat ttga        954

SEQ ID NO: 33      moltype = DNA   length = 888
FEATURE            Location/Qualifiers
misc_feature       1..888
                   note = A synthetic nucleotide sequence encoding a mature
                    TIC3668 protein, mTIC3668 designed for expression in
                    plants.
source             1..888
                   mol_type = other DNA
                   organism = synthetic construct
SEQUENCE: 33
atgtcatcca cggacgtgca agagcgcctg cgggacttgg cgcgcgaaga cgaggcggga  60
acgttcaacg aggcttggaa caccaacttc aagccgtcgg acgagcagca attcagctac  120
tcgccgacgg agggaattgt cttcctcacg ccgcctaaga cgtcatcgg tgagcggcgc  180
atctcccagt acaaggtgaa caatgcctgg gcaactctgg tgggctctcc caccgaggcg  240
agcggtacgc cgttgtacgc gggcaagaat gtactggaca actcgaaagg cacaatggac  300
caggagttgc ttacacccga gttcaactac acctacacgg agagcacgag caacacgatc  360
acgcacggcc tcaaactcgg cgtgaagacc accgcgacca tgaagttccc tatcgctcaa  420
ggctcgatga ggcgagcac cgagtacaat ttccagaact cctccaccga taccaagacc  480
aaacaagtgt cttacaagtc tccgagccag aagattaagg ttcctgcggg caagacgtac  540
cgcgtgctgg cgtacctgaa caccggctct atctctggcg aggctaacct gtacgcgaac  600
gtcggcggca tcgcgtggcg ggtctcgcca ggctatccta acggcggcgg cgtgaacatc  660
ggcgctgtcc tgaccaagtg ccagcagaag ggttggggcg acttccgcaa cttccagccc  720
tccgggcgcg acgtcatcgt gaagggtcag ggcaccttca gtccaacta cggcaccgac  780
ttcatcctta agattgagga catcaccgac agcaagctcc gcaacaacaa cggctccggg  840
acggtcgtac aggagatcaa ggtgccactc atccgcaccg agatttga              888

SEQ ID NO: 34      moltype = DNA   length = 954
FEATURE            Location/Qualifiers
misc_feature       1..954
                   note = A synthetic nucleotide sequence encoding a TIC3669
                    protein designed for expression in plants.
source             1..954
                   mol_type = other DNA
                   organism = synthetic construct
SEQUENCE: 34
atgaagaagt tcgcgtcgct gatcctcatc agcgtgttcc tgtttagtag cacgcagttc  60
gtccacgcct catccacgga cgtgcaagag cgcctgcggg acttggcgcg cgaagacgag  120
gcgggaacgt tcaacgaggc ttggaacacc aacttcaagc cgtcggacga gcagcaattc  180
agctactcgc cgacggaggg aattgtcttc ctcacgccgc ctaagaacgt catcggtgag  240
```

-continued

```
cggcgcatct cccagtacaa ggtgaacaat gcctgggcaa ctctggaggg ctctcccacc   300
gaggtcagcg gtacgccgtt gtacgcgggc aagaatgtac tggacaactc gaaaggcaca   360
atagaccagg agttgcttac acccgagttc tcgtacacct acacggagag cacgagcaac   420
acgacgacgc acggcctcaa agtcggccgtg aagaccaccg cgaccatgaa gttccctatc   480
gctcaaggct cgatggaggc gagcaccgag tacaatttcc agaactcctc caccgatacc   540
aagaccaaac aagtgtctta caagtctccg agccagaaga ttaaggttcc tgcgggcaag   600
acgtaccgcg tgctggcgta cctgaacacc ggctctatct ctggcgaggc taacctgtac   660
gcgaacgtcg cgggcatcgc gtggcgggtc tcgccaggct atcctaacgg cggcggcgtg   720
aacatcggcg ctgtcctgac caagtgccag cagaaggggt ggggcgactt ccgcaacttc   780
cagccctccg ggcgcgacgt catcgtgaag ggtcagggca ccttcaagtc caactacggc   840
accgacttca tccttaagat tgaggacatc accgacagca agctccgcaa caacaacggc   900
tccgggacgg tcgtacagga gatcaaggtg ccactcatcc gcaccgagat ttga         954

SEQ ID NO: 35            moltype = DNA  length = 888
FEATURE                  Location/Qualifiers
misc_feature            1..888
                        note = A synthetic nucleotide sequence encoding a mature
                        TIC3669 protein, mTIC3669 designed for expression in
                        plants.
source                  1..888
                        mol_type = other DNA
                        organism = synthetic construct
SEQUENCE: 35
atgtcatcca cggacgtgca agagcgcctg cgggacttgg cgcgcgaaga cgaggcggga   60
acgttcaacg aggcttggaa caccaacttc aagccgtcgg acgagcagca attcagctac   120
tcgccgacgg agggaattgt cttcctcacg ccgcctaaga acgtcatcgg tgagcggcgc   180
atctcccagt acaaggtgaa caatgcctgg gcaactctgg agggctctcc caccgaggtc   240
agcggtacgc cgttgtacgc gggcaagaat gtactggaca actcgaaagg cacaatagac   300
caggagttgc ttacacccga gttctcgtac acctacacgg agagcacgag caacacgacg   360
acgcacggcc tcaaagtcgg cgtgaagacc accgcgcgaacc tgaagttccc tatcgctcaa   420
ggctcgatgg aggcgagcac cgagtacaat ttccagaact cctccaccga taccaagacc   480
aaacaagtgt cttacaagtc tccgagccag aagattaagg ttcctgcggg caagacgtac   540
cgcgtgctgc cgtacctgaa caccggctct atctctggcg aggctaacct gtacgcgaac   600
gtcggcggca tcgcgtggcg ggtctcgcca ggctatccta acggcggcgg cgtgaacatc   660
ggcgctgtcc tgaccaagtg ccagcagaag ggttgggggcg acttccgcaa cttccagccc   720
tccgggcgcg acgtcatcgt gaagggtcag ggcaccttca agtccaacta cggcaccgac   780
ttcatcctta agattgagga catcaccgac agcaagctcc gcaacaacaa cggctccggg   840
acggtcgtac aggagatcaa ggtgccactc atccgcaccg agatttga               888

SEQ ID NO: 36            moltype = DNA  length = 954
FEATURE                  Location/Qualifiers
misc_feature            1..954
                        note = A synthetic nucleotide sequence encoding a TIC3670
                        protein designed for expression in plants.
source                  1..954
                        mol_type = other DNA
                        organism = synthetic construct
SEQUENCE: 36
atgaagaagt tcgcgtcgct gatcctcacc agcgtgttcc tgtttagtag cacgcagttc   60
gtccacgcct catccacgga cgtgcaagag cgcctgcggg acttggcgcg cgaagacgag   120
gcgggaacgt tcaacgaggc ttggaacacc aacttcaagc cgtcggacga gcagcaattc   180
agctactcgc cgacggaggg aattgtcttc tcacgccgc ctaagaacgt catcggtgag   240
cggcgcatct cccagtacaa ggtgaacaat gcctgggcaa ctctggaggg ctctcccacc   300
gaggcgagcg gtacgccgtt gtacgcgggc aagaatgtac tggacaactc gaaaggcaca   360
atggaccagg agttgcttac acccgagttc aactacacct acacggagag cacgagcaac   420
acgacgacgc acggcctcaa actcggccgtg aagaccaccg cgaccatgaa gttccctatc   480
gctcaaggct cgatggaggc gagcaccgag tacaatttcc agaactcctc caccgatacc   540
aagaccaaac aagtgtctta caagtctccg agccagaaga ttaaggttcc tgcgggcaag   600
acgtaccgcg tgctggcgta cctgaacacc ggctctatct ctggcgaggc taacctgtac   660
gcgaacgtcg cgggcatcgc gtggcgggtc tcgccaggct atcctaacgg cggcggcgtg   720
aacatcggcg ctgtcctgac caagtgccag cagaagggtt ggggcgactt ccgcaacttc   780
cagccctccg ggcgcgacgt catcgtgaag ggtcagggca ccttcaagtc caactacggc   840
accgacttca tccttaagat tgaggacatc accgacagca agctccgcaa caacaacggc   900
tccgggacgg tcgtacagga gatcaaggtg ccactcatcc gcaccgagat ttga         954

SEQ ID NO: 37            moltype = DNA  length = 888
FEATURE                  Location/Qualifiers
misc_feature            1..888
                        note = A synthetic nucleotide sequence encoding a mature
                        TIC3670 protein, mTIC3670 designed for expression in
                        plants.
source                  1..888
                        mol_type = other DNA
                        organism = synthetic construct
SEQUENCE: 37
atgtcatcca cggacgtgca agagcgcctg cgggacttgg cgcgcgaaga cgaggcggga   60
acgttcaacg aggcttggaa caccaacttc aagccgtcgg acgagcagca attcagctac   120
tcgccgacgg agggaattgt cttcctcacg ccgcctaaga acgtcatcgg tgagcggcgc   180
atctcccagt acaaggtgaa caatgcctgg gcaactctgg agggctctcc caccgaggcg   240
```

-continued

```
agcggtacgc cgttgtacgc gggcaagaat gtactggaca actcgaaagg cacaatggac    300
caggagttgc ttacacccga gttcaactac acctacacgg agagcacgag caacacgacg    360
acgcacggcc tcaaactcgg cgtgaagacc accgcgacca tgaagttccc tatcgctcaa    420
ggctcgatgg aggcgagcac cgagtacaat ttccagaact cctccaccga taccaagacc    480
aaacaagtgt cttacaagtc tccgagccag aagattaagg ttcctgcggg caagacgtac    540
cgcgtgctgg cgtacctgaa caccggctct atctctggcg aggctaacct gtacgcgaac    600
gtcggcggca tcgcgtggcg ggtctcgcca ggctatccta acggcggcgg cgtgaacatc    660
ggcgctgtcc tgaccaagtg ccagcagaag ggttggggcg acttccgcaa cttccagccc    720
tccgggcgcg acgtcatcgt gaagggtcag ggcaccttca agtccaacta cggcaccgac    780
ttcatcctta agattgagga catcaccgac agcaagctcc gcaacaacaa cggctccggg    840
acggtcgtac aggagatcaa ggtgccactc atccgcaccg agatttga                 888

SEQ ID NO: 38          moltype = DNA  length = 954
FEATURE                Location/Qualifiers
misc_feature           1..954
                       note = A synthetic nucleotide sequence encoding a TIC4076
                       protein designed for expression in plants.
source                 1..954
                       mol_type = other DNA
                       organism = synthetic construct
SEQUENCE: 38
atgaagaagt tcgcgagttt gatcctgatc agtgtgttcc tcttctcctc tacccagttc    60
gtgcacgcga gcagcaccga cgtgcaagag cgcctgcggg acctcgcacg ggagaacgaa   120
gccgggacct taaacgaggc ctggaacact aacttcaagc cctccgacga gcagcagttc   180
tcctacagcc ctactgaggg tatcgtcttc ttgacgcctc ctaagaacgt catcggtgag   240
cgccgcatca gccagtacaa ggtgaacaat gcctgggca cgttggaagg aagccctacc   300
gagatgtccg gtacgccgtt gtacgccggc aagaacgtgc tagacaactc caaaggcacg   360
tccgaccagg agctgctcac tccagagttc acttacacct acaccgagag tacatcaaac   420
accaccaccc acgcctgaa gctgggcgtg aagaccactg caaccatgaa gtttccgata   480
gcccagggct ccatggaggc gagcacagag tacaacttcc agaactcctc gaccgacacg   540
aagaccaagc aagtatctta caagtcgccg tcacagaaga tcaaggtccc tgcgggcaag   600
acgttcaggg tcctggcgta cctgaacacc ggatcaatct ccggcgaggc gaatctgtac   660
gctaatgtag gtggcatcgc ctggggtgtg ctgccaggct accctaacgg tggaggcgta   720
aacatcggag ccgtgttgac gaaatgccag cagaagggc ggggcgattt cagaaacttt   780
caaccgagcg ggaggacgt cattgtgaag ggccagggca cattcacatc caactacggg   840
acagacttca tcctgaagat cgaggacata accgacagca aactgaggaa caataacgga   900
tcgggtacgg tagtacagga gatcaaagtc ccgctgatcc ggacggagat ctag         954

SEQ ID NO: 39          moltype = DNA  length = 888
FEATURE                Location/Qualifiers
misc_feature           1..888
                       note = A synthetic nucleotide sequence encoding a mature
                       TIC4076 protein, mTIC4076 designed for expression in
                       plants.
source                 1..888
                       mol_type = other DNA
                       organism = synthetic construct
SEQUENCE: 39
atgagcagca ccgacgtgca agagcgcctg cgggacctcg cacgggagaa cgaagccggg    60
accttaaacg aggcctggaa cactaacttc aagccctccg acgagcagca gttctcctac   120
agccctactg agggtatcgt cttcttgacg cctcctaaga acgtcatcgg tgagcgcgc   180
atcagccagt acaaggtgaa caatgcctgg gccacgttgg aaggaagccc taccgagatg   240
tccggtacgc cgttgtacgc cggcaagaac gtgctagaca actccaaagg cacgtccgac   300
caggagctgc tcactccaga gttcacttac acctacaccg agtacatc aaacaccacc   360
acccacggcc tgaagctggg cgtgaagacc actgcaaacc atgaagtttcc gatagcccag   420
ggctccatgg aggcgagcac agagtacaac ttccagaact cctcgaccga cacgaagacc   480
aagcaagtat cttacaagtc gccgtcacag aagatcaagg tccctgcggg caagacgttc   540
agggtcctgg cgtacctgaa caccggatca atctccggcg aggcgaatct gtacgctaat   600
gtaggtggca tcgcctgggg tgtgctgcca ggctaccctc acggtggagg cgtaaacatc   660
ggagccgtgt tgacgaaatg ccagcagaag ggctggggcg atttcagaaa ctttcaaccg   720
agcgggaggg acgtcattgt gaagggccag ggcacattca tccaacta cgggacagac   780
ttcatcctga gatcgagga cataaccgac agcaaactga ggaacaataa cggatcgggt   840
acggtagtac aggagatcaa agtcccgctg atccggacgg agatctag              888

SEQ ID NO: 40          moltype = DNA  length = 888
FEATURE                Location/Qualifiers
misc_feature           1..888
                       note = A synthetic nucleotide sequence encoding a TIC4078
                       protein designed for expression in plants.
source                 1..888
                       mol_type = other DNA
                       organism = synthetic construct
SEQUENCE: 40
atgagcagca ccgacgtgca agagcgcctg cgggacctcg cacgggagaa cgaagccggg    60
accttaaacg aggcctggaa cactaacttc aagccctccg acgagcagca gttctcctac   120
agccctactg agggtatcgt cttcttgacg cctcctaaga acgtcatcgg tgagcgccgc   180
atcagccagt acaaggtgaa caatgcctgg gccacgttgg aaggaagccc taccgagatg   240
tccggtacgc cgttgtacgc cggcaagaac gtgctagaca actccaaagg cacgtccgac   300
caggagctgc tcactccaga gttcacttac acctacaccg agtacatc aaacaccacc   360
```

-continued

```
acccacggcc tgaagctggg cgtgaagacc actgcaacca tgaagtttcc gatagcccag   420
ggctccatgg aggcgagcac agagtacaac ttccagaact cctcgaccga cacgaagacc   480
aagcaagtat cttacaagtc gccgtcacag aagatcaagg tccctgcggg caagacgttc   540
agggtcctga cgtacctgaa caccggatca atctccggcg aggcgaatct gtacgctaat   600
gtaggtggca tcgcctgggg tgtgctgcca ggctacccta acggtggagg cgtaaacatc   660
ggagccgtgt tgacgaaatg ccagcagaag ggctggggcg atttcagaaa ctttcaaccg   720
agcgggaggg acgtcattgt gaagggccag ggcacattca catccaacta cgggacagac   780
ttcatcctga agatcgagga cataaccgac agcaaactga ggaacaataa cggatcgggt   840
acggtagtac aggagatcaa agtcccgctg atccggacgg agatctag              888
```

SEQ ID NO: 41          moltype = DNA  length = 888
FEATURE                Location/Qualifiers
misc_feature           1..888
                       note = A synthetic nucleotide sequence encoding a mature
                       TIC4078 protein, mTIC4078 designed for expression in
                       plants.
source                 1..888
                       mol_type = other DNA
                       organism = synthetic construct SEQUENCE: 41
```
atgagctcca ccgacgttca ggagcgcctc cgggacttgg caagagagaa tgaggcgggt   60
acgctcaatg tcgcctggaa caccaacttc aagccgtccg acgaacagca gttctcctac   120
tctcctacgg aagggttcat cttcctgaca ccgcccaaga acgtcatcgg cgagcggcgc   180
atcagccatt acaaggtcaa caatgcgtgg gctacgctgg agggcagtcc gaccgaggtg   240
agcggcactc cactctacgc cgggagaaac gtcctcgaca attccaaggg caccatcgac   300
caggagatgt tgacgcctga gttcaactac acgtacaccg agggcacctc taacaccacc   360
actcatggcc tcaagcttgg cgtgaagaca actgcgacaa tgaagtttcc catcgcccaa   420
ggcagtatgg aggcctcgac ggagtacaac ttccagaaca gcagcaccga cactaagacc   480
aagcaagtgt cctacaagag tccatcacag aagatcaaag tcccggccgg caagacattc   540
cgagtgctgg cgtacctaaa caccgggtcg atctcgggcg aggccaacct ttacgccaat   600
gtgggcggcg tcgcatgggg cgtgctgccc ggctatccga acggaggcgg cgtgaacatc   660
ggcgctgtgc tcaccaagtg ccaacagaag ggatggggcg acttccgcaa cttccaaccc   720
tccggtaggg acgtcatagt gaagggccag ggcacgttta catctaacta cgggacggac   780
ttcatactca agatcgagga catcacagat agtaagctca ggaacaacaa cgggtccggc   840
accgtcgttc aggagatcaa ggtcccgttg attaggacgg agatctga              888
```

SEQ ID NO: 42          moltype = DNA  length = 954
FEATURE                Location/Qualifiers
misc_feature           1..954
                       note = A synthetic nucleotide sequence encoding a TIC4260
                       protein designed for expression in plants.
source                 1..954
                       mol_type = other DNA
                       organism = synthetic construct SEQUENCE: 42
```
atgaagaagt tcgcctcact gatccttacc tcggtcttcc tgttctcttc cactcagttc   60
gtgcacgcca gctccataga cgtccaggag cggctcaagc acttggcgcg ggaggacgag   120
gccggcacct ttaacgtggc ctggaacacg aactttaagc cttcagacga gcagcagttc   180
tcctacagcc ctactgaggg cttcatcttt ctgactccgc caaagaatgt gatcggcgaa   240
aggcggatca gtcactacaa agtgaacaac gcttgggcca cgctcgtggg ctcacccacg   300
gaagcgtcag ggacgcctct ctacgccggt aggaacgtgc tggataattc caagggtcag   360
atggaccagg agatgctgac gcccgagttc agctacactt acacagaggg cacgtccaac   420
acgatcacac atgggctcaa ggtgggtgtc aagaccaccg ctaccatgaa gttcccgatc   480
gctcagggct ccatggaagc gagcacagag tacaactttc agaactcttc gacggacacg   540
aagaccaagg aagtttccta caagagccct agccagaaga tcaaggtccc tgcgggcaag   600
acgtaccgcg ttctggccta tctgaacacc ggctccataa gcggcgaggc gaacctgtac   660
gctaatgtgg gtggcgtcgc ttggcgcgtc agtccgggtt acccgaacgg cggcggcgtg   720
aacatcggcg ccgtgttaac taagtgccag cagaagggct ggggcgactt cagaaatttc   780
cagccttccg gccgggacgt catcgtgaag ggccagggca ccttcacctc aaactacggg   840
acagacttta tccttaagat cgaggacatc accgacagca gtccgaaa caacaacggc   900
tccggcaccg tcgtgcaaga gattaaggtc ccgctcatta ggacggagat ctaa         954
```

SEQ ID NO: 43          moltype = DNA  length = 888
FEATURE                Location/Qualifiers
misc_feature           1..888
                       note = A synthetic nucleotide sequence encoding a mature
                       TIC4260 protein, mTIC4260 designed for expression in
                       plants.
source                 1..888
                       mol_type = other DNA
                       organism = synthetic construct SEQUENCE: 43
```
atgagctcca tagacgtcca ggagcggctc agggacttgg cgcgggagga cgaggccggc   60
acctttaacg tggcctggaa cacgaacttt aagccttcag acgagcagca gttctcctac   120
agccctactg agggcttcat ctttctgact ccgccaaaga atgtgatcgg cgaaaggcgg   180
atcagtcact acaaagtgaa caacgcttgg gccacgctcg tgggctcacc cacggaagcg   240
tcagggacgc tctctacgc cggtaggaac gtgctggata ttccaaggg tacgatggac   300
caggagatgc tgacgcccga gttcagctac acttacacag agggcacgtc caacacgatc   360
acacatgggc tcaaggtggg tgtcaagacc accgctacca tgaagttccc gatcgctcag   420
```

```
ggctccatgg aagcgagcac agagtacaac tttcagaact cttcgacgga cacgaagacc  480
aagcaagttt cctacaagag ccctagccag aagatcaagg tccctgcggg caagacgtac  540
cgcgttctgg cctatctgaa caccggctcc ataagcggcg aggcgaacct gtacgctaat  600
gtgggtggcg tcgcttggcg cgtcagtccg ggttacccga acggcggcgg cgtgaacatc  660
ggcgccgtgt taactaagtg ccagcagaag ggctgggcga acttcagaaa tttccagcct  720
tccggccggg acgtcatcgt gaagggccag ggcaccttca cctcaaacta cgggacagac  780
tttatcctta agatcgagga catcaccgac agcaagctcc gaaacaacaa cggctccggc  840
accgtcgtgc aagagattaa ggtcccgctc attaggacgg agatctaa            888
```

```
SEQ ID NO: 44          moltype = DNA  length = 954
FEATURE                Location/Qualifiers
misc_feature           1..954
                       note = A synthetic nucleotide sequence encoding a TIC4346
                        protein designed for expression in plants.
source                 1..954
                       mol_type = other DNA
                       organism = synthetic construct
SEQUENCE: 44
atgaagaagt tcgcgagttt gatcctgatc agtgtgttcc tcttctcctc tacccagttc  60
gtgcacgcgt cctccaccga cgtgcaagag aggctgaggg acttggctcg agagaacgag  120
gccgggaccc tgaacgaggc gtggaacacg aatttcaagc cttccgatga gcaacagttc  180
tcctacagcc ctaccgaagg gattgtgttc ctcacgcctc ccaagaacgt gatcggcgag  240
cgccgcatct cgcagtacaa ggtgaacaac gcctgggcga cgctcgaggg ctcacccacc  300
gaggtctcgg gcactccgct gtacgccggc aagaacgtcc ttgacaactc caagggaacc  360
atggatcaag agctattgac gccggagttc aactacacgt acaccgagag caccagcaac  420
acgatcacac acggcctcaa gctaggcgtg aagacgactg cgacaatgaa gttcccgatc  480
gcacagggct cgatggaggc cagcacggag tacaacttcc agaactcgtc caccgacacg  540
aagactaagc aagtgtcata caagtctccc tcacagaaga taaaggtgcc ggccggcaag  600
acgtttcgcg tcctggccta cttaaacacg ggttccatta gcggtgaggc caacctctat  660
gcgaatgtgg gcggaattgc gtggggcgtc ctgcccggat acccgaacgg cggcggcgtc  720
aacatcggcg ccgtgttgac gaaatgtcag cagaagggct ggggcgattt ccgtaacttc  780
cagccgtccg gccgcgacgt gatagtgaag ggacagggaa cgttcgagtc aaactacggc  840
acagacttca tcttaaagat cgaagacata acagactcga agctgcgcaa caataacggc  900
tcaggcacgg tcgttcagga gattaaggtg cctctcatcc ggacagagat ctag        954
```

```
SEQ ID NO: 45          moltype = DNA  length = 888
FEATURE                Location/Qualifiers
misc_feature           1..888
                       note = A synthetic nucleotide sequence encoding a mature
                        TIC4346 protein, mTIC4346 designed for expression in
                        plants.
source                 1..888
                       mol_type = other DNA
                       organism = synthetic construct
SEQUENCE: 45
atgtcctcca ccgacgtgca agagaggctg agggacttgg ctcgagagaa cgaggccggg  60
accctgaacg aggcgtggaa cacgaatttc aagccttccg atgagcaaca gttctcctac  120
agccctaccg aagggattgt gttcctcacg cctcccaaga acgtgatcgg cgagcgccgg  180
atctcgcagt acaaggtgaa caacgcctgg gcgacgctcg agggctcacc caccgaggtc  240
tcgggcactc cgctgtacgc cggcaagaac gtccttgaca actccaaggg aaccatggat  300
caagagctat tgacgccgga gttcaactac acgtacaccg agagcaccag caacacgatc  360
acacacggcc tcaagctagg cgtgaagacg actgcgacaa tgaagttccc gatcgcacag  420
ggctcgatgg aggccagcac ggagtacaac ttccagaact cgtccaccga cacgaagact  480
aagcaagtgt catacaagtc tccctcacag aagataaagg tgccggccgg caagacgttt  540
cgcgtcctgg cctacttaaa cacgggttcc attagcggtg aggccaacct ctatgcgaat  600
gtgggcggaa ttgcgtgggg cgtcctgccc ggatacccga acggcggcgg cgtcaacatc  660
ggcgccgtgt tgacgaaatg tcagcagaag ggctggggcg atttccgtaa cttccagccg  720
tccggccgcg acgtgatagt gaagggacag ggaacgttcg agtcaaacta cggcacagac  780
ttcatcttaa agatcgaaga cataacagac tcgaagctgc gcaacaataa cggctcaggc  840
acggtcgttc aggagattaa ggtgcctctc atccggacag agatctag            888
```

```
SEQ ID NO: 46          moltype = DNA  length = 954
FEATURE                Location/Qualifiers
misc_feature           1..954
                       note = A synthetic nucleotide sequence encoding a TIC4826
                        protein designed for expression in plants.
source                 1..954
                       mol_type = other DNA
                       organism = synthetic construct
SEQUENCE: 46
atgaagaagt tcgcgagttt gatcctgatc agtgtgttcc tcttctcctc tacccagttc  60
gtgcacgcga gctcgacgga cgtccaggaa cggctccggg accttgcgcg cgagaacgag  120
gccgggacgt gaacgaggc ctggaacacc aacttcaaac cgagcgacga gcagcagttc  180
agctactctc ccacgggggg catagtcttc ctcacgcctc ccaagaacgt gatcggcgag  240
aggcgcatct cccagtacaa ggtgaacaac gcctgggcga ccttggaggg ctctcccacg  300
gaggtgtccg gcactccgct ctacgccggc aagaacgtct tagacaacag caaagggacc  360
atggatcaga gctattgac gccggagttc aattacacgt acaccgaaag tacaagtaat  420
acgaccactc atggcctgaa gctcggcgtg aagactcag caacaatgaa gtttcccatt  480
gcccagggt cgatggaggc ctcgaccgag tacaatttcc agaactcctc aacagacact  540
```

```
aagaccaaac aggtgtcgta caagagccct agccagaaga tcaaagtccc ggccggcaag  600
acctacaggg tgctggcgta cctcaacacc ggctctatct cgggcgaggc gaacctctac  660
gcgaacgtgg gcgggatcgc atggggtgtg ctacctggtt acccgaacgg aggcggcatc  720
aacatcggcg cggtgctgac aaagtgccag cagaaggggtt ggggcgactt cgcaacttc  780
cagccgaacg ggagagacgt catcgtgaag ggccagggca ccttcaagag caattacggc  840
acggacttca tcctcaagat tgaagacatc accgacagca agctgcgaaa taacaacggg  900
tcgggcaccg tcgtccagga gatcaaagtg ccgctcatcc ggaccgagat ctag         954
```

SEQ ID NO: 47    moltype = DNA length = 888
FEATURE       Location/Qualifiers
misc_feature     1..888
          note = A synthetic nucleotide sequence encoding a mature
          TIC4826 protein, mTIC4826 designed for expression in
          plants.
source        1..888
          mol_type = other DNA
          organism = synthetic construct
SEQUENCE: 47

```
atgagctcga cggacgtcca ggaacggctc cgggaccttg cgcgcgagaa cgaggccggg   60
acgttgaacg aggcctggaa caccaacttc aaaccgagcg acgagcagca gttcagctac  120
tctcccacgg agggcatagt cttcctcacg cctcccaaga acgtgatcgg cgagaggcgc  180
atctcccagt acaaggtgaa caacgcctgg gcgaccttgg agggctctcc cacggaggtg  240
tccggcactc cgctctacgc cggcaagaac gtcttagaca acagcaaagg gaccatggat  300
caggagctat tgacgccgga gttcaattac acgtacaccg aaagtacaag taatacgacc  360
actcatggcc tgaagctcgg cgtgaagact acagcaacaa tgaagtttcc cattgcccaa  420
gggtcgatgg aggcctcgac cgagtacaat ttccagaacc cctcaacaga cactaagacc  480
aaacaggtgt cgtacaagag ccctagccag aagatcaaag tcccggccgg caagacctac  540
agggtgctgg cgtacctcaa caccggctct atctcgggcg aggcgaacct ctacgcgaac  600
gtgggcggga tcgcatgggg tgtgctacct ggttacccga acgaggcggg catcaacatc  660
ggcgcggtgc tgacaaagtg ccagcagaag ggttggtggac actttcgcaa cttccagccg  720
agcgggagag acgtcatcgt gaagggccag ggcaccttca gagcaatta cggcacggac  780
ttcatcctca gattgaaga catcaccgac agcaagctgc gaaataacaa cgggtcgggc  840
accgtcgtcc aggagatcaa agtgccgctc atccggaccg agatctag              888
```

SEQ ID NO: 48    moltype = DNA length = 921
FEATURE       Location/Qualifiers
misc_feature     1..921
          note = A synthetic nucleotide sequence encoding a TIC4861
          protein designed for expression in plants.
source        1..921
          mol_type = other DNA
          organism = synthetic construct
SEQUENCE: 48

```
atgtttctgt tctcgagcac ccagtttgtg cacgcgtcct ccacggatgt gcaagagcgg   60
ctccgcgacc tagcccgcga gaacgaggct ggcacactga cgaggcgtg gaacacgaac  120
ttcaagccga gcgacgagca gcagttctcc tactcgccga ctgagggcat cgtcttcctg  180
acgcctccca agaacgtaat cggcgagcgg aggattagtc agtacaaggt gaacaatgcg  240
tgggcaacgc tcgagggtag cccaaccgag gtctccggca cgccgctcta cgcgggaaag  300
aacgtcctgg acaattccaa gggcaccagc gaccaggagc tgcttacgcc ggagtttaat  360
tacacctaca cagagtcgac ctcgaatacg acaacacacg gccttaagct gggcgttaag  420
acaacggcag cgatgaagtt tcccattgcc cagggttcag tggaagcttc tacggagtac  480
aactttcaga actcgagcac agacacaaag acgaagcaag tgtcctacaa gagccctagc  540
cagaagataa aggtccctgc cggcaagaca tacagggtct tagcgtacct caacaccggc  600
tcgatctcag gagaggccaa cctgtacgcc aacatcggcg ggatcgcctg gggtggcctc  660
ccgggctacc ctaacggcgg cggtgtgaac atcggcgctg tcctgacgaa atgccagcag  720
aaagggtggg gcgacttccg aaacttccag ccgagcgggc gcgacgttat cgtcaagggt  780
cagggcactt tcaagtctaa ttacggaacc gatttcattc tgaagatcga ggacattacc  840
gatagcaagc tccggaacaa caacggcagc ggtacggttg tccaggagat caaggtccct  900
ctgatacgaa cagagatttg a                                          921
```

SEQ ID NO: 49    moltype = DNA length = 888
FEATURE       Location/Qualifiers
misc_feature     1..888
          note = A synthetic nucleotide sequence encoding a mature
          TIC4861 protein, a mature TIC4862 protein, and a mature
          TIC4863 protein designed for expression in plants.
source        1..888
          mol_type = other DNA
          organism = synthetic construct
SEQUENCE: 49

```
atgtcctcca cggatgtgca agagcggctc cgcgacctag cccgcgagaa cgaggctggc   60
acactgaacg aggcgtggaa cacgaacttc aagccgagcg acgagcagca gttctcctac  120
tcgccgactg agggcatcgt cttcctgacg cctcccaaga acgtaatcgg cgagcggagg  180
attagtcagt acaaggtgaa caatgcgtgg gcaacgctcg agggtagccc aaccgaggtc  240
tccggcacgc cgctctacgc gggaaagaac gtcctggaca attccaaggg caccagcgac  300
caggagctgc ttacgccgga gtttaattac acctacacag agtcgacctc gaatacgaca  360
acacacggcc ttaagctggg cgttaagaca acggcgacga tgaagtttcc cattgcccag  420
ggttcgatgg aagcttctac ggagtacaac tttcagaact cgagcacaga cacaaagacg  480
aagcaagtgt cctacaagag ccctagccag aagataaaag tccctgccgg caagacatac  540
```

-continued

```
agggtcttag cgtacctcaa caccggctcg atctcaggag aggccaacct gtacgccaac  600
atcggcggga tcgcctgggg tggcctcccg ggctacccta acggcggcgg tgtgaacatc  660
ggcgctgtcc tgacgaaatg ccagcagaaa gggtgggcg acttccgaaa cttccagccg  720
agcgggcgcg acgttatcgt caagggtcag ggcactttca agtctaatta cggaaccgat  780
ttcattctga agatcgagga cattaccgat agcaagctcc ggaacaacaa cggcagcggt  840
acggttgtcc aggagatcaa ggtccctctg atacgaacag agatttga            888
```

```
SEQ ID NO: 50            moltype = DNA  length = 948
FEATURE                  Location/Qualifiers
misc_feature             1..948
                         note = A synthetic nucleotide sequence encoding a TIC4682
                          protein designed for expression in plants.
source                   1..948
                         mol_type = other DNA
                         organism = synthetic construct
SEQUENCE: 50
atgttcgcgt cgctcattct gatctccgtg tttctcttct cgtcgaccca gttcgtgcac  60
gcgtcctcca cggatgtgca agagcggctc cgcgacctag cccgcgagaa cgaggctggc  120
acactgaacg aggcgtggaa cacgaacttc aagccgagcg acgagcagca gttctcctac  180
tcgccgactg agggcatcgt cttcctgacg cctcccaaga acgtaatcgg cgagcggagg  240
attagtcagt acaaggtgaa caatgcgtgg gcaacgctcg agggtagccc aaccgaggtc  300
tccggcacgc cgctctacgc gggaaagaac gtcctgacaa attccaaggg caccagcgac  360
caggagctgc ttacgccgga gtttaattac acctacacag agtcgacctc gaatacgaca  420
acacacggcc ttaagctggg cgttaagaca acggcgacga tgaagtttcc cattgcccag  480
ggttcgatgg aagcttctac ggagtacaac tttcagaact cgagcacaga cacaaagacg  540
aagcaagtgt cctacaagag ccctagccag aagataaagg tccctgccgg caagacatac  600
agggtcttag cgtacctcaa caccggctcg atctcaggag aggccaacct gtacgccaac  660
atcggcggga tcgcctgggg tggcctcccg ggctacccta acggcggcgg tgtgaacatc  720
ggcgctgtcc tgacgaaatg ccagcagaaa gggtgggcg acttccgaaa cttccagccg  780
agcgggcgcg acgttatcgt caagggtcag ggcactttca agtctaatta cggaaccgat  840
ttcattctga agatcgagga cattaccgat agcaagctcc ggaacaacaa cggcagcggt  900
acggttgtcc aggagatcaa ggtccctctg atacgaacag agatttga            948
```

```
SEQ ID NO: 51            moltype = DNA  length = 954
FEATURE                  Location/Qualifiers
misc_feature             1..954
                         note = A synthetic nucleotide sequence encoding a TIC4863
                          protein designed for expression in plants.
source                   1..954
                         mol_type = other DNA
                         organism = synthetic construct
SEQUENCE: 51
atgaagaagt tcgcgagttt gatcctgatc agtgtgttcc tcttctcctc tacccagttc  60
gtgcacgcgt cctccacgga tgtgcaagag cggctccgcg acctagcccg cgagaacgag  120
gctggcacac tgaacgaggc gtggaacacg aacttcaagc cgagcgacga gcagcagttc  180
tcctactcgc cgactgaggg catcgtcttc ctgacgcctc ccaagaacgt aatcggcgag  240
cggaggatta gtcagtacaa ggtgaacaat gcgtgggcaa cgctcgaggg tagcccaacc  300
gaggtctccg gcacgccgct ctacgcggga aagaacgtcc tggacaattc caagggcacc  360
agcgaccagg agctgcttac gccggagttt aattacacct acacagagtc gacctcgaat  420
acgacaacac acggccttaa gctgggcgtt aagacaacgg cgacgatgaa gtttcccatt  480
gcccagggt cgatggaagc ttctacggag tacaactttc agaactcgag cacagacaca  540
aagacgaagc aagtgtccta caagagccct agccagaaga taaaggtccc tgccggcaag  600
acatacaggg tcttagcgta cctcaacacc ggctcgatct caggagaggc caacctgtac  660
gccaacatcg gcgggatcgc ctggggtggc ctcccgggct accctaacgg cggcggtgtg  720
aacatcggcg ctgtcctgac gaaatgccag cagaaagggt ggggcgactt ccgaaacttc  780
cagccgagcg ggcgcgacgt tatcgtcaag ggtcagggca ctttcaagtc taattacgga  840
accgatttca ttctgaagat cgaggacatt accgatagca agctccggaa caacaacggc  900
agcggtacgt tgtccaggga tcaaggtc cctctgatac gaacagagat ttga        954
```

```
SEQ ID NO: 52            moltype = DNA  length = 36
FEATURE                  Location/Qualifiers
misc_feature             1..36
                         note = A nucleotide sequence representing a synthetic
                          oligonucleotide for hybridizing to the (-) strand of a DNA
                          encoding a protein disclosed in this application and
                          corresponds to positions 1 to 36 of SEQ ID NO:1 (TIC3668
                          forward primer).
source                   1..36
                         mol_type = other DNA
                         organism = synthetic construct
SEQUENCE: 52
atgaaaaaat ttgcaagttt aattcttaca agtgtg                            36
```

```
SEQ ID NO: 53            moltype = DNA  length = 34
FEATURE                  Location/Qualifiers
misc_feature             1..34
                         note = A nucleotide sequence representing a synthetic
                          oligonucleotide for hybridizing to the (+) strand of a DNA
                          encoding a protein disclosed in this application and
```

-continued

```
                              corresponds to positions 920 to 954 of SEQ ID NO:1
                              (TIC3668 reverse primer).
source                        1..34
                              mol_type = other DNA
                              organism = synthetic construct
SEQUENCE: 53
ctatatttca gttctaatta gtggaacttt aatc                                34

SEQ ID NO: 54                 moltype = DNA  length = 41
FEATURE                       Location/Qualifiers
misc_feature                  1..41
                              note = A nucleotide sequence representing a synthetic
                              oligonucleotide for hybridizing to the (-) strand of a DNA
                              encoding a protein disclosed in this application and
                              corresponds to positions 1 to 41 of SEQ ID NO:3 (TIC3669
                              forward primer).
source                        1..41
                              mol_type = other DNA
                              organism = synthetic construct
SEQUENCE: 54
atgaaaaaat ttgcaagttt aattcttata agtgtgttcc t                        41

SEQ ID NO: 55                 moltype = DNA  length = 34
FEATURE                       Location/Qualifiers
misc_feature                  1..34
                              note = A nucleotide sequence representing a synthetic
                              oligonucleotide for hybridizing to the (+) strand of a DNA
                              encoding a protein disclosed in this application and
                              corresponds to positions 920 to 954 of SEQ ID NO:3
                              (TIC3669 reverse primer).
source                        1..34
                              mol_type = other DNA
                              organism = synthetic construct
SEQUENCE: 55
ctatatttca gttctaatta gtggaacttt aatc                                34

SEQ ID NO: 56                 moltype = DNA  length = 36
FEATURE                       Location/Qualifiers
misc_feature                  1..36
                              note = A nucleotide sequence representing a synthetic
                              oligonucleotide for hybridizing to the (-) strand of a DNA
                              encoding a protein disclosed in this application and
                              corresponds to positions 1 to 36 of SEQ ID NO:5 (TIC3670
                              forward primer).
source                        1..36
                              mol_type = other DNA
                              organism = synthetic construct
SEQUENCE: 56
atgaaaaaat ttgcaagttt aattcttaca agtgtg                              36

SEQ ID NO: 57                 moltype = DNA  length = 34
FEATURE                       Location/Qualifiers
misc_feature                  1..34
                              note = A nucleotide sequence representing a synthetic
                              oligonucleotide for hybridizing to the (+) strand of a DNA
                              encoding a protein disclosed in this application and
                              corresponds to positions 920 to 954 of SEQ ID NO:5
                              (TIC3670 reverse primer).
source                        1..34
                              mol_type = other DNA
                              organism = synthetic construct
SEQUENCE: 57
ctatatttca gttctaatta gtggaacttt aatc                                34

SEQ ID NO: 58                 moltype = DNA  length = 41
FEATURE                       Location/Qualifiers
misc_feature                  1..41
                              note = A nucleotide sequence representing a synthetic
                              oligonucleotide for hybridizing to the (-) strand of a DNA
                              encoding a protein disclosed in this application and
                              corresponds to positions 1 to 41 of SEQ ID NO:7 (TIC4076
                              forward primer).
source                        1..41
                              mol_type = other DNA
                              organism = synthetic construct
SEQUENCE: 58
atgaaaaaat ttgcaagttt aattcttata agtgtgttcc t                        41

SEQ ID NO: 59                 moltype = DNA  length = 34
```

```
FEATURE            Location/Qualifiers
misc_feature       1..34
                   note = A nucleotide sequence representing a synthetic
                   oligonucleotide for hybridizing to the (+) strand of a DNA
                   encoding a protein disclosed in this application and
                   corresponds to positions 920 to 954 of SEQ ID NO:7
                   (TIC4076 reverse primer).
source             1..34
                   mol_type = other DNA
                   organism = synthetic construct
SEQUENCE: 59
ctatatttca gttctaatta gtggaacttt aatc                              34

SEQ ID NO: 60      moltype = DNA  length = 36
FEATURE            Location/Qualifiers
misc_feature       1..36
                   note = A nucleotide sequence representing a synthetic
                   oligonucleotide for hybridizing to the (-) strand of a DNA
                   encoding a protein disclosed in this application and
                   corresponds to positions 1 to 36 of SEQ ID NO:9 (TIC4078
                   forward primer).
source             1..36
                   mol_type = other DNA
                   organism = synthetic construct
SEQUENCE: 60
atgaaaaaat ttgcaagttt aattcttaca agtgtg                            36

SEQ ID NO: 61      moltype = DNA  length = 34
FEATURE            Location/Qualifiers
misc_feature       1..34
                   note = A nucleotide sequence representing a synthetic
                   oligonucleotide for hybridizing to the (+) strand of a DNA
                   encoding a protein disclosed in this application and
                   corresponds to positions 920 to 954 of SEQ ID NO:9
                   (TIC4078 reverse primer).
source             1..34
                   mol_type = other DNA
                   organism = synthetic construct
SEQUENCE: 61
ctatatttca gttctaatta gtggaacttt aatc                              34

SEQ ID NO: 62      moltype = DNA  length = 954
FEATURE            Location/Qualifiers
misc_feature       1..954
                   note = A recombinant polynucleotide sequence obtained from
                   a Brevibacillus laterosporus species encoding a TIC2462
                   protein from an open reading frame at nucleotide position
                   1-951 and a translation termination codon.
source             1..954
                   mol_type = other DNA
                   organism = Brevibacillus laterosporus
SEQUENCE: 62
atgaaaaaat ttgcaagttt aattcttata agtgtgttcc ttttttcgag tacgcaattt   60
gttcatgcgt catccataga tgttcaagaa agattacggg acttggcaag agaaaatgaa  120
gctggaaccc ttaatgaagc atggaatact aacttcaaac ccagtgatga acaacaattc  180
tcttatagtc caactgaagg tattgttttc ttaacaccac ctaaaaatgt tattggcgaa  240
agaagaattt cacagtataa agtaaataat gcatgggcta cattagaagg aagtccaacc  300
gaagtatcgg ggacacctt atatgcggga aaaaacgtat tagataactc aaaaggaaca  360
agcgatcaag agctgttaac acccgagttt aactatacct atacggaaag cacttcaaat  420
acaacaactc atggattaaa attaggagtc aaaaccactg ctaccatgaa attcccgatt  480
gctcagggta gcatggaagc ttctactgaa tataactttc aagattcttc cactgatact  540
acaactaaaa cagtatcata taaaagccca tcacaaaaga ttaaagtacc agcaggtaaa  600
acctttagag ttttagcata cctaaatact ggatctattt caggtgaagc taacctttac  660
gcaaatgttg ggggtatagc ttggggagtt ttaccaggtt atcccaatgg cggaggagta  720
aatataggtg ctgtacttac caaatgccaa caaaaaggat ggggagattt cagaaacttt  780
caacctagtg gaagagatgt aatcgttaaa ggccaaggta ctttcaaatc taattatgga  840
acggacttca ttttaaaaat tgaagacatc acagattcaa agttacgaaa caataacggg  900
agtggaactg tcgttcaaga gattaaagtt ccactaatta gaactgaaat atag         954

SEQ ID NO: 63      moltype = AA  length = 317
FEATURE            Location/Qualifiers
REGION             1..317
                   note = The amino acid sequence translation of the TIC3462
                   protein open reading frame as set forth in SEQ ID NO:62.
source             1..317
                   mol_type = protein
                   organism = Brevibacillus laterosporus
SEQUENCE: 63
MKKFASLILI SVFLFSSTQF VHASSIDVQE RLRDLARENE AGTLNEAWNT NFKPSDEQQF   60
```

```
SYSPTEGIVF LTPPKNVIGE RRISQYKVNN AWATLEGSPT EVSGTPLYAG KNVLDNSKGT   120
SDQELLTPEF NYTYTESTSN TTTHGLKLGV KTTATMKFPI AQGSMEASTE YNFQDSSTDT   180
TTKTVSYKSP SQKIKVPAGK TFRVLAYLNT GSISGEANLY ANVGGIAWGV LPGYPNGGGV   240
NIGAVLTKCQ QKGWGDFRNF QPSGRDVIVK GQGTFKSNYG TDFILKIEDI TDSKLRNNNG   300
SGTVVQEIKV PLIRTEI                                                   317

SEQ ID NO: 64            moltype = DNA  length = 888
FEATURE                  Location/Qualifiers
misc_feature             1..888
                         note = A synthetic nucleotide sequence encoding a mature
                         TIC3668 protein, mTIC3668 for expression in bacteria.
source                   1..888
                         mol_type = other DNA
                         organism = synthetic construct
SEQUENCE: 64
atgtcatcca cagatgttca agaaagatta cgggacttgg caagagaaga tgaagctgga   60
acctttaatg aagcatggaa tactaacttc aaacccagtg atgaacaaca attctcgtat   120
agtccaactg aaggaattgt tttcttaaca ccacctaaaa atgttattgg cgaaagaaga   180
atttcacagt ataaagtaaa taatgcatgg gctacattag taggaagtcc aaccgaagca   240
tcggggacac ctttatatgc gggaaaaaac gtattagata actcaaaagg aacaatggat   300
caagagctgt taacacccga gtttaactat acctatacgg aaagcacttc aaatacaata   360
actcatggat taaaattagg agtcaaaacc actgctacca tgaaattccc gattgctcag   420
ggtagcatgg aagcttctac tgaatataac tttcaaaatt cttccactga tactaaaact   480
aaacaagtat catataaaag cccatcacaa aaaattaaag taccagcagg taaaacctat   540
agagtttttag catacctaaa tactggatct atttcaggtg aagctaacct ttacgcaaat   600
gttgggggta tagcttggag ggtttcacca ggttatccca atggcggagg agtaaatata   660
ggtgctgtac ttaccaaatg ccaacaaaaa ggatggggag atttcagaaa ctttcaacct   720
agtggaagag atgtaatcgt taaaggccaa ggtactttca aatctaatta tggaacggac   780
ttcattttaa aaattgaaga catcacagat tcaaagttac gaaacaataa cgggagtgga   840
actgtcgttc aagagattaa agttccacta attagaactg aaatatag              888

SEQ ID NO: 65            moltype = DNA  length = 888
FEATURE                  Location/Qualifiers
misc_feature             1..888
                         note = A synthetic nucleotide sequence encoding a mature
                         TIC3669 protein, mTIC3669 for expression in bacteria.
source                   1..888
                         mol_type = other DNA
                         organism = synthetic construct
SEQUENCE: 65
atgtcatcca cagatgttca agaaagatta cgggacttgg caagagaaga tgaagctgga   60
acctttaatg aagcatggaa tactaacttc aaacccagtg atgaacaaca attctcgtat   120
agtccaactg aaggaattgt tttcttaaca ccacctaaaa atgttattgg cgaaagaaga   180
atttcacagt ataaagtaaa taatgcatgg gctacattag aaggaagtcc aaccgaagta   240
tcggggacac ctttatatgc gggaaaaaac gtattagata actcaaaagg aacaatcgat   300
caagagctgt taacacccga gtttagttat acctatacgg aaagcacttc aaatacaaca   360
actcatggat taaaagtagg agtcaaaacc actgctacca tgaaattccc gattgctcag   420
ggtagcatgg aagcttctac tgaatataac tttcaaaatt cttccactga tactaaaact   480
aaacaagtat catataaaag cccatcacaa aaaattaaag taccagcagg taaaacctat   540
agagtttttag catacctaaa tactggatct atttcaggtg aagctaacct ttacgcaaat   600
gttgggggta tagcttggag ggtttcacca ggttatccca atggcggagg agtaaatata   660
ggtgctgtac ttaccaaatg ccaacaaaaa ggatggggag atttcagaaa ctttcaacct   720
agtggaagag atgtaatcgt taaaggccaa ggtactttca aatctaatta tggaacggac   780
ttcattttaa aaattgaaga catcacagat tcaaagttac gaaacaataa cgggagtgga   840
actgtcgttc aagagattaa agttccacta attagaactg aaatatag              888

SEQ ID NO: 66            moltype = DNA  length = 888
FEATURE                  Location/Qualifiers
misc_feature             1..888
                         note = A synthetic nucleotide sequence encoding a mature
                         TIC3670 protein, mTIC3670 for expression in bacteria.
source                   1..888
                         mol_type = other DNA
                         organism = synthetic construct
SEQUENCE: 66
atgtcatcca cagatgttca agaaagatta cgggacttgg caagagaaga tgaagctgga   60
acctttaatg aagcatggaa tactaacttc aaacccagtg atgaacaaca attctcttat   120
agtccaactg aaggaattgt tttcttaaca ccacctaaaa atgttattgg cgaaagaaga   180
atttcacagt ataaagtaaa taatgcatgg gctacattag aaggaagtcc aaccgaagca   240
tcggggacac ctttatatgc gggaaaaaac gtattagata actcaaaagg aacaatggat   300
caagagctgt taacacccga gtttaactat acctatacgg aaagcacttc aaatacaaca   360
acccatggat taaaattagg agtcaaaacc actgctacca tgaaattccc gattgctcag   420
ggtagcatgg aagcttctac tgaatataac tttcaaaatt cttccactga tactaaaact   480
aaacaagtat catataaaag cccatcacaa aaaattaaag taccagcagg taaaacctat   540
agagtttttag catacctaaa tactggatct atttcaggtg aagctaacct ttacgcaaat   600
gttgggggta tagcttggag ggtttcacca ggttatccca atggcggagg agtaaatata   660
ggtgctgtac ttaccaaatg ccaacaaaaa ggatggggag atttcagaaa ctttcaacct   720
agtggaagag atgtaatcgt taaaggccaa ggtactttca aatctaatta tggaacggac   780
ttcattttaa aaattgaaga catcacagat tcaaagttac gaaacaataa cgggagtgga   840
```

-continued

```
actgtcgttc aagagattaa agttccacta attagaactg aaatatag              888

SEQ ID NO: 67          moltype = DNA  length = 888
FEATURE                Location/Qualifiers
misc_feature           1..888
                       note = A synthetic nucleotide sequence encoding a mature
                        TIC4076 protein, mTIC4076 for expression in bacteria.
source                 1..888
                       mol_type = other DNA
                       organism = synthetic construct
SEQUENCE: 67
atgtcatcca cagatgttca agaaagatta cgggacttgg caagagaaaa tgaagctgga    60
acccttaatg aagcatggaa tactaacttc aaacccagtg atgaacaaca attctcttat   120
agtccaactg aaggtattgt tttcttaaca ccacctaaaa atgttattgg cgaaagaaga   180
atttcacagt ataaagtaaa taatgcatgg gctacattag aaggaagtcc aaccgaaatg   240
tcggggacac ctttatatgc gggaaaaaac gtattagata actcaaaagg aacaagcgat   300
caagagctgt taacacccga gtttacctat acctatacgg aaagcacttc aaatacaaca   360
actcatggat taaaattagg agtcaaaacc actgctacca tgaaattccc gattgctcag   420
ggtagcatgg aagcttctac tgaatataac tttcaaaatt cttccactga tactaaaact   480
aaacaagtat catataaaag cccatcacaa aagattaaag taccagcagg taaaaccttt   540
agagtttttg catacctaaa tactggatct atttcaggtg aagctaacct ttacgcaaat   600
gttgggggta tagcttgggg ggtttacca ggttatccca atggcggagg agtaaatata   660
ggtgctgtac ttaccaaatg ccaacaaaaa ggatggggag atttcagaaa ctttcaacct   720
agtgaaagag atgtaatcgt taaaggccaa ggtactttca catctaatta tggaacggac   780
ttcattttaa aaattgaaga catcacagat tcaaagttac gaaacaataa cgggagtgga   840
actgtcgttc aagagattaa agttccacta attagaactg aaatatag              888

SEQ ID NO: 68          moltype = DNA  length = 888
FEATURE                Location/Qualifiers
misc_feature           1..888
                       note = A synthetic nucleotide sequence encoding a mature
                        TIC4078 protein, mTIC4078 for expression in bacteria.
source                 1..888
                       mol_type = other DNA
                       organism = synthetic construct
SEQUENCE: 68
atgtcatcca cagatgttca agaaagatta cgggacttgg caagagaaaa tgaagctgga    60
acccttaatg tagcatggaa tactaacttc aaacccagtg atgaacaaca attctcttat   120
agtccaactg aaggttttat tttcttaaca ccacctaaaa atgttattgg cgaaagaaga   180
atttcacatt ataaagtaaa taatgcatgg gctacattag aaggaagtcc aaccgaagta   240
tcggggacac ctttatatgc gggaagaaac gtattagata actcaaaagg aacaatagat   300
caagagatgt taacacccga gtttaactat acctatacgg aaggcacttc aaatacaaca   360
actcatggat taaaattagg agtcaaaacc actgctacca tgaaattccc gattgctcag   420
ggtagcatgg aagcttctac tgaatataac tttcaaaatt cttccactga tactaaaact   480
aaacaagtat catataaaag cccatcacaa aaaattaaag taccagcagg taaaacctttt   540
agagtttttg catacctaaa tactggatct atttcaggtg aagctaacct ttacgcaaat   600
gttgggggta tagcttgggg ggtttttacca ggttatccca atggcggagg agtaaatata   660
ggtgctgtac ttaccaaatg ccaacaaaaa ggatggggag atttcagaaa ctttcaacct   720
agtgaaagag atgtaatcgt taaaggccaa ggtactttca catctaatta tggaacggac   780
ttcattttaa aaattgaaga catcacagat tcaaagttac gaaacaataa cgggagtgga   840
actgtcgttc aagagattaa agttccacta attagaactg aaatatag              888

SEQ ID NO: 69          moltype = DNA  length = 888
FEATURE                Location/Qualifiers
misc_feature           1..888
                       note = A synthetic nucleotide sequence encoding a mature
                        TIC4260 protein, mTIC4260 for expression in bacteria.
source                 1..888
                       mol_type = other DNA
                       organism = synthetic construct
SEQUENCE: 69
atgtcatcca tagatgttca agaaagatta cgggacttgg caagagaaga tgaagctgga    60
accttttaatg tagcatggaa tactaacttc aaacccagtg atgaacaaca attctcgtat   120
agtccaactg aaggttttat tttcttaaca ccacctaaaa atgttattgg cgaaagaaga   180
atttcacatt ataaagtaaa taatgcatgg gctacattag taggaagtcc aaccgaagca   240
tcggggacac ctttatatgc gggaagaaac gtattagata actcaaaagg aacaatggat   300
caagagatgt taacacccga gtttagttat acctatacgg aaggcacttc aaatacaata   360
actcatggat taaaagtagg agtcaaaacc actgctacca tgaaattccc gattgctcag   420
ggtagcatgg aagcttctac tgaatataac tttcaaaatt cttccactga tactaaaact   480
aaacaagtat catataaaag cccatcacaa aaaattaaag taccagcagg taaaacctat   540
agagttttag catacctaaa tactggatct atttcaggtg aagctaacct ttacgcaaat   600
gttgggggta tagcttggag ggtttcacca ggttatccca atggcggagg agtaaatata   660
ggtgctgtat ttaccaaatg ccaacaaaaa ggatggggag atttcagaaa ctttcaacct   720
agtgaaagag atgtaatcgt taaaggccaa ggtactttca catctaatta tggaacggac   780
ttcattttaa aaattgaaga catcacagat tcaaagttac gaaacaataa cgggagtgga   840
actgtcgttc aagagattaa agttccacta attagaactg aaatatag              888

SEQ ID NO: 70          moltype = DNA  length = 888
FEATURE                Location/Qualifiers
```

```
misc_feature            1..888
                        note = A synthetic nucleotide sequence encoding a mature
                        TIC4346 protein, mTIC4346 for expression in bacteria.
source                  1..888
                        mol_type = other DNA
                        organism = synthetic construct
SEQUENCE: 70
atgtcatcca cagatgttca agaaagatta cgggacttag caagagaaaa tgaagctgga    60
acccttaatg aagcatggaa tactaacttc aaacccagtg atgaacaaca attctcttat   120
agtccaactg aaggaattgt tttcttaaca ccacctaaaa atgttattgg cgaaagaaga   180
atttcacagt ataaagtaaa taatgcatgg gctacattag aaggaagtcc aaccgaagta   240
tcggggacac ctttatatgc gggaaaaaac gtattagata actcaaaagg aacaatggat   300
caagagctgt taacacccga gtttaactat acctatacgg aaagcacttc aaatacaata   360
actcatggat taaaattagg agtcaaaacc actgctacca tgaaattccc gattgctcag   420
ggtagcatgg aagcttctac tgaatataac tttcaaaatt cttccactga tactaaaact   480
aaacaagtat catataaaag cccatcacaa aaaattaaag taccagcagg taaaacctt    540
agagtttttag catacctaaa tactggatct atttcaggtg aagctaacct ttacgcaaat   600
gttgggggta tagcttgggg ggtttacca ggttatccca atggcggagg agtaaatata   660
ggtgctgtac ttaccaaatg ccaacaaaaa ggatggggag atttcagaaa ctttcaacct   720
agtggaagag atgtaatcgt taaaggccaa ggtactttcg aatctaatta tggaacggac   780
ttcatttaa aaaattgaaga catcacagat tcaaagttac gaaacaataa cgggagtgga   840
actgtcgttc aagagattaa agttccacta attagaactg aaatatag                888

SEQ ID NO: 71             moltype = DNA  length = 888
FEATURE                   Location/Qualifiers
misc_feature              1..888
                          note = A synthetic nucleotide sequence encoding a mature
                          TIC4826 protein, mTIC4826 for expression in bacteria.
source                    1..888
                          mol_type = other DNA
                          organism = synthetic construct
SEQUENCE: 71
atgtcatcca cagatgttca agaaagatta cgggacttgg caagagaaaa tgaagctgga    60
acccttaatg aagcatggaa tactaacttc aaacccagtg atgaacaaca attctcttat   120
agtccactg aaggtattgt tttcttaaca ccacctaaaa atgttattgg cgaaagaaga    180
atttcacagt ataaagtaaa taatgcatgg gctacattag aaggaagtcc aaccgaagta   240
tcggggacac ctttatatgc gggaaaaaac gtattagata actcaaaagg aacaatggat   300
caagagctgt taacacccga gtttaactat acctatacgg aaagcacttc aaatacaaca   360
actcatggat taaaattagg agtcaaaacc actgctacca tgaaattccc gattgctcag   420
ggtagcatgg aagcttctac tgaatataac tttcaaaatt cttccactga tactaaaact   480
aaacaagtat catataaaag cccatcacaa aaaattaaag taccagcagg taaaacctat   540
agagtttttag catacctaaa tactggatct atatcaggtg aagctaacct ttacgcaaat   600
gttggggggta tagcttgggg ggtttacca ggttatccca atggcggagg aataaatata   660
ggtgctgtac ttaccaaatg ccaacaaaaa ggatggggag atttcagaaa ctttcaacct   720
agtggaagag atgtaatcgt taaaggccaa ggtactttca aatctaatta tggaacggac   780
ttcatttaa aaaattgaaga catcacagat tcaaagttac gaaacaataa cgggagtgga   840
actgtcgttc aagagattaa agttccacta attagaactg aaatatag                888

SEQ ID NO: 72             moltype = DNA  length = 888
FEATURE                   Location/Qualifiers
misc_feature              1..888
                          note = A synthetic nucleotide sequence encoding a mature
                          TIC4861 protein, a mature TIC4862 protein, and a mature
                          TIC4863 protein for expression in bacteria.
source                    1..888
                          mol_type = other DNA
                          organism = synthetic construct
SEQUENCE: 72
atgtcatcca cagatgttca agaacgatta cgggacttgg caagagaaaa tgaagctgga    60
acccttaatg aagcatggaa tactaacttc aaacccagtg atgaacaaca attctcttat   120
agtccaactg aaggtattgt tttcttaaca ccacctaaaa atgttattgg cgaaagaaga   180
atttcacagt ataaagtaaa taatgcatgg gctacattag aaggaagtcc aaccgaagta   240
tcggggacac ctttatatgc gggaaaaaac gtattagata actcaaaagg gacaagcgat   300
caagagctgt taacacccga gtttaactat acctatacgg aaagcacttc aaatacaaca   360
actcatggat taaaattagg agtcaaaacc actgctacca tgaaattccc gattgctcag   420
ggtagcatgg aagcttctac tgaatataac tttcaaaatt cttccactga tactaaaact   480
aaacaagtat catataaaag cccatcacaa aaaattaaag taccagcagg taaaacctat   540
agagtttttag catacctaaa tactggatct atttcaggtg aagctaacct ttacgcaaat   600
attggggggta tagcttgggg gggtttacca ggttatccca atggcggagg agtaaatata   660
ggtgctgtac ttaccaaatg ccaacaaaaa ggatggggag atttcagaaa ctttcaacct   720
agtggaagag atgtaatcgt taaaggccaa ggtactttca aatctaatta tggaacggac   780
ttcatttaa aaaattgaaga catcacagat tcaaagttac gaaacaataa cgggagtgga   840
actgtcgttc aagagattaa agttccacta attagaactg aaatatag                888

SEQ ID NO: 73             moltype = DNA  length = 954
FEATURE                   Location/Qualifiers
misc_feature              1..954
                          note = A recombinant polynucleotide sequence obtained from
                          a Brevibacillus laterosporus species encoding a TIC11239
```

```
                             precursor protein from an open reading frame at nucleotide
                             position 1-951 and a translation termination codon.
source                       1..954
                             mol_type = other DNA
                             organism = Brevibacillus laterosporus
SEQUENCE: 73
atgaaaaaat ttgcaagttt aattcttata agtgtgttcc ttttttcgag tacccaattt  60
gttcatgcgt catccacaga tgttcaagaa agattacggg acttggcaag agaagatgaa  120
gctggaacct ttaatgaagc atggaatact aacttcaaac ccagtgatga acaacaattc  180
tcttatagtc caactgaagg aattgttttc ttaacaccac ctaaaaatgt tattggcgaa  240
agaagaattt cacagtataa agtaaataat gcatgggcta cattagaagg aagtccaacc  300
gaagtatcgg ggacaccttt atatgcggga aaaaacgtat tagataactc aaaaggaaca  360
atggatcaag agctgttaac acccgagttt aactatacct atacggaaag cacttcaaat  420
acaataactc atggattaaa attaggagtc aaaaccactg ctaccatgaa attcccgatt  480
gctcagggta gcatggaagc ttctactgaa tataactttc aaaattcttc cactgatact  540
aaaactaaac aagtatcata taaaagccca tcacaaaaaa ttaaagtacc agcaggtaaa  600
acctatagag ttttagcata cctaaatact ggatctattt caggtgaagc taacctttac  660
gcaaatgttg ggggtatagc ttggagggtt tcaccaggtt atcccaatgg cggaggagta  720
aatataggtg ctgtacttac caaatgccaa caaaaaggat ggggagattt cagaaacttt  780
caacctagtg gaagagatgt aatcgttaaa ggccaaggta ctttcgaatc taattatgga  840
acggacttca ttttaaaaat tgaagacatc acagattcaa agttacgaaa caataacggg  900
agtggaactg tcgttcaaga gattaaagtt ccactaatta gaactgaaat atag          954

SEQ ID NO: 74            moltype = AA   length = 317
FEATURE                  Location/Qualifiers
REGION                   1..317
                         note = The amino acid sequence translation of the TIC11239
                          precursor protein from the open reading frame as set forth
                          in SEQ ID NO:73.
source                   1..317
                         mol_type = protein
                         organism = Brevibacillus laterosporus
SEQUENCE: 74
MKKFASLILI SVFLFSSTQF VHASSTDVQE RLRDLAREDE AGTFNEAWNT NFKPSDEQQF  60
SYSPTEGIVF LTPPKNVIGE RRISQYKVNN AWATLEGSPT EVSGTPLYAG KNVLDNSKGT  120
MDQELLTPEF NYTYTESTSN TITHGLKLGV KTTATMKFPI AQGSMEASTE YNFQNSSTDT  180
KTKQVSYKSP SQKIKVPAGK TYRVLAYLNT GSISGEANLY ANVGGIAWRV SPGYPNGGGV  240
NIGAVLTKCQ QKGWGDFRNF QPSGRDVIVK GQGTFESNYG TDFILKIEDI TDSKLRNNNG  300
SGTVVQEIKV PLIRTEI                                                  317

SEQ ID NO: 75            moltype = DNA   length = 954
FEATURE                  Location/Qualifiers
misc_feature             1..954
                         note = A recombinant polynucleotide sequence obtained from
                          a Brevibacillus laterosporus species encoding a TIC11243
                          precursor protein from an open reading frame at nucleotide
                          position 1-951 and a translation termination codon.
source                   1..954
                         mol_type = other DNA
                         organism = Brevibacillus laterosporus
SEQUENCE: 75
atgaaaaaat ttgcaagttt aattcttaca agtgtgttcc ttttttcgag tacccaattt  60
gttcatgcgt catccacaga tgttcaagaa agattacggg acttggcaag agaagatgaa  120
gctggaacct ttaatgaagc atggaatact aacttcaaac ccagtgatga acaacaattc  180
tcgtatagtc caactgaagg aattgttttc ttaacaccac ctaaaaatgt tattggcgaa  240
agaagaattt cacagtataa agtaaataat gcatgggcta cattagaagg aagtccaacc  300
gaagcatcgg ggacaccttt atatgcggga aaaaacgtat tagataactc aaaaggaaca  360
atggatcaag agctgttaac acccgagttt agttatacct atacggaaag cacttcaaat  420
acaacaaccc atggattaaa attaggagtc aaaaccactg ctaccatgaa attcccgatt  480
gctcagggta gcatggaagc ttctactgaa tataactttc aaaattcttc cactgatact  540
aaaactaaac aagtatcata taaaagccca tcacaaaaaa ttaaagtacc agcaggtaaa  600
acctatagag ttttagcata cctaaatact ggatctattt caggtgaagc taacctttac  660
gcaaatgttg gggtatagc ttggagggtt tcaccaggtt atcccaatgg cggaggagta  720
aatataggtg ctgtacttac caaatgccaa caaaaaggat ggggagattt cagaaacttt  780
caacctagtg gaagagatgt aatcgttaaa ggccaaggta ctttcaaatc taattatgga  840
acggacttca ttttaaaaat tgaagacatc acagattcaa aattacgaaa caataacggg  900
agtggaactg tcgttcaaga gattaaagtt ccactaatta gaactgaaat atag          954

SEQ ID NO: 76            moltype = AA   length = 317
FEATURE                  Location/Qualifiers
REGION                   1..317
                         note = The amino acid sequence translation of the TIC11243
                          precursor protein from the open reading frame as set forth
                          in SEQ ID NO:75.
source                   1..317
                         mol_type = protein
                         organism = Brevibacillus laterosporus
SEQUENCE: 76
MKKFASLILT SVFLFSSTQF VHASSTDVQE RLRDLAREDE AGTFNEAWNT NFKPSDEQQF  60
```

```
SYSPTEGIVF LTPPKNVIGE RRISQYKVNN AWATLEGSPT EASGTPLYAG KNVLDNSKGT   120
MDQELLTPEF SYTYTESTSN TTTHGLKLGV KTTATMKFPI AQGSMEASTE YNFQNSSTDT   180
KTKQVSYKSP SQKIKVPAGK TYRVLAYLNT GSISGEANLY ANVGGIAWRV SPGYPNGGGV   240
NIGAVLTKCQ QKGWGDFRNF QPSGRDVIVK GQGTFKSNYG TDFILKIEDI TDSKLRNNNG   300
SGTVVQEIKV PLIRTEI                                                  317

SEQ ID NO: 77          moltype = DNA   length = 954
FEATURE                Location/Qualifiers
misc_feature           1..954
                       note = A recombinant polynucleotide sequence obtained from
                       a Brevibacillus laterosporus species encoding a TIC11256
                       precursor protein from an open reading frame at nucleotide
                       position 1-951 and a translation termination codon.
source                 1..954
                       mol_type = other DNA
                       organism = Brevibacillus laterosporus
SEQUENCE: 77
atgaaaaaat ttgcaagttt aattcttaca agtgtgttcc ttttttcgag tacgcaattt   60
gttcatgcgt catccacaga tgttcaagaa agattacggg acttggcaag agaagatgaa   120
gctggaacct ttaatgaagc atggaatact aacttcaaac ccagtgatga acaacaattc   180
tcttatagtc caactgaagg aattgttttc ttaacaccac ctaaaaatgt tattggcgaa   240
agaagaattt cacagtataa agtaaataat gcatggaagg aagtccaacc   300
gaaatgtcgg ggacaccttt atatgcggga aaaaacgtat tagataactc aaaaggaaca   360
agcgatcaag agctgttaac acccgagttt aactatacct atacggaaag cacttcaaat   420
acaacaaccc atgattaaa attaggagtc aaaaccactg ctaccatgaa attcccgatt   480
gctcagggta gcatggaagc ttctactgaa tataactttc aaaattcttc cactgatact   540
aaaactaaac aagtatcata taaaagccca tcacaaaaaa ttaaagtacc agcaggtaaa   600
acctatagag ttttagcata cctaaatact ggatctattt caggtgaagc taacctttac   660
gcaaatgttg ggggtatagc ttggggggtt ttaccaggtt atcccaatgg cggaggagta   720
aatataggtg ctgtacttac caaatgccaa caaaaaggat ggggagattt cagaaacttt   780
caacctagtg gaagagatgt aatcgttaaa ggccaaggta ctttcaaatc taattatgga   840
acggacttca ttttaaaaat tgaagacatc acagattcaa agttacgaaa caataacggg   900
agtggaactg tcgttcaaga gattaaagtt ccactaatta gaactgaaat atag   954

SEQ ID NO: 78          moltype = AA   length = 317
FEATURE                Location/Qualifiers
REGION                 1..317
                       note = The amino acid sequence translation of the TIC11256
                       precursor protein from the open reading frame as set forth
                       in SEQ ID NO:77.
source                 1..317
                       mol_type = protein
                       organism = Brevibacillus laterosporus
SEQUENCE: 78
MKKFASLILT SVFLFSSTQF VHASSTDVQE RLRDLAREDE AGTFNEAWNT NFKPSDEQQF   60
SYSPTEGIVF LTPPKNVIGE RRISQYKVNN AWATLEGSPT EMSGTPLYAG KNVLDNSKGT   120
SDQELLTPEF NYTYTESTSN TTTHGLKLGV KTTATMKFPI AQGSMEASTE YNFQNSSTDT   180
KTKQVSYKSP SQKIKVPAGK TYRVLAYLNT GSISGEANLY ANVGGIAWGV LPGYPNGGGV   240
NIGAVLTKCQ QKGWGDFRNF QPSGRDVIVK GQGTFKSNYG TDFILKIEDI TDSKLRNNNG   300
SGTVVQEIKV PLIRTEI                                                  317

SEQ ID NO: 79          moltype = DNA   length = 954
FEATURE                Location/Qualifiers
misc_feature           1..954
                       note = A recombinant polynucleotide sequence obtained from
                       a Brevibacillus laterosporus species encoding a TIC4544
                       precursor protein from an open reading frame at nucleotide
                       position 1-951 and a translation termination codon.
source                 1..954
                       mol_type = other DNA
                       organism = Brevibacillus laterosporus
SEQUENCE: 79
atgaaaaaat ttgcaagttt aattcttaca agtgtgttcc ttttttcgag tacgcaattt   60
gttcatgcgt catccacaga tgttcaagaa agattacggg acttggcaag agaagatgaa   120
gctggaacct ttaatgaagc atggaatact aacttcaaac ccagtgatga acaacaattc   180
tcgtatagtc caactgaagg aattgttttc ttaacaccac ctaaaaatgt tattggcgaa   240
agaagaattt cacagtataa agtaaataat gcatgggcta cattagaagg aagtccaacc   300
gaagtatcgg ggacaccttt atatgcggga aaaaacgtat tagataactc aaaaggaaca   360
atcgatcaag agctgttaac acccgagttt agttatacct atacggaaag cacttcaaat   420
acaacaactc atggattaaa agtaggagtc aaaaccactg ctaccatgaa attcccgatt   480
gctcagggta gcatggaagc ttctactgaa tataactttc aaaattcttc cactgatact   540
aaaactaaac aagtatcata taaaagccca tcacaaaaaa ttaaagtacc agcaggtaaa   600
acctatagag ttttagcata cctaaatact ggatctattt caggtgaagc taacctttac   660
gcaaatgttg ggggtatagc ttggggggtt tcaccaggtt atcccaatgg cggaggagta   720
aatataggtg ctgtacttat caaatgccaa caaaaaggat ggggagattt cagaaacttt   780
caacctagtg gaagagatgt aatcgttaaa ggccaaggta ctttcaaatc taattatgga   840
acggacttca ttttaaaaat tgaagacatc acagattcaa agttacgaaa caataacggg   900
agtggaactg tcgttcaaga gattaaagtt ccactaatta gaactgaaat atag   954
```

-continued

```
SEQ ID NO: 80              moltype = AA   length = 317
FEATURE                    Location/Qualifiers
REGION                     1..317
                           note = The amino acid sequence translation of the TIC4544
                            precursor protein from the open reading frame as set forth
                            in SEQ ID NO:79.
source                     1..317
                           mol_type = protein
                           organism = Brevibacillus laterosporus
SEQUENCE: 80
MKKFASLILT SVFLFSSTQF VHASSTDVQE RLRDLAREDE AGTFNEAWNT NFKPSDEQQF   60
SYSPTEGIVF LTPPKNVIGE RRISQYKVNN AWATLEGSPT EVSGTPLYAG KNVLDNSKGT  120
IDQELLTPEF SYTYTESTSN TTTHGLKVGV KTTATMKFPI AQGSMEASTE YNFQNSSTDT  180
KTKQVSYKSP SQKIKVPAGK TYRVLAYLNT GSISGEANLY ANVGGIAWRV SPGYPNGGGV  240
NIGAVLIKCQ QKGWGDFRNF QPSGRDVIVK GQGTFKSNYG TDFILKIEDI TDSKLRNNNG  300
SGTVVQEIKV PLIRTEI                                                 317

SEQ ID NO: 81              moltype = DNA   length = 954
FEATURE                    Location/Qualifiers
misc_feature               1..954
                           note = A recombinant polynucleotide sequence obtained from
                            a Brevibacillus laterosporus species encoding a TIC4545
                            precursor protein from an open reading frame at nucleotide
                            position 1-951 and a translation termination codon.
source                     1..954
                           mol_type = other DNA
                           organism = Brevibacillus laterosporus
SEQUENCE: 81
atgaaaaaat ttgcaagttt aattcttata agtgtgttcc ttttttcgag tacgcaattt   60
gttcatgcgt catccacaga tgttcaagaa agattacggg acttggcaag agaagatgaa  120
gctggaaccc ttaatgaagc atggaatact aacttcaaac ccagtgatga acaacaattc  180
tcttatagtc caactgaagg aattgttttc ttaacaccac ctaaaaatgt tattggcgaa  240
agaagaattt cacagtataa agtaaataat gcatgggcta cattagaagg aagtccaacc  300
gaagtatcgg ggacaccttt atatgcggga aaaaacgtat tagataactc aaaaggaaca  360
atggatcaag agctgttaac acccgagttt aactatacct atacggaaag cacttcaaat  420
acaataactc atggattaaa attaggagtc aaaaccactg ctaccatgaa attcccgatt  480
gctcagggta gcatggaagc ttctactgaa tataactttc aaaattcttc cactgatact  540
aaaactaaac aagtatcata taaaagccca tcacaaaaaa ttaaagtacc agcaggtaaa  600
acctttagag ttttagcata cctaaatact ggatctattt caggtgaagc taacctttac  660
gcaaatgttg ggggtatagc ttggggggtt ttaccaggtt atcccaatgg cggaggagta  720
aatataggtg ctgtacttac caaatgccaa caaaaaggat ggggagattt cagaaacttt  780
caacctagtg aagagatgt aatcgttaaa ggccaaggta ctttcgaatc taattatgga  840
acggacttca ttttaaaaat tgaagacatc acagattcaa agttacgaaa caataacggg  900
agtggaactg tcgttcaaga gattaaagtt ccactaatta gaactgaaat atag         954

SEQ ID NO: 82              moltype = AA   length = 317
FEATURE                    Location/Qualifiers
REGION                     1..317
                           note = The amino acid sequence translation of the TIC4545
                            precursor protein from the open reading frame as set forth
                            in SEQ ID NO:81.
source                     1..317
                           mol_type = protein
                           organism = Brevibacillus laterosporus
SEQUENCE: 82
MKKFASLILI SVFLFSSTQF VHASSTDVQE RLRDLAREDE AGTLNEAWNT NFKPSDEQQF   60
SYSPTEGIVF LTPPKNVIGE RRISQYKVNN AWATLEGSPT EVSGTPLYAG KNVLDNSKGT  120
MDQELLTPEF NYTYTESTSN TITHGLKLGV KTTATMKFPI AQGSMEASTE YNFQNSSTDT  180
KTKQVSYKSP SQKIKVPAGK TFRVLAYLNT GSISGEANLY ANVGGIAWGV LPGYPNGGGV  240
NIGAVLTKCQ QKGWGDFRNF QPSGRDVIVK GQGTFESNYG TDFILKIEDI TDSKLRNNNG  300
SGTVVQEIKV PLIRTEI                                                 317

SEQ ID NO: 83              moltype = DNA   length = 954
FEATURE                    Location/Qualifiers
misc_feature               1..954
                           note = A recombinant polynucleotide sequence obtained from
                            a Brevibacillus laterosporus species encoding a TIC6871
                            precursor protein from an open reading frame at nucleotide
                            position 1-951 and a translation termination codon.
source                     1..954
                           mol_type = other DNA
                           organism = Brevibacillus laterosporus
SEQUENCE: 83
atgaaaaaat ttgcaagttt aattcttaca agtgtgttcc ttttttcgag tacgcaattt   60
gttcatgcgt catccacaga tgttcaagaa agattacggg acttggcaag agaagatgaa  120
gctggaacct ttaatgaagc atggaatact aacttcaaac ccagtgatga acaacaattc  180
tcgtatagtc caactgaagg aattgttttc ttaacaccac ctaaaaatgt tattggcgaa  240
agaagaattt cacagtataa agtaaataat gcatgggcta cattagaagg aagtccaacc  300
gaagtatcgg ggacaccttt atatgcggga aaaaacgtat tagataactc aaaaggaaca  360
```

```
atcgatcaag agctgttaac acccgagttt agttatacct atacggaaag cacttcaaat  420
acaacaactc atggattaaa attaggagtc aaaaccactg ctaccatgaa attcccgatt  480
gctcagggta gcatggaagc ttctactgaa tataactttc aaaattcttc cactgatact  540
aaaactaaac aagtatcata taaaagccca tcacaaaaaa ttaaagtacc agcaggtaaa  600
acctatagag ttttagcata cctaaatact ggatctattt caggtgaagc taacctttac  660
gcaaatgttg ggggtatagc ttggagggtt tcaccaggtt atcccaatgg cggaggagta  720
aatataggtg ctgtacttac caaatgccaa caaaaaggat ggggagattt cagaaacttt  780
caacctagtg gaagagatgt aatcgttaaa ggccaaggta ctttcaaatc taattatgga  840
acggacttca ttttaaaaat tgaagacatc acagattcaa agttacgaaa caataacggg  900
agtggaactg tcgttcaaga gattaaagtt ccactaatta gaactgaaat atag        954
```

SEQ ID NO: 84            moltype = AA  length = 317
FEATURE                  Location/Qualifiers
REGION                   1..317
                         note = The amino acid sequence translation of the TIC6871
                          precursor protein from the open reading frame as set forth
                          in SEQ ID NO:83.
source                   1..317
                         mol_type = protein
                         organism = Brevibacillus laterosporus
SEQUENCE: 84
MKKFASLILT SVFLFSSTQF VHASSTDVQE RLRDLAREDE AGTFNEAWNT NFKPSDEQQF  60
SYSPTEGIVF LTPPKNVIGE RRISQYKVNN AWATLEGSPT EVSGTPLYAG KNVLDNSKGT  120
IDQELLTPEF SYTYTESTSN TTTHGLKLGV KTTATMKFPI AQGSMEASTE YNFQNSSTDT  180
KTKQVSYKSP SQKIKVPAGK TYRVLAYLNT GSISGEANLY ANVGGIAWRV SPGYPNGGGV  240
NIGAVLTKCQ QKGWGDFRNF QPSGRDVIVK GQGTFKSNYG TDFILKIEDI TDSKLRNNNG  300
SGTVVQEIKV PLIRTEI                                                 317

SEQ ID NO: 85            moltype = DNA  length = 954
FEATURE                  Location/Qualifiers
misc_feature             1..954
                         note = A recombinant polynucleotide sequence obtained from
                          a Brevibacillus laterosporus species encoding a TIC7429
                          precursor protein from an open reading frame at nucleotide
                          position 1-951 and a translation termination codon.
source                   1..954
                         mol_type = other DNA
                         organism = Brevibacillus laterosporus
SEQUENCE: 85
```
atgaaaaaat ttgcaagttt aattcttata agtgtgttcc tttttttcgag tacgcaattt  60
gttcatgcgt catccacaga tgttcaagaa cgattacggg acttggcaag agaagatgaa  120
gctggaaccc ttaatgaagc atggaatact aacttcaaac ccagtgatga acaacaattc  180
tcttatagtc caactgaagg aattgttttc ttaacaccac ctaaaaatgt tattggcaga  240
agaagaattt cacagtataa agtaaataat gcatgggcta cattagaagg aagtccaacc  300
gaagtatcgg ggacaccttt atatgcggga aaaaacgtat tagataactc aaaaggaaca  360
atggatcaag agctgttaac acccgagttt aactatacct atacgaaag cacttcaaat  420
acaacaactc atggattaaa attaggagtc aaaaccactg ctaccatgaa attcccgatt  480
gctcagggta gcatggaagc ttctactgaa tataacttc aaaattcttc cactgatact  540
aaaactaaac aagtatcata taaaagccca tcacaaaaaa ttaaagtacc agcaggtaaa  600
acctatagag ttttagcata cctaaatact ggatctattt caggtgaagc taacctttac  660
gcaaatgttg ggggtatagc ttggagggtt tcaccaggtt atcccaatgg cggaggagta  720
aatataggtg ctgtacttac caaatgccaa caaaaaggat ggggagattt cagaaacttt  780
caacctagtg gaagagatgt aatcgttaaa ggccaaggta ctttcacatc taattatgga  840
acggacttca ttttaaaaat tgaagacatc acagattcaa agttacgaaa caataacggg  900
agtggaactg tcgttcaaga gattaaagtt ccactaatta gaactgaaat atag        954
```

SEQ ID NO: 86            moltype = AA  length = 317
FEATURE                  Location/Qualifiers
REGION                   1..317
                         note = The amino acid sequence translation of the TIC7429
                          precursor protein from the open reading frame as set forth
                          in SEQ ID NO:85.
source                   1..317
                         mol_type = protein
                         organism = Brevibacillus laterosporus
SEQUENCE: 86
MKKFASLILI SVFLFSSTQF VHASSTDVQE RLRDLAREDE AGTLNEAWNT NFKPSDEQQF  60
SYSPTEGIVF LTPPKNVIGE RRISQYKVNN AWATLEGSPT EVSGTPLYAG KNVLDNSKGT  120
MDQELLTPEF NYTYTESTSN TTTHGLKLGV KTTATMKFPI AQGSMEASTE YNFQNSSTDT  180
KTKQVSYKSP SQKIKVPAGK TYRVLAYLNT GSISGEANLY ANVGGIAWRV SPGYPNGGGV  240
NIGAVLTKCQ QKGWGDFRNF QPSGRDVIVK GQGTFTSNYG TDFILKIEDI TDSKLRNNNG  300
SGTVVQEIKV PLIRTEI                                                 317

SEQ ID NO: 87            moltype = DNA  length = 954
FEATURE                  Location/Qualifiers
misc_feature             1..954
                         note = A recombinant polynucleotide sequence obtained from
                          a Brevibacillus laterosporus species encoding a TIC7497
                          precursor protein from an open reading frame at nucleotide -continued

```
                       position 1-951 and a translation termination codon.
source                 1..954
                       mol_type = other DNA
                       organism = Brevibacillus laterosporus
SEQUENCE: 87
atgaaaaaat ttgcaagttt aattcttaca agtgtgttcc ttttttcgag tacgcaattt   60
gttcatgcgt catccacaga tgttcaagaa agattacggg acttggcaag agaagatgaa   120
gctggaacct ttaatgaagc atggaatact aacttcaaac ccagtgatca acaacaattc   180
tcttatagtc caactgaagg aattgttttc ttaacaccac ctaaaaatgt tattggcgaa   240
agaagaattt cacagtataa agtaaataat gcatgggcta cattagaagg aagtccaacc   300
gaagtatcgg ggacaccttt atatgcggga aaaaacgtat tagataactc aaaaggaaca   360
atggatcaag agctgttaac acccgagttt aactatacct atacggaaag cacttcaaat   420
acaacaactc atggattaaa agtaggagtc aaaaccactg ctaccatgaa attcccgatt   480
gctcagggta gcatggaagc ttctactgaa tataactttc aaaattcttc cactgatact   540
aaaactaaac aagtatcata taaaagccca tcacaaaaga ttaaagtacc agcaggtaaa   600
acctttagag ttttagcata cctaaatact ggatctattt caggtgaagc taacctttac   660
gcaaatgttg ggggtatagc ttggagggtt tcaccaggtt atcccaatgg cggaggagta   720
aatataggtg ctgtacttac caaatgccaa caaaaaggat ggggagattt cagaaacttt   780
caacctagtg gaagagatgt aatcgttaaa ggccaaggta ctttcaaatc taattatgga   840
acggacttca ttttaaaaat tgaagacatc acagattcaa agttacgaaa caataacggg   900
agtggaactg tcgttcaaga gattaaagtt ccactaatta gaactgaaat atag           954

SEQ ID NO: 88          moltype = AA   length = 317
FEATURE                Location/Qualifiers
REGION                 1..317
                       note = The amino acid sequence translation of the TIC7497
                        precursor protein from the open reading frame as set forth
                        in SEQ ID NO:89.
source                 1..317
                       mol_type = protein
                       organism = Brevibacillus laterosporus
SEQUENCE: 88
MKKFASLILT SVFLFSSTQF VHASSTDVQE RLRDLAREDE AGTFNEAWNT NFKPSDQQQF   60
SYSPTEGIVF LTPPKNVIGE RRISQYKVNN AWATLEGSPT EVSGTPLYAG KNVLDNSKGT   120
MDQELLTPEF NYTYTESTSN TTTHGLKVGV KTTATMKFPI AQGSMEASTE YNFQNSSTDT   180
KTKQVSYKSP SQKIKVPAGK TFRVLAYLNT GSISGEANLY ANVGGIAWRV SPGYPNGGGV   240
NIGAVLTKCQ QKGWGDFRNF QPSGRDVIVK GQGTFKSNYG TDFILKIEDI TDSKLRNNNG   300
SGTVVQEIKV PLIRTEI                                                    317

SEQ ID NO: 89          moltype = DNA   length = 954
FEATURE                Location/Qualifiers
misc_feature           1..954
                       note = A recombinant polynucleotide sequence obtained from
                        a Brevibacillus laterosporus species encoding a TIC7511
                        precursor protein from an open reading frame at nucleotide
                        position 1-951 and a translation termination codon.
source                 1..954
                       mol_type = other DNA
                       organism = Brevibacillus laterosporus
SEQUENCE: 89
atgaaaaaat ttgcaagttt aattcttata agtgtgttcc ttttttcgag tacgcaattt   60
gttcatgcgt catccacaga tgttcaagaa agattacggg acttggcaag agaagatgaa   120
gctggaacct ttaatgaagc atggaatact aacttcaaac ccagtgatca acaacaattc   180
tcttatagtc caactgaagg aattgttttc ttaacaccac ctaaaaatgt tattggcgaa   240
agaagaattt cacagtataa agtaaataat gcatgggcta cattagaagg aagtccaacc   300
gaagtatcgg ggacaccttt atatgtggga aaaaacgtat tagataactc aaaaggaaca   360
agcgatcaag agctgttaac acccgagttt aactatacct atacggaaag cacttcaaat   420
acaacaactc atggattaaa agtaggagtc aaaaccactg ctaccatgaa attcccgatt   480
gctcagggta gcatggaagc ttctactgaa tataactttc aagattcttc cactgatact   540
acaactaaaa cagtatcata taaaagccca tcacaaaaga ttaaagtacc agcaggtaaa   600
acctttagag ttttagcata cctaaatact ggatctattt caggtgaagc taacctttac   660
gcaaatgttg ggggtatagc ttggagggtt tcaccaggtt atcccaatgg cggaggagta   720
aatataggtg ctgtacttac caaatgccaa caaaaaggat ggggagattt cagaaacttt   780
caacctagtg gaagagatgt aatcgttaaa ggccaaggta cattcaaatc taattatgga   840
acggacttca ttttaaaaat tgaagacatc acagattcaa agttacgaaa caataacggg   900
agtggaactg tcgttcaaga gattaaagtt ccactaatta gaactgaaat atag           954

SEQ ID NO: 90          moltype = AA   length = 317
FEATURE                Location/Qualifiers
REGION                 1..317
                       note = The amino acid sequence translation of the TIC7511
                        precursor protein from the open reading frame as set forth
                        in SEQ ID NO:91.
source                 1..317
                       mol_type = protein
                       organism = Brevibacillus laterosporus
SEQUENCE: 90
MKKFASLILI SVFLFSSTQF VHASSTDVQE RLRDLAREDE AGTFNEAWNT NFKPSDQQQF   60
SYSPTEGIVF LTPPKNVIGE RRISQYKVNN AWATLEGSPT EVSGTPLYVG KNVLDNSKGT   120
```

-continued

```
SDQELLTPEF NYTYTESTSN TTTHGLKVGV KTTATMKFPI AQGSMEASTE YNFQDSSTDT  180
TTKTVSYKSP SQKIKVPAGK TFRVLAYLNT GSISGEANLY ANVGGIAWRV SPGYPNGGGV  240
NIGAVLTKCQ QKGWGDFRNF QPSGRDVIVK GQGTFKSNYG TDFILKIEDI TDSKLRNNNG  300
SGTVVQEIKV PLIRTEI                                                  317

SEQ ID NO: 91        moltype = DNA  length = 954
FEATURE              Location/Qualifiers
misc_feature         1..954
                     note = A recombinant polynucleotide sequence obtained from
                      a Brevibacillus laterosporus species encoding a TIC7513
                      precursor protein from an open reading frame at nucleotide
                      position 1-951 and a translation termination codon.
source               1..954
                     mol_type = other DNA
                     organism = Brevibacillus laterosporus
SEQUENCE: 91
atgaaaaaat ttgcaagttt aattcttata agtgtgttcc ttttttcgag tacgcaattt  60
gttcatgcgt catccacaga tgttcaagaa agattacggg acttggcaag agaagatgaa  120
gctggaacct ttaatgaagc atggaatact aacttcaaac ccagtgatga acaacaattc  180
tcttatagtc caactgaagg aattgttttc ttaacaccac ctaaaaatgt tattggcgaa  240
agaagaattc cacagtataa agtaaataat gcatgggcta cattagaagg aagtccaacc  300
gaagcatcgg ggacaccttt atatgcggga aaaaacgtat tagataactc aaaaggaaca  360
atggatcaag agctgttaac acccgagttt aactatacct atacggaaag cacttcaaat  420
acaacaaccc atggattaaa attaggagtc aaaaccactg ctaccatgaa attcccgatt  480
gctcagggta gcatggaagc ttctactgaa tataactttc aaaattcttc cactgatact  540
aaaactaaac aagtatcata taaaagccca tcacaaaaaa ttaaagtacc agcaggtaaa  600
acctatagag ttttagcata cctaaatact ggatctattt caggtgaagc taacctttac  660
gcaaatgttg ggggtatagc ttggagggtt tcaccaggtt atcccaatgg cggaggagta  720
aatataggtg ctgtacttac caaatgccaa caaaaaggat ggggagattt cagaaacttt  780
caacctagtg gaagagatgt aatcgttaaa ggccaaggta ctttcaaatc taattatgga  840
acggacttca ttttaaaaat tgaagacatc acagattcaa agttacgaaa caataacggg  900
agtggaactg tcgttcaaga gattaaagtt ccactaatta gaactgaaat atag         954

SEQ ID NO: 92        moltype = AA  length = 317
FEATURE              Location/Qualifiers
REGION               1..317
                     note = The amino acid sequence translation of the TIC7513
                      precursor protein from the open reading frame as set forth
                      in SEQ ID NO:93.
source               1..317
                     mol_type = protein
                     organism = Brevibacillus laterosporus
SEQUENCE: 92
MKKFASLILI SVFLFSSTQF VHASSTDVQE RLRDLAREDE AGTFNEAWNT NFKPSDEQQF  60
SYSPTEGIVF LTPPKNVIGE RRISQYKVNN AWATLEGSPT EASGTPLYAG KNVLDNSKGT  120
MDQELLTPEF NYTYTESTSN TTTHGLKLGV KTTATMKFPI AQGSMEASTE YNFQNSSTDT  180
KTKQVSYKSP SQKIKVPAGK TYRVLAYLNT GSISGEANLY ANVGGIAWRV SPGYPNGGGV  240
NIGAVLTKCQ QKGWGDFRNF QPSGRDVIVK GQGTFKSNYG TDFILKIEDI TDSKLRNNNG  300
SGTVVQEIKV PLIRTEI                                                  317

SEQ ID NO: 93        moltype = DNA  length = 954
FEATURE              Location/Qualifiers
misc_feature         1..954
                     note = A recombinant polynucleotide sequence obtained from
                      a Brevibacillus laterosporus species encoding a TIC7518
                      precursor protein from an open reading frame at nucleotide
                      position 1-951 and a translation termination codon.
source               1..954
                     mol_type = other DNA
                     organism = Brevibacillus laterosporus
SEQUENCE: 93
atgaaaaaat ttgcaagttt aattcttata agtgtgttcc ttttttcgag tacgcaattt  60
gttcatgcgt catccacaga tgttcaagaa agattacggg acttggcaag agaaaatgaa  120
gctggaaccc ttaatgaagc atggaatact aacttcaaac ccagtgatga acaacaattc  180
tcttatagtc caactgaagg aattgttttc ttaacaccac ctaaaaatgt tattggcgaa  240
agaagaattc cacagtataa agtaaataat gcatgggcta cattagaagg aagtccaacc  300
gaagtatcgg ggacaccttt atatgcggga aaaacgtat tagataactc aaaaggaaca  360
atggatcaag agctgttaac acccgagttt aactatacct atacggaaag cacttcaaat  420
acaataactc atggattaaa attaggagtc aaaaccactg ctaccatgaa attcccgatt  480
gctcagggta gcatggaagc ttctactgaa tataactttc aaaattcttc cactgatact  540
aaaactaaac aagtatcata taaaagccca tcacaaaaaa ttaaagtacc agcaggtaaa  600
acctttagag ttttagcata cctaaatact ggatctattt caggtgaagc taacctttac  660
gcaaatgttg ggggtatagc ttggggggtt ttaccaggtt atcccaatgg cggaggagta  720
aatataggtg ctgtacttac caaatgccaa caaaaaggat ggggagattt cagaaacttt  780
caacctagtg gaagagatgt aatcgttaaa ggccaaggta ctttcgaatc taattatgga  840
acggacttca ttttaaaaat tgaagacatc acagattcaa agttacgaaa caataacggg  900
agtggaactg tcgttcaaga gattaaagtt ccactaatta gaactgaaat atag         954

SEQ ID NO: 94        moltype = AA  length = 317
```

-continued

```
FEATURE          Location/Qualifiers
REGION           1..317
                 note = The amino acid sequence translation of the TIC7518
                  precursor protein from the open reading frame as set forth
                  in SEQ ID NO:95.
source           1..317
                 mol_type = protein
                 organism = Brevibacillus laterosporus
SEQUENCE: 94
MKKFASLILI SVFLFSSTQF VHASSTDVQE RLRDLARENE AGTLNEAWNT NFKPSDEQQF   60
SYSPTEGIVF LTPPKNVIGE RRISQYKVNN AWATLEGSPT EVSGTPLYAG KNVLDNSKGT  120
MDQELLTPEF NYTYTESTSN TITHGLKLGV KTTATMKFPI AQGSMEASTE YNFQNSSTDT  180
KTKQVSYKSP SQKIKVPAGK TFRVLAYLNT GSISGEANLY ANVGGIAWGV LPGYPNGGGV  240
NIGAVLTKCQ QKGWGDFRNF QPSGRDVIVK GQGTFESNYG TDFILKIEDI TDSKLRNNNG  300
SGTVVQEIKV PLIRTEI                                                 317

SEQ ID NO: 95      moltype = DNA   length = 954
FEATURE            Location/Qualifiers
misc_feature       1..954
                   note = A recombinant polynucleotide sequence obtained from
                    a Brevibacillus laterosporus species encoding a TIC7524
                    precursor protein from an open reading frame at nucleotide
                    position 1-951 and a translation termination codon.
source             1..954
                   mol_type = other DNA
                   organism = Brevibacillus laterosporus
SEQUENCE: 95
atgaaaaaat ttgcaagttt aattcttaca agtgtgttcc tttttttcgag tacccaaatt   60
gttcatgcgt catccacaga tgttcaagaa agattacggg acttggcaag agaagatgaa  120
gctggaacct ttaatgaagc atggaatact aacttcaaac ccagtgatga acaacaattc  180
tcttatagtc caactgaagg aattgttttc ttaacaccac ctaaaaatgt tattggcgaa  240
agaagaattt cacagtataa agtaaataat gcatgggcta cattagaagg aagtccaacc  300
gaagcatcgg ggacaccttt atatgcggga aaaaacgtat tagataactc aaaaggaaca  360
atggatcaag agctgttaac acccgagttt aactatacct cacttcaaat  420
acaacaacct atggattaaa attaggagtc aaaaccactg ctaccatgaa attcccgatt  480
gctcagggta gcatggaagc ttctactgaa tataactttc aaaattcttc cactgatact  540
aaaactaaac aagtatcata taaaagccca tcacaaaaaa ttaaagtacc agcaggtaaa  600
acctatagag ttttagcata cctaaatact ggatctattt caggtgaagc taacctttac  660
gcaaatgttg ggggtatagc ttggaggggtt tcaccaggtt atcccaatgg cggaggagta  720
aatataggtg ctgtacttac caaatgccaa caaaaaggat ggggagattt cagaaacttt  780
caacctagtg gaagagatgt aatcgttaaa ggccaaggta ctttcgaatc taattatgga  840
acggacttca ttttaaaaat tgaagacatc acagattcaa agttacgaaa caataacggg  900
agtggaactg tcgttcaaga gattaaagtt ccactaatta gaactgaaat atag         954

SEQ ID NO: 96      moltype = AA   length = 317
FEATURE            Location/Qualifiers
REGION             1..317
                   note = The amino acid sequence translation of the TIC7524
                    precursor protein from the open reading frame as set forth
                    in SEQ ID NO:97.
source             1..317
                   mol_type = protein
                   organism = Brevibacillus laterosporus
SEQUENCE: 96
MKKFASLILT SVFLFSSTQI VHASSTDVQE RLRDLAREDE AGTFNEAWNT NFKPSDEQQF   60
SYSPTEGIVF LTPPKNVIGE RRISQYKVNN AWATLEGSPT EASGTPLYAG KNVLDNSKGT  120
MDQELLTPEF NYTYTESTSN TTTHGLKLGV KTTATMKFPI AQGSMEASTE YNFQNSSTDT  180
KTKQVSYKSP SQKIKVPAGK TYRVLAYLNT GSISGEANLY ANVGGIAWRV SPGYPNGGGV  240
NIGAVLTKCQ QKGWGDFRNF QPSGRDVIVK GQGTFESNYG TDFILKIEDI TDSKLRNNNG  300
SGTVVQEIKV PLIRTEI                                                 317

SEQ ID NO: 97      moltype = DNA   length = 954
FEATURE            Location/Qualifiers
misc_feature       1..954
                   note = A recombinant polynucleotide sequence obtained from
                    a Brevibacillus laterosporus species encoding a TIC7526
                    precursor protein from an open reading frame at nucleotide
                    position 1-951 and a translation termination codon.
source             1..954
                   mol_type = other DNA
                   organism = Brevibacillus laterosporus
SEQUENCE: 97
atgaaaaaat ttgcaagttt aattcttata agtgtgttcc tttttttcgag tacgcaattt   60
gttcatgcgt catccacaga tgttcaagaa agattacggg acttagcaag agaaaatgaa  120
gctggaaccc ttaatgaagc atggaatact aacttcaaac ccagtgatga acaacaattc  180
tcttatagtc caactgaagg tattgttttc ttaacaccac ctaaaaatgt tattggcgaa  240
agaagaattt cacagtataa agtaaataat gcatgggcta cattagaagg aagtccaatc  300
gaagtatcgg ggacaccttt atatgcggga aaaaacgtat tagataactc aaaaggaaca  360
atggatcaag agctgttaac acccgagttt aactatacct atacgaaaag cacttcaaat  420
```

```
acaataactc atggattaaa attaggagtc aaaaccactg ctaccatgaa attcccgatt   480
gctcagggta gcatggaagc ttctactgaa tataactttc aaaattcttc cactgatact   540
aaaactaaac aagtatcata taaaagccca tcacaaaaaa ttaaagtacc agcaggtaaa   600
acctttagag ttttagcata cctaaatact ggatctattt caggtgaagc taacctttac   660
gcaaatgttg ggggtatagc ttggggggtt ttaccaggtt atcccaatgg cggaggagta   720
aatataggtc ctgtacttac caaatgccaa caaaaaggat ggggagattt cagaaacttt   780
caacctagtg gaagagatgt aatcgttaaa ggccaaggta ctttcgaatc taattatgga   840
acggacttca ttttaaaaat tgaagacatc acagattcaa agttacgaaa caataacggg   900
agtggaactg tcgttcaaga gattaaagtt ccactaatta gaactgaaat atag         954
```

SEQ ID NO: 98        moltype = AA   length = 317
FEATURE              Location/Qualifiers
REGION               1..317
                     note = The amino acid sequence translation of the TIC7526
                      precursor protein from the open reading frame as set forth
                      in SEQ ID NO:99.
source               1..317
                     mol_type = protein
                     organism = Brevibacillus laterosporus
SEQUENCE: 98
MKKFASLILI SVFLFSSTQF VHASSTDVQE RLRDLARENE AGTLNEAWNT NFKPSDEQQF   60
SYSPTEGIVF LTPPKNVIGE RRISQYKVNN AWATLEGSPI EVSGTPLYAG KNVLDNSKGT   120
MDQELLTPEF NYTYTESTSN TITHGLKLGV KTTATMKFPI AQGSMEASTE YNFQNSSTDT   180
KTKQVSYKSP SQKIKVPAGK TFRVLAYLNT GSISGEANLY ANVGGIAWGV LPGYPNGGGV   240
NIGAVLTKCQ QKGWGDFRNF QPSGRDVIVK GQGTFESNYG TDFILKIEDI TDSKLRNNNG   300
SGTVVQEIKV PLIRTEI                                                  317

SEQ ID NO: 99        moltype = DNA   length = 954
FEATURE              Location/Qualifiers
misc_feature         1..954
                     note = A recombinant polynucleotide sequence obtained from
                      a Brevibacillus laterosporus species encoding a TIC7528
                      precursor protein from an open reading frame at nucleotide
                      position 1-951 and a translation termination codon.
source               1..954
                     mol_type = other DNA
                     organism = Brevibacillus laterosporus
SEQUENCE: 99
atgaaaaaat ttgcaagttt aattcttaca agtgtgttcc ttttttcgag tacgcaattt   60
gttcatgcgt catccacaga tgttcaagaa agattacggg acttggcaag agaagatgaa   120
gctggaacct ttaatgaagc atggaatact aacttcaaac ccagtgatca acaacaattc   180
tcttatagtc caactgaagg aattgttttc ttaacaccac ctaaaaatgt tattggcgaa   240
agaagaattt cacagtataa agtaaataat gcatgggcta cattagaagg aagtccaacc   300
gaagtatcgg ggacaccttt atatgcggga aaaaacgtat tagataactc aaaaggaaca   360
atggatcaag agctgttaac acccgagttt aactatacct atacggaaag cacttcaaat   420
acaacaactc atggattaaa attaggagtc aaaaccactg ctaccatgaa attcccgatt   480
gctcagggta gcatggaagc ttctactgaa tataactttc aaaattcttc cactgatact   540
aaaactaaac aagtatcata taaaagccca tcacaaaaga ttaaagtacc agcaggtaaa   600
acctttagag ttttagcata cctaaatact ggatctattt caggtgaagc taacctttac   660
gcaaatgttg ggggtatagc ttggagggtt tcaccaggtt atcccaatgg cggaggagta   720
aatataggtc ctgtacttac caaatgccaa caaaaaggat ggggagattt cagaaacttt   780
caacctagtg gaagagatgt aatcgttaaa ggccaaggta ctttcaaatc taattatgga   840
acggacttca ttttaaaaat tgaagacatc acagattcaa agttacgaaa caataacggg   900
agtggaactg tcgttcaaga gattaaagtt ccactaatta gaactgaaat atag         954
```

SEQ ID NO: 100       moltype = AA   length = 317
FEATURE              Location/Qualifiers
REGION               1..317
                     note = The amino acid sequence translation of the TIC7528
                      precursor protein from the open reading frame as set forth
                      in SEQ ID NO:101.
source               1..317
                     mol_type = protein
                     organism = Brevibacillus laterosporus
SEQUENCE: 100
MKKFASLILT SVFLFSSTQF VHASSTDVQE RLRDLAREDE AGTFNEAWNT NFKPSDQQQF   60
SYSPTEGIVF LTPPKNVIGE RRISQYKVNN AWATLEGSPT EVSGTPLYAG KNVLDNSKGT   120
MDQELLTPEF NYTYTESTSN TTTHGLKLGV KTTATMKFPI AQGSMEASTE YNFQNSSTDT   180
KTKQVSYKSP SQKIKVPAGK TFRVLAYLNT GSISGEANLY ANVGGIAWRV SPGYPNGGGV   240
NIGAVLTKCQ QKGWGDFRNF QPSGRDVIVK GQGTFKSNYG TDFILKIEDI TDSKLRNNNG   300
SGTVVQEIKV PLIRTEI                                                  317

SEQ ID NO: 101       moltype = DNA   length = 954
FEATURE              Location/Qualifiers
misc_feature         1..954
                     note = A recombinant polynucleotide sequence obtained from
                      a Brevibacillus laterosporus species encoding a TIC7535
                      precursor protein from an open reading frame at nucleotide
                      position 1-951 and a translation termination codon.

```
source                  1..954
                        mol_type = other DNA
                        organism = Brevibacillus laterosporus
SEQUENCE: 101
atgaaaaaat ttgcaagttt aattcttaca agtgtgttcc ttttttcgag tacgcaattt   60
gttcatgcgt catccacaga tgttcaagaa agattacggg acttggcaag agaagatgaa  120
gctggaacct ttaatgaagc atggaatact aacttcaaac ccagtgatca acaacaattc  180
tcttatagtc caactgaagg aattgttttc ttaacaccac ctaaaaatgt tattggcgaa  240
agaagaattt cacagtataa agtaaataat gcatgggcta cattagaagg aagtccaacc  300
gaagcatcgg ggacaccttt atatgcggga aaaacgtat  tagataactc aaaaggaaca  360
atggatcaag agctgttaac acccgagttt agttatacct atacggaaag cacttcaaat  420
acaacaaccc atggattaaa attaggagtc aaaaccactg ctaccatgaa attcccgatt  480
gctcaggta gcatggaagc ttctactgaa tataactttc aaaattcttc cactgatact  540
aaaactaaac aagtatcata taaaagccca tcacaaaaaa ttaaagtacc agcaggtaaa  600
acctatagag ttttagcata cctaaatact ggatctattt caggtgaagc taacctttac  660
gcaaatgttg ggggtatagc ttggagggtt tcaccaggtt atcccaatgg cggaggagta  720
aatataggtg ctgtacttac caaatgccaa caaaaaggat ggggagattt cagaaacttt  780
caacctagtg gaagagatgt aatcgttaaa ggccaaggta ctttcaaatc taattatgaa  840
acggacttca ttttaaaaat tgaagacatc acagattcaa agttacgaaa caataacggg  900
agtgtggaactg tcgttcaaga gattaaagtt ccactaatta gaactgaaat atag        954

SEQ ID NO: 102          moltype = AA  length = 317
FEATURE                 Location/Qualifiers
REGION                  1..317
                        note = The amino acid sequence translation of the TIC7535
                         precursor protein from the open reading frame as set forth
                         in SEQ ID NO:103.
source                  1..317
                        mol_type = protein
                        organism = Brevibacillus laterosporus
SEQUENCE: 102
MKKFASLILT SVFLFSSTQF VHASSTDVQE RLRDLAREDE AGTFNEAWNT NFKPSDQQQF   60
SYSPTEGIVF LTPPKNVIGE RRISQYKVNN AWATLEGSPT EASGTPLYAG KNVLDNSKGT  120
MDQELLTPEF SYTYTESTSN TTTHGLKLGV KTTATMKFPI AQGSMEASTE YNFQNSSTDT  180
KTKQVSYKSP SQKIKVPAGK TYRVLAYLNT GSISGEANLY ANVGGIAWRV SPGYPNGGGV  240
NIGAVLTKCQ QKGWGDFRNF QPSGRDVIVK GQGTFKSNYG TDFILKIEDI TDSKLRNNNG  300
SGTVVQEIKV PLIRTEI                                                  317

SEQ ID NO: 103          moltype = DNA  length = 888
FEATURE                 Location/Qualifiers
misc_feature            1..888
                        note = A synthetic nucleotide sequence encoding a mature
                         TIC11239 protein, mTIC11239 for expression in bacteria.
source                  1..888
                        mol_type = other DNA
                        organism = synthetic construct
SEQUENCE: 103
atgtcatcca cagatgttca agaaagatta cgggacttgg caagagaaga tgaagctgga   60
acctttaatg aagcatggaa tactaacttc aaacccagtg atgaacaaca attctcttat  120
agtccaactg aaggaattgt tttcttaaca ccacctaaaa atgttattgg cgaaagaaga  180
atttcacagt ataaagtaaa taatgcatgg gctacattag aaggaagtcc aaccgaagta  240
tcggggacac cttttatatgc gggaaaaaac gtattagata actcaaaagg aacaatggat  300
caagagctgt taacacccga gtttaactat acctatacgg aaagcacttc aaatacaata  360
actcatggat taaaattagg agtcaaaacc actgctacca tgaaattccc gattgctcag  420
ggtagcttctac tgaatataac tttcaaaatt cttccactga tactaaaaact  480
aaacaagtat catataaaag cccatcacaa aaaattaaag taccagcagg taaaacctat  540
agagttttag catacctaaa tactggatct atttcaggtg aagctaacct ttacgcaaat  600
gttggggggta tagcttggag ggtttcacca ggttatccca tggcggagg agtaaatata  660
ggtgctgtac ttaccaaatg ccaacaaaaa ggatggggag atttcagaaa ctttcaacct  720
agtggaagag atgtaatcgt taaaggccaa ggtactttcg aatctaatta tggaacggac  780
ttcatttaaa aaattgaaga catcacagat tcaaagttac gaaacaataa cgggagtgga  840
actgtcgttc aagagattaa agttccacta attagaactg aaatatag                888

SEQ ID NO: 104          moltype = AA  length = 295
FEATURE                 Location/Qualifiers
REGION                  1..295
                        note = An amino acid sequence of a mature TIC11239 protein,
                         mTIC11239.
source                  1..295
                        mol_type = protein
                        organism = synthetic construct
SEQUENCE: 104
MSSTDVQERL RDLAREDEAG TFNEAWNTNF KPSDEQQFSY SPTEGIVFLT PPKNVIGERR   60
ISQYKVNNAW ATLEGSPTEV SGTPLYAGKN VLDNSKGTMD QELLTPEFNY TYTESTSNTI  120
THGLKLGVKT TATMKFPIAQ GSMEASTEYN FQNSSTDTKT KQVSYKSPSQ KIKVPAGKTY  180
RVLAYLNTGS ISGEANLYAN VGGIAWRVSP GYPNGGGVNI GAVLTKCQQK GWGDFRNFQP  240
SGRDVIVKGQ GTFESNYGTD FILKIEDITD SKLRNNNGSG TVVQEIKVPL IRTEI        295

SEQ ID NO: 105          moltype = DNA  length = 888
```

```
FEATURE              Location/Qualifiers
misc_feature         1..888
                     note = A synthetic nucleotide sequence encoding a mature
                      TIC11243 protein, mTIC11243 for expression in bacteria.
source               1..888
                     mol_type = other DNA
                     organism = synthetic construct
SEQUENCE: 105
atgtcatcca cagatgttca agaaagatta cgggacttgg caagagaaga tgaagctgga    60
acctttaatg aagcatggaa tactaacttc aaacccagtg atgaacaaca attctcgtat   120
agtccaactg aaggaattgt tttcttaaca ccacctaaaa atgttattgg cgaaagaaga   180
atttcacagt ataaagtaaa taatgcatgg gctacattag aaggaagtcc aaccgaagca   240
tcggggacac ctttatatgc gggaaaaaac gtattagata actcaaaagg aacaatggat   300
caagagctgt taacacccga gtttagttat acctatacgg aaagcacttc aaatacaaca   360
acccatggat taaaattagg agtcaaaacc actgctacca tgaaattccc gattgctcag   420
ggtagcatgg aagcttctac tgaatataac tttcaaaatt cttccactga tactaaaact   480
aaacaagtat catataaaag cccatcacaa aaaattaaag taccagcagg taaaacctat   540
agagttttag catacctaaa tactggatct atttcaggtg aagctaacct ttacgcaaat   600
gttgggggta tagcttggag ggtttcacca ggttatccca atggcggagg agtaaatata   660
ggtgctgtac ttaccaaatg ccaacaaaaa ggatggggag atttcagaaa ctttcaacct   720
agtggaagag atgtaatcgt taaaggccaa ggtactttca aatctaatta tggaacggac   780
ttcattttaa aaattgaaga catcacagat tcaaaattac gaaacaataa cgggagtgga   840
actgtcgttc aagagattaa agttccacta attagaactg aaatatag                888

SEQ ID NO: 106       moltype = AA   length = 295
FEATURE              Location/Qualifiers
REGION               1..295
                     note = An amino acid sequence of a mature TIC11243 protein,
                      mTIC11243.
source               1..295
                     mol_type = protein
                     organism = synthetic construct
SEQUENCE: 106
MSSTDVQERL RDLAREDEAG TFNEAWNTNF KPSDEQQFSY SPTEGIVFLT PPKNVIGERR    60
ISQYKVNNAW ATLEGSPTEA SGTPLYAGKN VLDNSKGTMD QELLTPEFSY TYTESTSNTT   120
THGLKLGVKT TATMKFPIAQ GSMEASTEYN FQNSSTDTKT KQVSYKSPSQ KIKVPAGKTY   180
RVLAYLNTGS ISGEANLYAN VGGIAWRVSP GYPNGGGVNI GAVLTKCQQK GWGDFRNFQP   240
SGRDVIVKGQ GTFKSNYGTD FILKIEDITD SKLRNNNGSG TVVQEIKVPL IRTEI        295

SEQ ID NO: 107       moltype = DNA   length = 888
FEATURE              Location/Qualifiers
misc_feature         1..888
                     note = A synthetic nucleotide sequence encoding a mature
                      TIC11256 protein, mTIC11256 for expression in bacteria.
source               1..888
                     mol_type = other DNA
                     organism = synthetic construct
SEQUENCE: 107
atgtcatcca cagatgttca agaaagatta cgggacttgg caagagaaga tgaagctgga    60
acctttaatg aagcatggaa tactaacttc aaacccagtg atgaacaaca attctcttat   120
agtccaactg aaggaattgt tttcttaaca ccacctaaaa atgttattgg cgaaagaaga   180
atttcacagt ataaagtaaa taatgcatgg gctacattag aaggaagtcc aaccgaaatg   240
tcggggacac ctttatatgc gggaaaaaac gtattagata actcaaaagg aacaagcgat   300
caagagctgt taacacccga gtttaactat acctatacgg aaagcacttc aaatacaaca   360
acccatggat taaaattagg agtcaaaacc actgctacca tgaaattccc gattgctcag   420
ggtagcatgg aagcttctac tgaatataac tttcaaaatt cttccactga tactaaaact   480
aaacaagtat catataaaag cccatcacaa aaaattaaag taccagcagg taaaacctat   540
agagttttag catacctaaa tactggatct atttcaggtg aagctaacct ttacgcaaat   600
gttgggggta tagcttgggg ggtttttacca ggttatccca atggcggagg agtaaatata   660
ggtgctgtac ttaccaaatg ccaacaaaaa ggatggggag atttcagaaa ctttcaacct   720
agtggaagag atgtaatcgt taaaggccaa ggtactttca aatctaatta tggaacggac   780
ttcattttaa aaattgaaga catcacagat tcaaagttac gaaacaataa cgggagtgga   840
actgtcgttc aagagattaa agttccacta attagaactg aaatatag                888

SEQ ID NO: 108       moltype = AA   length = 295
FEATURE              Location/Qualifiers
REGION               1..295
                     note = An amino acid sequence of a mature TIC11256 protein,
                      mTIC11256.
source               1..295
                     mol_type = protein
                     organism = synthetic construct
SEQUENCE: 108
MSSTDVQERL RDLAREDEAG TFNEAWNTNF KPSDEQQFSY SPTEGIVFLT PPKNVIGERR    60
ISQYKVNNAW ATLEGSPTEM SGTPLYAGKN VLDNSKGTSD QELLTPEFNY TYTESTSNTT   120
THGLKLGVKT TATMKFPIAQ GSMEASTEYN FQNSSTDTKT KQVSYKSPSQ KIKVPAGKTY   180
RVLAYLNTGS ISGEANLYAN VGGIAWGVLP GYPNGGGVNI GAVLTKCQQK GWGDFRNFQP   240
SGRDVIVKGQ GTFKSNYGTD FILKIEDITD SKLRNNNGSG TVVQEIKVPL IRTEI        295
```

-continued

```
SEQ ID NO: 109          moltype = DNA   length = 888
FEATURE                 Location/Qualifiers
misc_feature            1..888
                        note = A synthetic nucleotide sequence encoding a mature
                        TIC4544 protein, mTIC4544 for expression in bacteria.
source                  1..888
                        mol_type = other DNA
                        organism = synthetic construct
SEQUENCE: 109
atgtcatcca cagatgttca agaaagatta cgggacttgg caagagaaga tgaagctgga   60
acctttaatg aagcatggaa tactaacttc aaacccagtg atgaacaaca attctcgtat   120
agtccaactg aaggaattgt tttcttaaca ccacctaaaa atgttattgg cgaaagaaga   180
atttcacagt ataaagtaaa taatgcatgg gctacattag aaggaagtcc aaccgaagta   240
tcggggacac ctttatatgc gggaaaaaac gtattagata actcaaaagg aacaatcgat   300
caagagctgt taacacccga gtttagttat acctatacgg aaagcacttc aaatacaaca   360
actcatggat taaaagtagg agtcaaaacc actgctacca tgaaattccc gattgctcag   420
ggtagcatgg aagcttctac tgaatataac tttcaaaatt cttccactga tactaaaact   480
aaacaagtat catataaaag cccatcacaa aaaattaaag taccagcagg taaaaccttt   540
agagttttag catacctaaa tactggatct atttcaggtg aagctaacct ttacgcaaat   600
gttgggggta tagcttggag ggtttcacca ggttatccca atggcggagg agtaaaatata   660
ggtgctgtac ttatcaaatg ccaacaaaaa ggatgggggag atttcagaaa ctttcaacct   720
agtggaagag atgtaatcgt taaaggccaa ggtactttca aatctaatta tggaacggac   780
ttcattttaa aaattgaaga catcacagat tcaaagttac gaaacaataa cgggagtgga   840
actgtcgttc aagagattaa agttccacta attagaactg aaatatag             888

SEQ ID NO: 110          moltype = AA   length = 295
FEATURE                 Location/Qualifiers
REGION                  1..295
                        note = An amino acid sequence of a mature TIC4544 protein,
                        mTIC4544.
source                  1..295
                        mol_type = protein
                        organism = synthetic construct
SEQUENCE: 110
MSSTDVQERL RDLAREDEAG TFNEAWNTNF KPSDEQQFSY SPTEGIVFLT PPKNVIGERR   60
ISQYKVNNAW ATLEGSPTEV SGTPLYAGKN VLDNSKGTID QELLTPEFSY TYTESTSNTT   120
THGLKVGVKT TATMKFPIAQ GSMEASTEYN FQNSSTDTKT KQVSYKSPSQ KIKVPAGKTY   180
RVLAYLNTGS ISGEANLYAN VGGIAWRVSP GYPNGGGVNI GAVLIKCQQK GWGDFRNFQP   240
SGRDVIVKGQ GTFKSNYGTD FILKIEDITD SKLRNNNGSG TVVQEIKVPL IRTEI       295

SEQ ID NO: 111          moltype = DNA   length = 888
FEATURE                 Location/Qualifiers
misc_feature            1..888
                        note = A synthetic nucleotide sequence encoding a mature
                        TIC4545 protein, mTIC4545 for expression in bacteria.
source                  1..888
                        mol_type = other DNA
                        organism = synthetic construct
SEQUENCE: 111
atgtcatcca cagatgttca agaaagatta cgggacttgg caagagaaga tgaagctgga   60
accctttaatg aagcatggaa tactaacttc aaacccagtg atgaacaaca attctcttat   120
agtccaactg aaggaattgt tttcttaaca ccacctaaaa atgttattgg cgaaagaaga   180
atttcacagt ataaagtaaa taatgcatgg gctacattag aaggaagtcc aaccgaagta   240
tcggggacac ctttatatgc gggaaaaaac gtattagata actcaaaagg aacaatggat   300
caagagctgt taacacccga gtttaactat acctatacgg aaagcacttc aaatacaata   360
actcatggat taaaattagg agtcaaaacc actgctacca tgaaattccc gattgctcag   420
ggtagcatgg aagcttctac tgaatataac tttcaaaatt cttccactga tactaaaact   480
aaacaagtat catataaaag cccatcacaa aaaattaaag taccagcagg taaaaccttt   540
agagttttag catacctaaa tactggatct atttcaggtg aagctaacct ttacgcaaat   600
gttgggggta tagcttgggg ggtttcacca ggttatccca atggcggagg agtaaaatata   660
ggtgctgtac ttaccaaatg ccaacaaaaa ggatgggggag atttcagaaa ctttcaacct   720
agtggaagag atgtaatcgt taaaggccaa ggtactttcg aatctaatta tggaacggac   780
ttcattttaa aaattgaaga catcacagat tcaaagttac gaaacaataa cgggagtgga   840
actgtcgttc aagagattaa agttccacta attagaactg aaatatag             888

SEQ ID NO: 112          moltype = AA   length = 295
FEATURE                 Location/Qualifiers
REGION                  1..295
                        note = An amino acid sequence of a mature TIC4545 protein,
                        mTIC4545.
source                  1..295
                        mol_type = protein
                        organism = synthetic construct
SEQUENCE: 112
MSSTDVQERL RDLAREDEAG TFNEAWNTNF KPSDEQQFSY SPTEGIVFLT PPKNVIGERR   60
ISQYKVNNAW ATLEGSPTEV SGTPLYAGKN VLDNSKGTID QELLTPEFSY TYTESTSNTT   120
THGLKVGVKT TATMKFPIAQ GSMEASTEYN FQNSSTDTKT KQVSYKSPSQ KIKVPAGKTY   180
RVLAYLNTGS ISGEANLYAN VGGIAWRVSP GYPNGGGVNI GAVLIKCQQK GWGDFRNFQP   240
SGRDVIVKGQ GTFKSNYGTD FILKIEDITD SKLRNNNGSG TVVQEIKVPL IRTEI       295
```

```
SEQ ID NO: 113          moltype = DNA  length = 888
FEATURE                 Location/Qualifiers
misc_feature            1..888
                        note = A synthetic nucleotide sequence encoding a mature
                         TIC6871 protein, mTIC6871 for expression in bacteria.
source                  1..888
                        mol_type = other DNA
                        organism = synthetic construct
SEQUENCE: 113
atgtcatcca cagatgttca agaaagatta cgggacttgg caagagaaga tgaagctgga  60
acctttaatg aagcatggaa tactaacttc aaacccagtg atgaacaaca attctcgtat  120
agtccaactg aaggaattgt tttcttaaca ccacctaaaa atgttattgg cgaaagaaga  180
atttcacagt ataaagtaaa taatgcatgg gctacattag aaggaagtcc aaccgaagta  240
tcggggacac ctttatatgc gggaaaaaac gtattagata actcaaaagg aacaatcgat  300
caagagctgt taacacccga gtttagttat acctatacgg aaagcacttc aaatacaaca  360
actcatggat taaaattagg agtcaaaacc actgctacca tgaaattccc gattgctcag  420
ggtagcatgg aagcttctac tgaatataac tttcaaaatt cttccactga tactaaaact  480
aaacaagtat catataaaag cccatcacaa aaaattaaag taccagcagg taaaacctat  540
agagttttag catacctaaa tactggatct atttcaggtg aagctaacct ttacgcaaat  600
gttgggggta tagcttggag ggtttcacca ggttatccca atggcggagg agtaaatata  660
ggtgctgtac ttaccaaatg ccaacaaaaa ggatgggag atttcagaaa ctttcaacct  720
agtggaagag atgtaatcgt taaaggccaa ggtactttca aatctaatta tggaacggac  780
ttcattttaa aaattgaaga catcacagat tcaaagttac gaaacaataa cgggagtgga  840
actgtcgttc aagagattaa agttccacta attagaactg aaatatag              888
```

```
SEQ ID NO: 114          moltype = AA  length = 295
FEATURE                 Location/Qualifiers
REGION                  1..295
                        note = An amino acid sequence of a mature TIC6871 protein,
                         mTIC6871.
source                  1..295
                        mol_type = protein
                        organism = synthetic construct
SEQUENCE: 114
MSSTDVQERL RDLAREDEAG TFNEAWNTNF KPSDEQQFSY SPTEGIVFLT PPKNVIGERR  60
ISQYKVNNAW ATLEGSPTEV SGTPLYAGKN VLDNSKGTID QELLTPEFSY TYTESTSNTT  120
THGLKLGVKT TATMKFPIAQ GSMEASTEYN FQNSSTDTKT KIKVPAGKTY  180
RVLAYLNTGS ISGEANLYAN VGGIAWRVSP GYPNGGGVNI GAVLTKCQQK GWGDFRNFQP  240
SGRDVIVKGQ GTFKSNYGTD FILKIEDITD SKLRNNNGSG TVVQEIKVPL IRTEI       295
```

```
SEQ ID NO: 115          moltype = DNA  length = 888
FEATURE                 Location/Qualifiers
misc_feature            1..888
                        note = A synthetic nucleotide sequence encoding a mature
                         TIC7429 protein, mTIC7429 for expression in bacteria.
source                  1..888
                        mol_type = other DNA
                        organism = synthetic construct
SEQUENCE: 115
atgtcatcca cagatgttca agaacgatta cgggacttgg caagagaaga tgaagctgga  60
acccttaatg aagcatggaa tactaacttc aaacccagtg atgaacaaca attctcttat  120
agtccaactg aaggaattgt tttcttaaca ccacctaaaa atgttattgg cgaaagaaga  180
atttcacagt ataaagtaaa taatgcatgg gctacattag aaggaagtcc aaccgaagta  240
tcggggacac ctttatatgc gggaaaaaac gtattagata actcaaaagg aacaatggat  300
caagagctgt taacacccga gtttaactat acctatacgg aaagcacttc aaatacaaca  360
actcatggat taaaattagg agtcaaaacc actgctacca tgaaattccc gattgctcag  420
ggtagcatgg aagcttctac tgaatataac tttcaaaatt cttccactga tactaaaact  480
aaacaagtat catataaaag cccatcacaa aaaattaaag taccagcagg taaaacctat  540
agagttttag catacctaaa tactggatct atttcaggtg aagctaacct ttacgcaaat  600
gttgggggta tagcttggag ggtttcacca ggttatccca atggcggagg agtaaatata  660
ggtgctgtac ttaccaaatg ccaacaaaaa ggatggggag atttcagaaa ctttcaacct  720
agtggaagag atgtaatcgt taaaggccaa ggtactttca catctaatta tggaacggac  780
ttcattttaa aaattgaaga catcacagat tcaaagttac gaaacaataa cgggagtgga  840
actgtcgttc aagagattaa agttccacta attagaactg aaatatag              888
```

```
SEQ ID NO: 116          moltype = AA  length = 295
FEATURE                 Location/Qualifiers
REGION                  1..295
                        note = An amino acid sequence of a mature TIC7429 protein,
                         mTIC7429.
source                  1..295
                        mol_type = protein
                        organism = synthetic construct
SEQUENCE: 116
MSSTDVQERL RDLAREDEAG TLNEAWNTNF KPSDEQQFSY SPTEGIVFLT PPKNVIGERR  60
ISQYKVNNAW ATLEGSPTEV SGTPLYAGKN VLDNSKGTMD QELLTPEFNY TYTESTSNTT  120
THGLKLGVKT TATMKFPIAQ GSMEASTEYN FQNSSTDTKT KQVSYKSPSQ KIKVPAGKTY  180
RVLAYLNTGS ISGEANLYAN VGGIAWRVSP GYPNGGGVNI GAVLTKCQQK GWGDFRNFQP  240
```

```
SGRDVIVKGQ GTFTSNYGTD FILKIEDITD SKLRNNNGSG TVVQEIKVPL IRTEI      295

SEQ ID NO: 117          moltype = DNA  length = 888
FEATURE                 Location/Qualifiers
misc_feature            1..888
                        note = A synthetic nucleotide sequence encoding a mature
                        TIC7497 protein, mTIC7497 for expression in bacteria.
source                  1..888
                        mol_type = other DNA
                        organism = synthetic construct
SEQUENCE: 117
atgtcatcca cagatgttca agaaagatta cgggacttgg caagagaaga tgaagctgga   60
acctttaatg aagcatggaa tactaacttc aaacccagtg atcaacaaca attctcttat  120
agtccaactg aaggaattgt tttcttaaca ccacctaaca atgttattgg cgaaagaaga  180
atttcacagt ataaagtaaa taatgcatgg gctacattag aaggaagtcc aaccgaagta  240
tcggggacac ctttatatgc gggaaaaaac gtattagata actcaaaagg aacaatggat  300
caagagctgt taacacccga gtttaactat acctatacgg aaagcacttc aaatacaaca  360
actcatggat taaaagtagg agtcaaaacc actgctacca tgaaattccc gattgctcag  420
ggtagcatgg aagcttctac tgaatataac tttcaaaatt cttccactga tactaaaact  480
aaacaagtat catataaaag cccatcacaa aagattaaag taccagcagg taaaaccttt  540
agagtttttag catacctaaa tactggatct atttcaggtg aagctaacct ttacgcaaat  600
gttgggggta tagcttggag ggtttcacca ggttatccca atggcggagg agtaaatata  660
ggtgctgtac ttaccaaatg ccaacaaaaa ggatggggag atttcagaaa ctttcaacct  720
agtggaagag atgtaatcgt taaaggccaa ggtactttca aatctaatta tggaacggac  780
ttcattttaa aaattgaaga catcacagat tcaaagttac gaaacaataa cgggagtgga  840
actgtcgttc aagagattaa agttccacta attagaactg aaatatag              888

SEQ ID NO: 118          moltype = AA  length = 295
FEATURE                 Location/Qualifiers
REGION                  1..295
                        note = An amino acid sequence of a mature TIC7497 protein,
                        mTIC7497.
source                  1..295
                        mol_type = protein
                        organism = synthetic construct
SEQUENCE: 118
MSSTDVQERL RDLAREDEAG TFNEAWNTNF KPSDQQQFSY SPTEGIVFLT PPKNVIGERR   60
ISQYKVNNAW ATLEGSPTEV SGTPLYAGKN VLDNSKGTMD QELLTPEFNY TYTESTSNTT  120
THGLKVGVKT TATMKFPIAQ GSMEASTEYN FQNSSTDTKT KQVSYKSPSQ KIKVPAGKTF  180
RVLAYLNTGS ISGEANLYAN VGGIAWRVSP GYPNGGGVNI GAVLTKCQQK GWGDFRNFQP  240
SGRDVIVKGQ GTFKSNYGTD FILKIEDITD SKLRNNNGSG TVVQEIKVPL IRTEI      295

SEQ ID NO: 119          moltype = DNA  length = 888
FEATURE                 Location/Qualifiers
misc_feature            1..888
                        note = A synthetic nucleotide sequence encoding a mature
                        TIC7511 protein, mTIC7511 for expression in bacteria.
source                  1..888
                        mol_type = other DNA
                        organism = synthetic construct
SEQUENCE: 119
atgtcatcca cagatgttca agaaagatta cgggacttgg caagagaaga tgaagctgga   60
acctttaatg aagcatggaa tactaacttc aaacccagtg atcaacaaca attctcttat  120
agtccaactg aaggaattgt tttcttaaca ccacctaaaa atgttattgg cgaaagaaga  180
atttcacagt ataaagtaaa taatgcatgg gctacattag aaggaagtcc aaccgaagta  240
tcggggacac ctttatatgt gggaaaaaac gtattagata actcaaaagg aacaagcgat  300
caagagctgt taacacccga gtttaactat acctatacgg aaagcacttc aaatacaaca  360
actcatggat taaaagtagg agtcaaaacc actgctacca tgaaattccc gattgctcag  420
ggtagcatgg aagcttctac tgaatataac tttcaagatt cttccactga tactacaact  480
aaacaagtat catataaaag cccatcacaa aagattaaag taccagcagg taaaacctttt  540
agagtttttag catacctaaa tactggatct atttcaggtg aagctaacct ttacgcaaat  600
gttgggggta tagcttggag ggtttcacca ggttatccca atggcggagg agtaaatata  660
ggtgctgtac ttaccaaatg ccaacaaaaa ggatggggag atttcagaaa ctttcaacct  720
agtggaagag atgtaatcgt taaaggccaa ggtacattca aatctaatta tggaacggac  780
ttcattttaa aaattgaaga catcacagat tcaaagttac gaaacaataa cgggagtgga  840
actgtcgttc aagagattaa agttccacta attagaactg aaatatag              888

SEQ ID NO: 120          moltype = AA  length = 295
FEATURE                 Location/Qualifiers
REGION                  1..295
                        note = An amino acid sequence of a mature TIC7511 protein,
                        mTIC7511.
source                  1..295
                        mol_type = protein
                        organism = synthetic construct
SEQUENCE: 120
MSSTDVQERL RDLAREDEAG TFNEAWNTNF KPSDQQQFSY SPTEGIVFLT PPKNVIGERR   60
ISQYKVNNAW ATLEGSPTEV SGTPLYVGKN VLDNSKGTSD QELLTPEFNY TYTESTSNTT  120
THGLKVGVKT TATMKFPIAQ GSMEASTEYN FQDSSTDTTT KTVSYKSPSQ KIKVPAGKTF  180
```

```
RVLAYLNTGS ISGEANLYAN VGGIAWRVSP GYPNGGGVNI GAVLTKCQQK GWGDFRNFQP  240
SGRDVIVKGQ GTFKSNYGTD FILKIEDITD SKLRNNNGSG TVVQEIKVPL IRTEI        295

SEQ ID NO: 121          moltype = DNA  length = 888
FEATURE                 Location/Qualifiers
misc_feature            1..888
                        note = A synthetic nucleotide sequence encoding a mature
                         TIC7513 protein, mTIC7513 for expression in bacteria.
source                  1..888
                        mol_type = other DNA
                        organism = synthetic construct
SEQUENCE: 121
atgtcatcca cagatgttca agaaagatta cgggacttgg caagagaaga tgaagctgga  60
acctttaatg aagcatggaa tactaacttc aaacccagtg atgaacaaca attctcttat  120
agtccaactg aaggaattgt tttcttaaca ccacctaaaa atgttattgg cgaaagaaga  180
atttcacagt ataaagtaaa taatgcatgg gctacattag aaggaagtcc aaccgaagca  240
tcggggacac ctttatatgc gggaaaaaac gtattagata actcaaaagg aacaatggat  300
caagagctgt taacacccga gtttaactat acctatacgg aaagcacttc aaatacaaca  360
acccatggat taaaattagg agtcaaaacc actgctacca tgaaattccc gattgctcag  420
ggtagcatgg aagcttctac tgaatataac tttcaaaatt cttccactga tactaaaact  480
aaacaagtat catataaaag cccatcacaa aaaattaaag taccagcagg taaaacctat  540
agagttttag catacctaaa tactggatct atttcaggtg aagctaacct ttacgcaaat  600
gttggggggta tagcttggag ggtttcacca ggttatccca atggcggagg agtaaatata  660
ggtgctgtac ttaccaaatg ccaacaaaaa ggatggggag atttcagaaa ctttcaacct  720
agtggaagag atgtaatcgt taaaggccaa ggtactttca aatctaatta tggaacggac  780
ttcatttttaa aaattgaaga catcacagat tcaaagttac gaaacaataa cgggagtgga  840
actgtcgttc aagagattaa agttccacta attagaactg aaatatag              888

SEQ ID NO: 122          moltype = AA  length = 295
FEATURE                 Location/Qualifiers
REGION                  1..295
                        note = An amino acid sequence of a mature TIC7513 protein,
                         mTIC7513.
source                  1..295
                        mol_type = protein
                        organism = synthetic construct
SEQUENCE: 122
MSSTDVQERL RDLAREDEAG TFNEAWNTNF KPSDEQQFSY SPTEGIVFLT PPKNVIGERR  60
ISQYKVNNAW ATLEGSPTEA SGTPLYAGKN VLDNSKGTMD QELLTPEFNY TYTESTSNTT  120
THGLKLGVKT TATMKFPIAQ GSMEASTEYN FQNSSTDTKT KQVSYKSPSQ KIKVPAGKTY  180
RVLAYLNTGS ISGEANLYAN VGGIAWRVSP GYPNGGGVNI GAVLTKCQQK GWGDFRNFQP  240
SGRDVIVKGQ GTFKSNYGTD FILKIEDITD SKLRNNNGSG TVVQEIKVPL IRTEI        295

SEQ ID NO: 123          moltype = DNA  length = 888
FEATURE                 Location/Qualifiers
misc_feature            1..888
                        note = A synthetic nucleotide sequence encoding a mature
                         TIC7518 protein, mTIC7518 for expression in bacteria.
source                  1..888
                        mol_type = other DNA
                        organism = synthetic construct
SEQUENCE: 123
atgtcatcca cagatgttca agaaagatta cgggacttgg caagagaaaa tgaagctgga  60
acccttaatg aagcatggaa tactaacttc aaacccagtg atgaacaaca attctcttat  120
agtccaactg aaggaattgt tttcttaaca ccacctaaaa atgttattgg cgaaagaaga  180
atttcacagt ataaagtaaa taatgcatgg gctacattag aaggaagtcc aaccgaagta  240
tcggggacac ctttatatgc gggaaaaaac gtattagata actcaaaagg aacaatggat  300
caagagctgt taacacccga gtttaactat acctatacgg aaagcacttc aaatacaata  360
actcatggat taaaattagg agtcaaaacc actgctacca tgaaattccc gattgctcag  420
ggtagcatgg aagcttctac tgaatataac tttcaaaatt cttccactga tactaaaact  480
aaacaagtat catataaaag cccatcacaa aaaattaaag taccagcagg taaaaccttt  540
agagttttag catacctaaa tactggatct atttcaggtg aagctaacct ttacgcaaat  600
gttggggggta tagcttgggg ggtttttacca ggttatccca atggcggagg agtaaatata  660
ggtgctgtac ttaccaaatg ccaacaaaaa ggatggggag atttcagaaa ctttcaacct  720
agtggaagag atgtaatcgt taaaggccaa ggtactttcg aatctaatta tggaacggac  780
ttcatttttaa aaattgaaga catcacagat tcaaagttac gaaacaataa cgggagtgga  840
actgtcgttc aagagattaa agttccacta attagaactg aaatatag              888

SEQ ID NO: 124          moltype = AA  length = 295
FEATURE                 Location/Qualifiers
REGION                  1..295
                        note = An amino acid sequence of a mature TIC7518 protein,
                         mTIC7518.
source                  1..295
                        mol_type = protein
                        organism = synthetic construct
SEQUENCE: 124
MSSTDVQERL RDLARENEAG TLNEAWNTNF KPSDEQQFSY SPTEGIVFLT PPKNVIGERR  60
ISQYKVNNAW ATLEGSPTEV SGTPLYAGKN VLDNSKGTMD QELLTPEFNY TYTESTSNTI  120
```

```
THGLKLGVKT TATMKFPIAQ GSMEASTEYN FQNSSTDTKT KQVSYKSPSQ KIKVPAGKTF   180
RVLAYLNTGS ISGEANLYAN VGGIAWGVLP GYPNGGGVNI GAVLTKCQQK GWGDFRNFQP   240
SGRDVIVKGQ GTFESNYGTD FILKIEDITD SKLRNNNGSG TVVQEIKVPL IRTEI        295

SEQ ID NO: 125           moltype = DNA  length = 888
FEATURE                  Location/Qualifiers
misc_feature             1..888
                         note = A synthetic nucleotide sequence encoding a mature
                          TIC7524 protein, mTIC7524 for expression in bacteria.
source                   1..888
                         mol_type = other DNA
                         organism = synthetic construct
SEQUENCE: 125
atgtcatcca cagatgttca agaaagatta cgggacttgg caagagaaga tgaagctgga   60
acctttaatg aagcatggaa tactaacttc aaacccagtg atgaacaaca attctcttat   120
agtccaactg aaggaattgt tttcttaaca ccacctaaaa atgttattgg cgaaagaaga   180
atttcacagt ataaagtaaa taatgcatgg gctacattag aaggaagtcc aaccgaagca   240
tcggggacac ctttatatgc gggaaaaaac gtattagata actcaaaagg aacaatggat   300
caagagctgt taacacccga gtttaactat acctatacgg aaagcacttc aaatacaaca   360
acccatggat taaaattagg agtcaaaacc actgctacca tgaaattccc gattgctcag   420
ggtagcatgg aagcttctac tgaatataac tttcaaaatt cttccactga tactaaaact   480
aaacaagtat catataaaag cccatcacaa aaaattaaag taccagcagg taaaacctat   540
agagtttttag catacctaaa tactggatct atttcaggtg aagctaacct ttacgcaaat   600
gttgggggta tagcttggag ggtttcacca ggttatccca atggcggagg agtaaatata   660
ggtgctgtac ttaccaaatg ccaacaaaaa ggatggggag atttcagaaa ctttcaacct   720
agtggaagag atgtaatcgt taaaggccaa ggtactttcg aatctaatta tggaacggac   780
ttcatttttaa aaattgaaga catcacagat tcaaagttac gaaacaataa cgggagtgga   840
actgtcgttc aagagattaa agttccacta attagaactg aaatatag              888

SEQ ID NO: 126           moltype = AA  length = 295
FEATURE                  Location/Qualifiers
REGION                   1..295
                         note = An amino acid sequence of a mature TIC7524 protein,
                          mTIC7524
source                   1..295
                         mol_type = protein
                         organism = synthetic construct
SEQUENCE: 126
MSSTDVQERL RDLAREDEAG TFNEAWNTNF KPSDEQQFSY SPTEGIVFLT PPKNVIGERR   60
ISQYKVNNAW ATLEGSPTEA SGTPLYAGKN VLDNSKGTMD QELLTPEFNY TYTESTSNTT   120
THGLKLGVKT TATMKFPIAQ GSMEASTEYN FQNSSTDTKT KQVSYKSPSQ KIKVPAGKTY   180
RVLAYLNTGS ISGEANLYAN VGGIAWRVSP GYPNGGGVNI GAVLTKCQQK GWGDFRNFQP   240
SGRDVIVKGQ GTFESNYGTD FILKIEDITD SKLRNNNGSG TVVQEIKVPL IRTEI        295

SEQ ID NO: 127           moltype = DNA  length = 888
FEATURE                  Location/Qualifiers
misc_feature             1..888
                         note = A synthetic nucleotide sequence encoding a mature
                          TIC7526 protein, mTIC7526 for expression in bacteria.
source                   1..888
                         mol_type = other DNA
                         organism = synthetic construct
SEQUENCE: 127
atgtcatcca cagatgttca agaaagatta cgggacttag caagagaaaa tgaagctgga   60
accttaatg aagcatggaa tactaacttc aaacccagtg atgaacaaca attctcttat    120
agtccaactg aaggtattgt tttcttaaca ccacctaaaa atgttattgg cgaaagaaga   180
atttcacagt ataaagtaaa taatgcatgg gctacattag aaggaagtcc aatcgaagta   240
tcggggacac ctttatatgc gggaaaaaac gtattagata actcaaaagg aacaatggat   300
caagagctgt taacacccga gtttaactat acctatacgg aaagcacttc aaatacaata   360
actcatggat taaaattagg agtcaaaacc actgctacca tgaaattccc gattgctcag   420
ggtagcatgg aagcttctac tgaatataac tttcaaaatt cttccactga tactaaaact   480
aaacaagtat catataaaag cccatcacaa aaaattaaag taccagcagg taaaaccttt   540
agagtttttag catacctaaa tactggatct atttcaggtg aagctaacct ttacgcaaat   600
gttgggggta tagcttgggg ggttttacca ggttatccca atggcggagg agtaaatata   660
ggtgctgtac ttaccaaatg ccaacaaaaa ggatggggag atttcagaaa ctttcaacct   720
agtggaagag atgtaatcgt taaaggccaa ggtactttcg aatctaatta tggaacggac   780
ttcatttttaa aaattgaaga catcacagat tcaaagttac gaaacaataa cgggagtgga   840
actgtcgttc aagagattaa agttccacta attagaactg aaatatag              888

SEQ ID NO: 128           moltype = AA  length = 295
FEATURE                  Location/Qualifiers
REGION                   1..295
                         note = An amino acid sequence of a mature TIC7526 protein,
                          mTIC7526.
source                   1..295
                         mol_type = protein
                         organism = synthetic construct
SEQUENCE: 128
MSSTDVQERL RDLARENEAG TLNEAWNTNF KPSDEQQFSY SPTEGIVFLT PPKNVIGERR   60
```

```
ISQYKVNNAW ATLEGSPIEV SGTPLYAGKN VLDNSKGTMD QELLTPEFNY TYTESTSNTI  120
THGLKLGVKT TATMKFPIAQ GSMEASTEYN FQNSSTDTKT KQVSYKSPSQ KIKVPAGKTF  180
RVLAYLNTGS ISGEANLYAN VGGIAWGVLP GYPNGGGVNI GAVLTKCQQK GWGDFRNFQP  240
SGRDVIVKGQ GTFESNYGTD FILKIEDITD SKLRNNNGSG TVVQEIKVPL IRTEI       295

SEQ ID NO: 129          moltype = DNA   length = 888
FEATURE                 Location/Qualifiers
misc_feature            1..888
                        note = A synthetic nucleotide sequence encoding a mature
                         TIC7528 protein, mTIC7528 for expression in bacteria.
source                  1..888
                        mol_type = other DNA
                        organism = synthetic construct
SEQUENCE: 129
atgtcatcca cagatgttca agaaagatta cgggacttgg caagagaaga tgaagctgga  60
acctttaatg aagcatggaa tactaacttc aaacccagtg atcaacaaca attctcttat  120
agtccaactg aaggaattgt tttcttaaca ccacctaaaa atgttattgg cgaaagaaga  180
atttcacagt ataaagtaaa taatgcatgg gctacattag aaggaagtcc aaccgaagta  240
tcggggacac ctttatatgc gggaaaaaac gtattagata actcaaaagg aacaatggat  300
caagagctgt taacacccga gtttaactat acctatacgg aaagcacttc aaatacaaca  360
actcatggat taaaattagg agtcaaaacc actgctacca tgaaattccc gattgctcag  420
ggtagcatgg aagcttctac tgaatataac tttcaaaatt cttccactga tactaaaact  480
aaacaagtat catataaaag cccatcacaa aagattaaag taccagcagg taaaaccttt  540
agagtttttag catacctaaa tactggatct atttcaggtg aagctaacct ttacgcaaat  600
gttgggggta tagcttggag ggtttcacca ggttatccca atggcggagg agtaaatata  660
ggtgctgtac ttaccaaatg ccaacaaaaa ggatgggagt atttcagaaa ctttcaacct  720
agtggaagag atgtaatcgt taaaggccaa ggtactttca aatctaatta tggaacggac  780
ttcattttaa aaattgaaga catcacagat tcaaagttac gaaacaataa cgggagtgga  840
actgtcgttc aagagattaa agttccacta attagaactg aaatatag              888

SEQ ID NO: 130          moltype = AA   length = 295
FEATURE                 Location/Qualifiers
REGION                  1..295
                        note = An amino acid sequence of a mature TIC7528 protein,
                         mTIC7528.
source                  1..295
                        mol_type = protein
                        organism = synthetic construct
SEQUENCE: 130
MSSTDVQERL RDLAREDEAG TFNEAWNTNF KPSDQQQFSY SPTEGIVFLT PPKNVIGERR  60
ISQYKVNNAW ATLEGSPTEV SGTPLYAGKN VLDNSKGTMD QELLTPEFNY TYTESTSNTT  120
THGLKLGVKT TATMKFPIAQ GSMEASTEYN FQNSSTDTKT KQVSYKSPSQ KIKVPAGKTF  180
RVLAYLNTGS ISGEANLYAN VGGIAWRVSP GYPNGGGVNI GAVLTKCQQK GWGDFRNFQP  240
SGRDVIVKGQ GTFKSNYGTD FILKIEDITD SKLRNNNGSG TVVQEIKVPL IRTEI       295

SEQ ID NO: 131          moltype = DNA   length = 888
FEATURE                 Location/Qualifiers
misc_feature            1..888
                        note = A synthetic nucleotide sequence encoding a mature
                         TIC7535 protein, mTIC7535 for expression in bacteria.
source                  1..888
                        mol_type = other DNA
                        organism = synthetic construct
SEQUENCE: 131
atgtcatcca cagatgttca agaaagatta cgggacttgg caagagaaga tgaagctgga  60
acctttaatg aagcatggaa tactaacttc aaacccagtg atcaacaaca attctcttat  120
agtccaactg aaggaattgt tttcttaaca ccacctaaaa atgttattgg cgaaagaaga  180
atttcacagt ataaagtaaa taatgcatgg gctacattag aaggaagtcc aaccgaagca  240
tcggggacac ctttatatgc gggaaaaaac gtattagata actcaaaagg aacaatggat  300
caagagctgt taacacccga gtttagttat acctatacgg aaagcacttc aaatacaaca  360
acccatggat taaaattagg agtcaaaacc actgctacca tgaaattccc gattgctcag  420
ggtagcatgg aagcttctac tgaatataac tttcaaaatt cttccactga tactaaaact  480
aaacaagtat catataaaag cccatcacaa aaaattaaag taccagcagg taaaacctat  540
agagtttttag catacctaaa tactggatct atttcaggtg aagctaacct ttacgcaaat  600
gttgggggta tagcttggag ggtttcacca ggttatccca atggcggagg agtaaatata  660
ggtgctgtac ttaccaaatg ccaacaaaaa ggatggggag atttcagaaa ctttcaacct  720
agtggaagag atgtaatcgt taaaggccaa ggtactttca aatctaatta tggaacggac  780
ttcattttaa aaattgaaga catcacagat tcaaagttac gaaacaataa cgggagtgga  840
actgtcgttc aagagattaa agttccacta attagaactg aaatatag              888

SEQ ID NO: 132          moltype = AA   length = 295
FEATURE                 Location/Qualifiers
REGION                  1..295
                        note = An amino acid sequence of a mature TIC7535 protein,
                         mTIC7535.
source                  1..295
                        mol_type = protein
                        organism = synthetic construct
SEQUENCE: 132
```

-continued

```
MSSTDVQERL RDLAREDEAG TFNEAWNTNF KPSDQQQFSY SPTEGIVFLT PPKNVIGERR   60
ISQYKVNNAW ATLEGSPTEA SGTPLYAGKN VLDNSKGTMD QELLTPEFSY TYTESTSNTT  120
THGLKLGVKT TATMKFPIAQ GSMEASTEYN FQNSSTDTKT KQVSYKSPSQ KIKVPAGKTY  180
RVLAYLNTGS ISGEANLYAN VGGIAWRVSP GYPNGGGVNI GAVLTKCQQK GWGDFRNFQP  240
SGRDVIVKGQ GTFKSNYGTD FILKIEDITD SKLRNNNGSG TVVQEIKVPL IRTEI       295
```

INSECT INHIBITORY PROTEINS

REFERENCE TO RELATED APPLICATIONS

This application is a divisional of and claims the benefit of co-pending U.S. patent application Ser. No. 17/485,853 filed Sep. 27, 2021, which is a divisional of and claims the benefit of U.S. patent application Ser. No. 16/205,426 filed Nov. 30, 2018, now U.S. Pat. No. 11,130,964, which is a continuation-in-part of and claims the benefit of U.S. patent application Ser. No. 14/945,140, filed Nov. 18, 2015, now U.S. Pat. No. 10,662,439, which claims the benefit of priority to U.S. Provisional Application No. 62/082,504, filed Nov. 20, 2014, the entire disclosure of each of which is incorporated herein by reference in its entirety.

INCORPORATION OF SEQUENCE LISTING

A computer readable form of the Sequence Listing is filed herewith by electronic submission. The Sequence Listing is incorporated by reference in its entirety, is contained in the file created on Dec. 22, 2023, having the file name "MONS387USCP1D2_ST26" and which is 261,886 bytes in size (as measured in MS-Windows operating system).

FIELD OF THE INVENTION

The invention generally relates to the field of insect inhibitory proteins. A novel class of proteins exhibiting insect inhibitory activity against agriculturally-relevant pests of crop plants and seeds is disclosed. In particular, the disclosed class of proteins is insecticidally active against agriculturally-relevant pests of crop plants and seeds, particularly Lepidopteran and Coleopteran species of insect pests. Plants, plant parts, and seeds containing a recombinant polynucleotide construct encoding one or more of the disclosed toxin proteins are provided.

BACKGROUND OF THE INVENTION

Improving crop yield from agriculturally significant plants including, among others, corn, soybean, sugarcane, rice, wheat, vegetables, and cotton, has become increasingly important. In addition to the growing need for agricultural products to feed, clothe and provide energy for a growing human population, climate-related effects and pressure from the growing population to use land other than for agricultural practices are predicted to reduce the amount of arable land available for farming. These factors have led to grim forecasts of food security, particularly in the absence of major improvements in plant biotechnology and agronomic practices. In light of these pressures, environmentally sustainable improvements in technology, agricultural techniques, and pest management are vital tools to expand crop production on the limited amount of arable land available for farming.

Insects, particularly insects within the order Lepidoptera and Coleoptera, are considered a major cause of damage to field crops, thereby decreasing crop yields over infested areas. Lepidopteran pest species which negatively impact agriculture include, but are not limited to, *Helicoverpa zea, Ostrinia nubilalis, Diatraea saccharalis, Diatraea grandiosella, Anticarsia gemmatalis, Spodoptera frugiperda, Spodoptera exigua, Agrotis ipsilon, Trichoplusia ni, Chrysodeixis includens, Heliothis virescens, Plutella xylostella, Pectinophora gossypiella, Helicoverpa armigera, Elasmopalpus lignosellus, Striacosta albicosta* and *Phyllocnistis*

*citrella.* Coleopteran pest species which negatively impact agriculture include, but are not limited to, *Agriotes* spp., *Anthonomus* spp., *Atomaria linearis, Chaetocnema tibialis, Cosmopolites* spp., *Curculio* spp., *Dermestes* spp., *Diabrotica* spp., *Epilachna* spp., *Eremnus* spp., *Leptinotarsa decemlineata, Lissorhoptrus* spp., *Melolontha* spp., *Orycaephilus* spp., *Otiorhynchus* spp., *Phlyctinus* spp., *Popillia* spp., *Psylliodes* spp., *Rhizopertha* spp., Scarabeidae, *Sitophilus* spp., *Sitotroga* spp., *Tenebrio* spp., *Tribolium* spp. and *Trogoderma* spp., particularly when the pest is *Diabrotica virgifera virgifera* (Western Corn Rootworm, WCR), *Diabrotica barberi* (Northern Corn Rootworm, NCR), *Diabrotica virgifera zeae* (Mexican Corn Rootworm, MCR), *Diabrotica* balteata (Brazilian Corn Rootworm (BZR), *Diabrotica* undecimpunctata howardii (Southern Corn Rootworm, SCR) and a Brazilian Corn Rootworm complex (BCR) consisting of *Diabrotica viridula* and *Diabrotica speciosa*).

Historically, the intensive application of synthetic chemical insecticides was relied upon as the pest control agent in agriculture. Concerns for the environment and human health, in addition to emerging resistance issues, stimulated the research and development of biological pesticides. This research effort led to the progressive discovery and use of various entomopathogenic microbial species, including bacteria.

The biological control paradigm shifted when the potential of entomopathogenic bacteria, especially bacteria belonging to the genus *Bacillus*, was discovered and developed as a biological pest control agent. Strains of the bacterium *Bacillus thuringiensis* (Bt) have been used as a source for proteins which exhibit pesticidal activity since it was discovered that Bt strains show a high toxicity against specific insects. The main feature of Bt's is the production of parasporal bodies which contain one or more crystals that contain specific insecticidal endotoxins (Cry proteins) which act upon ingestion by a susceptible insect through a pore-forming mechanism of action detrimental for the insect gut epithelium. Besides Bt, other *Bacillus* species, such as *Bacillus sphaericus*, and other bacteria species that contain genes that contribute to an entomopathogenic phenotype, such as *Brevibacillus laterosporus*, have shown potential for pest management.

Insecticidal toxin proteins have been employed in various agricultural applications to preserve agriculturally important plants and increase yields. Insecticidal toxin proteins are used to control agriculturally-relevant pests of crop plants by mechanical methods, such as spraying to disperse microbial formulations containing various bacteria strains onto plant surfaces, and by using genetic transformation techniques to produce transgenic plants and seeds expressing insecticidal toxin protein.

The use of transgenic plants expressing insecticidal toxin proteins has been globally adapted. For example, in 2012, 26.1 million hectares were planted with transgenic crops expressing Bt toxins (James, C., Global Status of Commercialized Biotech/GM Crops: 2012. ISAAA Brief No. 44). The expanded use of transgenic insect-protected crops and the limited number of commercially available insecticidal toxin proteins is creating a selection pressure for alleles that impart resistance to the currently-utilized insecticidal proteins. The development of resistance in target pests to insecticidal toxin proteins undermines the effectiveness and advantages of this technology. Such advantages include increased crop yields, reduction in chemical pesticide use, and reduction in the costs and labor associated with chemical pesticide use.

The discovery and development of new forms of insecticidal toxin proteins is central to managing the increase in insect resistance to transgenic crops expressing insecticidal toxin proteins. New protein toxins with improved efficacy and which exhibit control over a broader spectrum of susceptible insect species will reduce the number of surviving insects which can develop resistance alleles. In addition, two or more transgenic toxins toxic to the same insect pest and displaying different modes of action in one plant further reduces the probability of resistance in a target insect species.

Consequently, there is a critical need to discover and develop effective insecticidal proteins with improved insecticidal properties such as increased efficacy against a broader spectrum of target insect pest species and different modes of action compared to proteins known in the art. A novel protein toxin family from *Brevibacillus laterosporus* (*B. laterosporus*) is disclosed in this application along with similar toxin proteins, variant proteins, and exemplary recombinant proteins that exhibit insecticidal activity against significant target Lepidopteran and Coleopteran pest species, particularly against Western Corn Rootworm.

SUMMARY OF THE INVENTION

Disclosed herein is a novel group of insect inhibitory recombinant polynucleotide molecules and polypeptides (toxin proteins) encoded thereby, referred to herein as TIC3668-type proteins, which are shown to exhibit inhibitory activity against one or more pests of crop plants. Each of the proteins can be used alone or in combination with each other and with other insecticidal proteins and toxic agents in formulations and in planta, thus providing alternatives to insecticidal proteins and insecticide chemistries currently in use in agricultural systems.

In one aspect, the invention provides a recombinant polynucleotide molecule encoding an insect inhibitory polypeptide comprising an amino acid sequence selected from the group consisting of SEQ ID NO:25, SEQ ID NO:23, SEQ ID NO:24, SEQ ID NO:26, SEQ ID NO:27, SEQ ID NO:28, SEQ ID NO:29, SEQ ID NO:30, SEQ ID NO:31, SEQ ID NO:106, SEQ ID NO: 108, SEQ ID NO: 110, SEQ ID NO: 112, SEQ ID NO: 114, SEQ ID NO:116, SEQ ID NO: 118, SEQ ID NO:120, SEQ ID NO: 122, SEQ ID NO: 124, SEQ ID NO:126, SEQ ID NO: 128, SEQ ID NO:130, and SEQ ID NO:132. In one embodiment, the recombinant polynucleotide molecule encodes an insect inhibitory polypeptide comprising at least 35% identity, for instance, at least 40%, 50%, 60%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity to an amino acid sequence selected from the group consisting of SEQ ID NO:25, SEQ ID NO:23, SEQ ID NO:24, SEQ ID NO:26, SEQ ID NO:27, SEQ ID NO:28, SEQ ID NO:29, SEQ ID NO:30, SEQ ID NO:31, SEQ ID NO:106, SEQ ID NO: 108, SEQ ID NO: 110, SEQ ID NO:112, SEQ ID NO:114, SEQ ID NO:116, SEQ ID NO:118, SEQ ID NO: 120, SEQ ID NO: 122, SEQ ID NO: 124, SEQ ID NO: 126, SEQ ID NO: 128, SEQ ID NO: 130, and SEQ ID NO:132. In another embodiment, the recombinant polynucleotide molecule comprises a nucleotide sequence selected from the group consisting of SEQ ID NO:37, SEQ ID NO:33, SEQ ID NO:35, SEQ ID NO:39, SEQ ID NO:41, SEQ ID NO:43, SEQ ID NO:45, SEQ ID NO:47, SEQ ID NO:49, SEQ ID NO: 64, SEQ ID NO:65, SEQ ID NO:66, SEQ ID NO:67, SEQ ID NO:68, SEQ ID NO:69, SEQ ID NO: 70, SEQ ID NO:71, SEQ ID NO:72, SEQ ID NO: 105, SEQ ID NO: 107, SEQ ID NO: 109, SEQ ID NO: 111, SEQ ID NO: 113, SEQ ID NO:115, SEQ ID NO:117, SEQ ID NO: 119, SEQ ID NO: 121, SEQ ID NO: 123, SEQ ID NO: 125, SEQ ID NO:127, SEQ ID NO:129, and SEQ ID NO:131. In still another embodiment the recombinant polynucleotide molecule comprises at least 35% identity, for instance, at least 40%, 50%, 60%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity to a nucleotide sequence selected from the group consisting of SEQ ID NO:37, SEQ ID NO:33, SEQ ID NO:35, SEQ ID NO:39, SEQ ID NO:41, SEQ ID NO:43, SEQ ID NO:45, SEQ ID NO:47, SEQ ID NO:49, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:105, SEQ ID NO:107, SEQ ID NO: 109, SEQ ID NO: 111, SEQ ID NO: 113, SEQ ID NO: 115, SEQ ID NO: 117, SEQ ID NO: 119, SEQ ID NO: 121, SEQ ID NO: 123, SEQ ID NO: 125, SEQ ID NO: 127, SEQ ID NO: 129, and SEQ ID NO:131. In a further embodiment, the recombinant polynucleotide molecule comprise a sequence that hybridizes to: (i) the reverse complement of the nucleotide sequence from position 4-885 of a sequence selected from the group consisting of SEQ ID NO:37, SEQ ID NO:33, SEQ ID NO:35, SEQ ID NO:39, SEQ ID NO:41, SEQ ID NO:43, SEQ ID NO:45, SEQ ID NO:47, SEQ ID NO:49, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO: 105, SEQ ID NO:107, SEQ ID NO: 109, SEQ ID NO: 111, SEQ ID NO: 115, SEQ ID NO: 117, SEQ ID NO: 119, SEQ ID NO: 121, SEQ ID NO: 123, SEQ ID NO: 125, SEQ ID NO: 127, SEQ ID NO:129, and SEQ ID NO: 131; or (ii) the reverse complement a sequence selected from the group consisting of SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, and SEQ ID NO:61. In another embodiment, the hybridization conditions are stringent conditions, for instance, such stringent conditions may comprise hybridization from 4 to 12 hours in 50% formamide, 1 M NaCl, and 1% SDS at 37 C, and a wash in 0.1×SSC at 60 C-65 C. In further embodiment, the recombinant polynucleotide molecule is operably linked to a heterologous promoter.

In another aspect, the invention provides an insect inhibitory recombinant polypeptide encoded by the recombinant polynucleotide molecule provided herein. In one embodiment, the insect inhibitory recombinant polypeptide comprises an amino acid sequence selected from the group consisting of SEQ ID NO:25, SEQ ID NO:23, SEQ ID NO:24, SEQ ID NO:26, SEQ ID NO:27, SEQ ID NO:28, SEQ ID NO:29, SEQ ID NO:30, SEQ ID NO:31, SEQ ID NO: 106, SEQ ID NO:108, SEQ ID NO:110, SEQ ID NO:112, SEQ ID NO:114, SEQ ID NO:116, SEQ ID NO:118, SEQ ID NO:120, SEQ ID NO: 122, SEQ ID NO: 124, SEQ ID NO: 126, SEQ ID NO: 128, SEQ ID NO: 130, and SEQ ID NO:132. In another embodiment, the insect inhibitory recombinant polypeptide comprises at least 35% identity, for instance, at least 40%, 50%, 60%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity to an amino acid sequence selected from the group consisting of SEQ ID NO:25, SEQ ID NO:23, SEQ ID NO:24, SEQ ID NO:26, SEQ ID NO:27, SEQ ID NO:28, SEQ ID NO:29, SEQ ID NO:30, SEQ ID NO:31, SEQ ID NO: 106, SEQ ID NO:108, SEQ ID NO:110, SEQ ID NO:112, SEQ ID NO:114, SEQ ID NO:116, SEQ ID NO:118, SEQ ID NO: 120, SEQ ID NO: 122, SEQ ID NO: 124, SEQ ID NO: 126, SEQ ID NO:128, SEQ ID NO:130, and SEQ ID NO:132.

In a further embodiment, the insect inhibitory recombinant polypeptide exhibits inhibitory activity against an insect species of the order Coleoptera, for instance including Western Corn Rootworm, Southern Corn Rootworm, Northern Corn Rootworm, Mexican Corn Rootworm, Brazilian Corn Rootworm, or Brazilian Corn Rootworm complex consisting of *Diabrotica viridula* and *Diabrotica speciosa*. In yet a further embodiment, the insect inhibitory recombinant polypeptide exhibits inhibitory activity against an insect species of the order Lepidoptera, for instance including European Corn Borer, Southwestern Corn Borer, Black Cutworm, Fall Army Worm, Corn Earworm, and Soybean Looper.

In yet another aspect, the invention provides a host cell comprising a recombinant polynucleotide molecule of the invention, wherein the host cell is selected from the group consisting of a bacterial host cell and a plant host cell. In certain embodiments, bacterial host cells include *Agrobacterium, Rhizobium, Bacillus thuringiensis, Brevibacillus lacterosporus, Bacillus cereus, E. coli, Pseudomonas, Klebsiella,* and *Erwinia*. In other embodiments, plant cells include an alfalfa, banana, barley, bean, broccoli, cabbage, *brassica*, carrot, cassava, castor, cauliflower, celery, chickpea, Chinese cabbage, citrus, coconut, coffee, corn, clover, cotton, a cucurbit, cucumber, Douglas fir, eggplant, *eucalyptus*, flax, garlic, grape, hops, leek, lettuce, Loblolly pine, millets, melons, nut, oat, olive, onion, ornamental, palm, pasture grass, pea, peanut, pepper, persimmon, pigeon pea, pine, pomegranate, poplar, potato, pumpkin, *Radiata* pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat plant cell.

In a further aspect, the invention provides an insect inhibitory composition which may comprise a recombinant polynucleotide molecule of the present invention. In one embodiment, the insect inhibitory composition may further comprise a nucleotide sequence encoding at least one other pesticidal agent. In certain embodiments, the at least one other pesticidal agent is different from the TIC3668-type insect inhibitory polypeptide of the invention and may be selected from the group consisting of an insect inhibitory protein, an insect inhibitory dsRNA molecule, and an ancillary protein. In other embodiments, the other pesticidal agent exhibits activity against one or more pest species of the orders Lepidoptera, Coleoptera, or Hemiptera. In certain embodiments, the other pesticidal agent is selected from the group consisting of a Cry1A, Cry1Ab, Cry1Ac, Cry1A.105, Cry1B, Cry1C, Cry1D, Cry1E, Cry1F, Cry1G, Cry1H, Cry1I, Cry1J, Cry1K, Cry1L, Cry2A, Cry2Ab, Cry3A, Cry3B, Cry4B, Cry6, Cry7, Cry8, Cry9, Cry15, Cry34, Cry35, Cry43A, Cry43B, Cry51Aa1, ET29, ET33, ET34, ET35, ET66, ET70, TIC400, TIC407, TIC417, TIC431, TIC800, TIC807, TIC834, TIC853, TIC900, TIC901, TIC1201, TIC1415, VIP3A, and VIP3B protein. In yet a further aspect, the present invention provides an insect inhibitory composition comprising an insect inhibitory recombinant polypeptide of the present invention, such as a TIC3668-type insect inhibitory polypeptide, in an insect inhibitory effective amount.

In still another aspect, the invention provides a method of controlling a Coleopteran or Lepidopteran species pest, and controlling a Coleopteran or Lepidopteran species pest infestation of a plant, for instance a crop plant, wherein the method comprises contacting the pest with an insect inhibitory amount of the insect inhibitory recombinant polypeptide of the invention, such as a TIC3668-type insect inhibitory polypeptide.

In a still further aspect, the invention provides a seed comprising a recombinant polynucleotide molecule or insect inhibitory recombinant polypeptide, such as a TIC3668-type insect inhibitory polypeptide, of the invention.

In another aspect, the invention provides a commodity product comprising a detectable amount of the recombinant polynucleotide molecule, or the insect inhibitory polypeptide, such as a TIC3668-type insect inhibitory polypeptide, of the invention. In a further aspect, a commodity product of the invention may comprise a host cell comprising a recombinant polynucleotide molecule of the invention, wherein the commodity product comprises a detectable amount of the recombinant polynucleotide molecule or an insect inhibitory recombinant polypeptide encoded by the recombinant polynucleotide. In certain embodiments, the commodity products may include commodity corn bagged by a grain handler, corn flakes, corn cakes, corn flour, corn meal, corn syrup, corn oil, corn silage, corn starch, corn cereal, and the like, and corresponding soybean, rice, wheat, sorghum, pigeon pea, peanut, fruit, melon, and vegetable commodity products including where applicable, juices, concentrates, jams, jellies, marmalades, and other edible forms of such commodity products containing a detectable amount of such polynucleotides and or polypeptides of this application.

In a yet another aspect, the invention provides a method of producing seed comprising the recombinant polynucleotide of the invention, wherein the method comprises: (a) planting at least one seed comprising the recombinant polynucleotide molecule; (b) growing plants from the seed; and (c) harvesting seed from the plants, wherein the harvested seed comprises the recombinant polynucleotide molecule.

In a further aspect, the invention provides a recombinant vector comprising the recombinant polynucleotide molecule of the invention. In one embodiment, the recombinant vector is selected from the group consisting of a plasmid, a bacmid, a phagemid, and a cosmid.

In another aspect, the invention provides a plant resistant to insect infestation, wherein the cells of said plant comprise the recombinant polynucleotide molecule or the insect inhibitory recombinant polypeptide of the invention.

BRIEF DESCRIPTION OF THE DRAWINGS

FIG. 1 illustrates the alignment of the collage protein TIC4260 to five exemplary TIC3668-type proteins. Positions of sequence diversity are highlighted in gray shading in this sequence alignment.

BRIEF DESCRIPTION OF THE SEQUENCES

Figure 2:
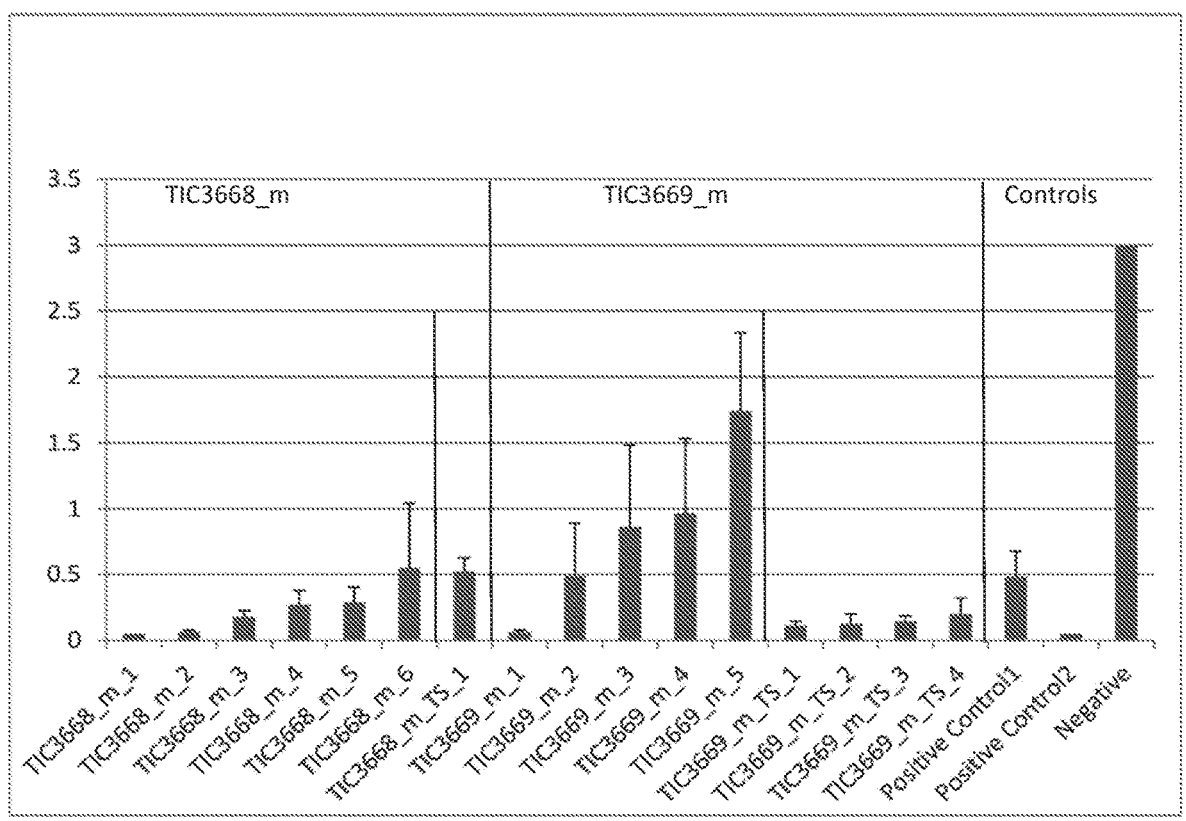
FIG. 2 illustrates in planta Western Corn Rootworm (WCR) inhibitory activity of exemplary chloroplast targeted and non-targeted mature length TIC3668-type proteins.

SEQ ID NO:1 is a recombinant polynucleotide sequence obtained from a *Brevibacillus laterosporus* species encoding a TIC3668 protein from an open reading frame at nucleotide position 1-951 and a translation termination codon.

SEQ ID NO:2 is the amino acid sequence translation of the TIC3668 precursor protein from the open reading frame as set forth in SEQ ID NO:1.

SEQ ID NO:3 is a recombinant polynucleotide sequence obtained from a *Brevibacillus laterosporus* species encoding a TIC3669 protein from an open reading frame at nucleotide position 1-951 and a translation termination codon.

SEQ ID NO:4 is the amino acid sequence translation of the TIC3669 precursor protein from the open reading frame as set forth in SEQ ID NO:3.

SEQ ID NO:5 is a recombinant polynucleotide sequence obtained from a *Brevibacillus laterosporus* species encoding a TIC3670 protein from an open reading frame at nucleotide position 1-951 and a translation termination codon.

SEQ ID NO:6 is the amino acid sequence translation of the TIC3670 precursor protein from the open reading frame as set forth in SEQ ID NO:5.

SEQ ID NO:7 is a recombinant polynucleotide sequence obtained from a *Brevibacillus laterosporus* species encoding a TIC4076 protein from an open reading frame at nucleotide position 1-951 and a translation termination codon.

SEQ ID NO:8 is the amino acid sequence translation of the TIC4076 precursor protein from the open reading frame as set forth in SEQ ID NO:7.

SEQ ID NO:9 is a recombinant polynucleotide sequence obtained from a *Brevibacillus laterosporus* species encoding a TIC4078 protein from an open reading frame at nucleotide position 1-951 and a translation termination codon.

SEQ ID NO: 10 is the amino acid sequence translation of the TIC4078 precursor protein from the open reading frame as set forth in SEQ ID NO:9.

SEQ ID NO:11 is a recombinant polynucleotide sequence obtained from a *Brevibacillus laterosporus* species encoding a collage TIC4260 protein from an open reading frame at nucleotide position 1-951 and a translation termination codon, created by combining DNA segments from each of coding sequences set forth in SEQ ID NO:1, SEQ ID NO:3, SEQ ID NO:5, SEQ ID NO:7 and SEQ ID NO:9 in-frame to include the sequence variations from these five different open reading frames.

SEQ ID NO:12 is the amino acid sequence translation of the collage protein TIC4260 precursor protein from the open reading frame as set forth in SEQ ID NO:11.

SEQ ID NO:13 is a recombinant polynucleotide sequence obtained from a *Brevibacillus laterosporus* species encoding a TIC4346 protein from an open reading frame at nucleotide position 1-951 and a translation termination codon.

SEQ ID NO:14 is the amino acid sequence translation of the TIC4346 precursor protein from the open reading frame as set forth in SEQ ID NO:13.

SEQ ID NO:15 is a recombinant polynucleotide sequence obtained from a *Brevibacillus laterosporus* species encoding a TIC4826 protein from an open reading frame at nucleotide position 1-951 and a translation termination codon.

SEQ ID NO:16 is the amino acid sequence translation of the TIC4826 precursor protein from the open reading frame as set forth in SEQ ID NO:15.

SEQ ID NO:17 is a recombinant polynucleotide sequence obtained from a *Brevibacillus laterosporus* species encoding a TIC4861 protein from an open reading frame at nucleotide position 1-918 and a translation termination codon.

SEQ ID NO:18 is the amino acid sequence translation of the TIC4861 precursor protein from the open reading frame as set forth in SEQ ID NO: 17.

SEQ ID NO:19 is a recombinant polynucleotide sequence obtained from a *Brevibacillus laterosporus* species encoding a TIC4862 protein from an open reading frame at nucleotide position 1-945 and a translation termination codon.

SEQ ID NO:20 is the amino acid sequence translation of the TIC4862 precursor protein from the open reading frame as set forth in SEQ ID NO: 19.

SEQ ID NO:21 is a recombinant polynucleotide sequence obtained from a *Brevibacillus laterosporus* species encoding a TIC4863 protein from an open reading frame at nucleotide position 1-951 and a translation termination codon.

SEQ ID NO:22 is the amino acid sequence translation of the TIC4863 precursor protein from the open reading frame as set forth in SEQ ID NO:21.

SEQ ID NO:23 is an amino acid sequence of a mature TIC3668 protein, mTIC3668.

SEQ ID NO:24 is an amino acid sequence of a mature TIC3669 protein, mTIC3669.

SEQ ID NO:25 is an amino acid sequence of a mature TIC3670 protein, mTIC3670.

SEQ ID NO:26 is an amino acid sequence of a mature TIC4076 protein, mTIC4076.

SEQ ID NO:27 is an amino acid sequence of a mature TIC4078 protein, mTIC4078.

SEQ ID NO:28 is an amino acid sequence of a mature TIC4260 protein, mTIC4260.

SEQ ID NO:29 is an amino acid sequence of a mature TIC4346 protein, mTIC4346.

SEQ ID NO:30 is an amino acid sequence of a mature TIC4826 protein, mTIC4826.

SEQ ID NO:31 is an amino acid sequence of a mature TIC4861 protein, mTIC4861.

SEQ ID NO:32 is a synthetic nucleotide sequence encoding a TIC3668 protein designed for expression in plants.

SEQ ID NO:33 is a synthetic nucleotide sequence encoding a mature TIC3668 protein, mTIC3668 designed for expression in plants.

SEQ ID NO:34 is a synthetic nucleotide sequence encoding a TIC3669 protein designed for expression in plants.

SEQ ID NO:35 is a synthetic nucleotide sequence encoding a mature TIC3669 protein, mTIC3669 designed for expression in plants.

SEQ ID NO:36 is a synthetic nucleotide sequence encoding a TIC3670 protein designed for expression in plants.

SEQ ID NO:37 is a synthetic nucleotide sequence encoding a mature TIC3670 protein, mTIC3670 designed for expression in plants.

SEQ ID NO:38 is a synthetic nucleotide sequence encoding a TIC4076 protein designed for expression in plants.

SEQ ID NO:39 is a synthetic nucleotide sequence encoding a mature TIC4076 protein, mTIC4076 designed for expression in plants.

SEQ ID NO:40 is a synthetic nucleotide sequence encoding a TIC4078 protein designed for expression in plants.

SEQ ID NO:41 is a synthetic nucleotide sequence encoding a mature TIC4078 protein, mTIC4078 designed for expression in plants.

SEQ ID NO:42 is a synthetic nucleotide sequence encoding a TIC4260 protein designed for expression in plants.

SEQ ID NO:43 is a synthetic nucleotide sequence encoding a mature TIC4260 protein, mTIC4260 designed for expression in plants.

SEQ ID NO:44 is a synthetic nucleotide sequence encoding a TIC4346 protein designed for expression in plants.

SEQ ID NO:45 is a synthetic nucleotide sequence encoding a mature TIC4346 protein, mTIC4346 designed for expression in plants.

SEQ ID NO:46 is a synthetic nucleotide sequence encoding a TIC4826 protein designed for expression in plants.

SEQ ID NO:47 is a synthetic nucleotide sequence encoding a mature TIC4826 protein, mTIC4826 designed for expression in plants.

SEQ ID NO:48 is a synthetic nucleotide sequence encoding a TIC4861 protein designed for expression in plants.

SEQ ID NO:49 is a synthetic nucleotide sequence encoding a mature TIC4861 protein (mTIC4861), a mature TIC4862 protein (mTIC4862), and a mature TIC4863 protein (mTIC4863) designed for expression in plants.

SEQ ID NO:50 is a synthetic nucleotide sequence encoding a TIC4682 protein designed for expression in plants.

SEQ ID NO:51 is a synthetic nucleotide sequence encoding a TIC4863 protein designed for expression in plants.

SEQ ID NO:52 is a nucleotide sequence representing a synthetic oligonucleotide for hybridizing to the (−) strand of a DNA encoding a protein disclosed in this application and corresponds to positions 1 to 36 of SEQ ID NO:1 (TIC3668 forward primer).

SEQ ID NO:53 is a nucleotide sequence representing a synthetic oligonucleotide for hybridizing to the (+) strand of a DNA encoding a protein disclosed in this application and corresponds to positions 920 to 954 of SEQ ID NO:1 (TIC3668 reverse primer).

SEQ ID NO:54 is a nucleotide sequence representing a synthetic oligonucleotide for hybridizing to the (−) strand of a DNA encoding a protein disclosed in this application and corresponds to positions 1 to 41 of SEQ ID NO:3 (TIC3669 forward primer).

SEQ ID NO:55 is a nucleotide sequence representing a synthetic oligonucleotide for hybridizing to the (+) strand of a DNA encoding a protein disclosed in this application and corresponds to positions 920 to 954 of SEQ ID NO:3 (TIC3669 reverse primer).

SEQ ID NO:56 is a nucleotide sequence representing a synthetic oligonucleotide for hybridizing to the (−) strand of a DNA encoding a protein disclosed in this application and corresponds to positions 1 to 36 of SEQ ID NO:5 (TIC3670 forward primer).

SEQ ID NO:57 is a nucleotide sequence representing a synthetic oligonucleotide for hybridizing to the (+) strand of a DNA encoding a protein disclosed in this application and corresponds to positions 920 to 954 of SEQ ID NO:5 (TIC3670 reverse primer).

SEQ ID NO:58 is a nucleotide sequence representing a synthetic oligonucleotide for hybridizing to the (−) strand of a DNA encoding a protein disclosed in this application and corresponds to positions 1 to 41 of SEQ ID NO:7 (TIC4076 forward primer).

SEQ ID NO:59 is a nucleotide sequence representing a synthetic oligonucleotide for hybridizing to the (+) strand of a DNA encoding a protein disclosed in this application and corresponds to positions 920 to 954 of SEQ ID NO:7 (TIC4076 reverse primer).

SEQ ID NO:60 is a nucleotide sequence representing a synthetic oligonucleotide for hybridizing to the (−) strand of a DNA encoding a protein disclosed in this application and corresponds to positions 1 to 36 of SEQ ID NO:9 (TIC4078 forward primer).

SEQ ID NO:61 is a nucleotide sequence representing a synthetic oligonucleotide for hybridizing to the (+) strand of a DNA encoding a protein disclosed in this application and corresponds to positions 920 to 954 of SEQ ID NO:9 (TIC4078 reverse primer).

SEQ ID NO:62 is a recombinant polynucleotide sequence obtained from a *Brevibacillus laterosporus* species encoding a TIC2462 protein from an open reading frame at nucleotide position 1-951 and a translation termination codon.

SEQ ID NO:63 is the amino acid sequence translation of the open reading frame as set forth in SEQ ID NO:62.

SEQ ID NO:64 is a synthetic nucleotide sequence encoding a mature TIC3668 protein, mTIC3668 for expression in bacteria.

SEQ ID NO:65 is a synthetic nucleotide sequence encoding a mature TIC3669 protein, mTIC3669 for expression in bacteria.

SEQ ID NO:66 is a synthetic nucleotide sequence encoding a mature TIC3670 protein, mTIC3670 for expression in bacteria.

SEQ ID NO:67 is a synthetic nucleotide sequence encoding a mature TIC4076 protein, mTIC4076 for expression in bacteria.

SEQ ID NO:68 is a synthetic nucleotide sequence encoding a mature TIC4078 protein, mTIC4078 for expression in bacteria.

SEQ ID NO:69 is a synthetic nucleotide sequence encoding a mature TIC4260 protein, mTIC4260 for expression in bacteria.

SEQ ID NO:70 is a synthetic nucleotide sequence encoding a mature TIC4346 protein, mTIC4346 for expression in bacteria.

SEQ ID NO:71 is a synthetic nucleotide sequence encoding a mature TIC4826 protein, mTIC4826 for expression in bacteria.

SEQ ID NO:72 is a synthetic nucleotide sequence encoding a mature TIC4861 (mTIC4861), TIC4862 (mTIC4862), and TIC4863 (mTIC4863) protein for expression in bacteria.

SEQ ID NO:73 is a recombinant polynucleotide sequence obtained from a *Brevibacillus laterosporus* species encoding a TIC11239 precursor protein from an open reading frame at nucleotide position 1-951 and a translation termination codon.

SEQ ID NO:74 is the amino acid sequence translation of the TIC11239 precursor protein from the open reading frame as set forth in SEQ ID NO:73.

SEQ ID NO:75 is a recombinant polynucleotide sequence obtained from a *Brevibacillus laterosporus* species encoding a TIC11243 precursor protein from an open reading frame at nucleotide position 1-951 and a translation termination codon.

SEQ ID NO:76 is the amino acid sequence translation of the TIC1 1243 precursor protein from the open reading frame as set forth in SEQ ID NO:75.

SEQ ID NO:77 is a recombinant polynucleotide sequence obtained from a *Brevibacillus laterosporus* species encoding a TIC11256 precursor protein from an open reading frame at nucleotide position 1-951 and a translation termination codon.

SEQ ID NO:78 is the amino acid sequence translation of the TIC11256 precursor protein from the open reading frame as set forth in SEQ ID NO:77.

SEQ ID NO:79 is a recombinant polynucleotide sequence obtained from a *Brevibacillus laterosporus* species encoding a TIC4544 precursor protein from an open reading frame at nucleotide position 1-951 and a translation termination codon.

SEQ ID NO:80 is the amino acid sequence translation of the TIC4544 precursor protein from the open reading frame as set forth in SEQ ID NO:79.

SEQ ID NO:81 is a recombinant polynucleotide sequence obtained from a *Brevibacillus laterosporus* species encoding a TIC4545 precursor protein from an open reading frame at nucleotide position 1-951 and a translation termination codon.

SEQ ID NO:82 is the amino acid sequence translation of the TIC4545 precursor protein from the open reading frame as set forth in SEQ ID NO:81.

SEQ ID NO:83 is a recombinant polynucleotide sequence obtained from a *Brevibacillus laterosporus* species encoding a TIC6871 precursor protein from an open reading frame at nucleotide position 1-951 and a translation termination codon.

SEQ ID NO:84 is the amino acid sequence translation of the TIC6871 precursor protein from the open reading frame as set forth in SEQ ID NO:83.

SEQ ID NO:85 is a recombinant polynucleotide sequence obtained from a *Brevibacillus laterosporus* species encoding a TIC7429 precursor protein from an open reading frame at nucleotide position 1-951 and a translation termination codon.

SEQ ID NO:86 is the amino acid sequence translation of the TIC7429 precursor protein from the open reading frame as set forth in SEQ ID NO:85.

SEQ ID NO:87 is a recombinant polynucleotide sequence obtained from a *Brevibacillus laterosporus* species encoding a TIC7497 precursor protein from an open reading frame at nucleotide position 1-951 and a translation termination codon.

SEQ ID NO:88 is the amino acid sequence translation of the TIC7497 precursor protein from the open reading frame as set forth in SEQ ID NO:87.

SEQ ID NO:89 is a recombinant polynucleotide sequence obtained from a *Brevibacillus laterosporus* species encoding a TIC7511 precursor protein from an open reading frame at nucleotide position 1-951 and a translation termination codon.

SEQ ID NO:90 is the amino acid sequence translation of the TIC7511 precursor protein from the open reading frame as set forth in SEQ ID NO:89.

SEQ ID NO:91 is a recombinant polynucleotide sequence obtained from a *Brevibacillus laterosporus* species encoding a TIC7513 precursor protein from an open reading frame at nucleotide position 1-951 and a translation termination codon.

SEQ ID NO:92 is the amino acid sequence translation of the TIC7513 precursor protein from the open reading frame as set forth in SEQ ID NO:91.

SEQ ID NO:93 is a recombinant polynucleotide sequence obtained from a *Brevibacillus laterosporus* species encoding a TIC7518 precursor protein from an open reading frame at nucleotide position 1-951 and a translation termination codon.

SEQ ID NO:94 is the amino acid sequence translation of the TIC7518 precursor protein from the open reading frame as set forth in SEQ ID NO:93.

SEQ ID NO:95 is a recombinant polynucleotide sequence obtained from a *Brevibacillus laterosporus* species encoding a TIC7524 precursor protein from an open reading frame at nucleotide position 1-951 and a translation termination codon.

SEQ ID NO:96 is the amino acid sequence translation of the TIC7524 precursor protein from the open reading frame as set forth in SEQ ID NO:95.

SEQ ID NO:97 is a recombinant polynucleotide sequence obtained from a *Brevibacillus laterosporus* species encoding a TIC7526 precursor protein from an open reading frame at nucleotide position 1-951 and a translation termination codon.

SEQ ID NO:98 is the amino acid sequence translation of the TIC7526 precursor protein from the open reading frame as set forth in SEQ ID NO:97.

SEQ ID NO:99 is a recombinant polynucleotide sequence obtained from a *Brevibacillus laterosporus* species encoding a TIC7528 precursor protein from an open reading frame at nucleotide position 1-951 and a translation termination codon.

SEQ ID NO: 100 is the amino acid sequence translation of the TIC7528 precursor protein from the open reading frame as set forth in SEQ ID NO:99.

SEQ ID NO: 101 is a recombinant polynucleotide sequence obtained from a *Brevibacillus laterosporus* species encoding a TIC7535 precursor protein from an open reading frame at nucleotide position 1-951 and a translation termination codon.

SEQ ID NO: 102 is the amino acid sequence translation of the TIC7535 precursor protein from the open reading frame as set forth in SEQ ID NO: 101.

SEQ ID NO: 103 is a synthetic nucleotide sequence encoding a mature TIC11239 protein, mTIC11239 for expression in bacteria.

SEQ ID NO: 104 is an amino acid sequence of a mature TIC11239 protein, mTIC11239.

SEQ ID NO:105 is a synthetic nucleotide sequence encoding a mature TIC11243 protein, mTIC11243 for expression in bacteria.

SEQ ID NO: 106 is an amino acid sequence of a mature TIC11243 protein, mTIC11243.

SEQ ID NO:107 is a synthetic nucleotide sequence encoding a mature TIC11256 protein, mTIC11256 for expression in bacteria.

SEQ ID NO: 108 is an amino acid sequence of a mature TIC11256 protein, mTIC11256.

SEQ ID NO:109 is a synthetic nucleotide sequence encoding a mature TIC4544 protein, mTIC4544 for expression in bacteria.

SEQ ID NO:110 is an amino acid sequence of a mature TIC4544 protein, mTIC4544.

SEQ ID NO:111 is a synthetic nucleotide sequence encoding a mature TIC4545 protein, mTIC4545 for expression in bacteria.

SEQ ID NO: 112 is an amino acid sequence of a mature TIC4545 protein, mTIC4545.

SEQ ID NO:113 is a synthetic nucleotide sequence encoding a mature TIC6871 protein, mTIC6871 for expression in bacteria.

SEQ ID NO: 114 is an amino acid sequence of a mature TIC6871 protein, mTIC6871.

SEQ ID NO:115 is a synthetic nucleotide sequence encoding a mature TIC7429 protein, mTIC7429 for expression in bacteria.

SEQ ID NO: 116 is an amino acid sequence of a mature TIC7429 protein, mTIC7429.

SEQ ID NO:117 is a synthetic nucleotide sequence encoding a mature TIC7497 protein, mTIC7497 for expression in bacteria.

SEQ ID NO: 118 is an amino acid sequence of a mature TIC7497 protein, mTIC7497.

SEQ ID NO:119 is a synthetic nucleotide sequence encoding a mature TIC7511 protein, mTIC7511 for expression in bacteria.

SEQ ID NO: 120 is an amino acid sequence of a mature TIC7511 protein, mTIC7511.

SEQ ID NO:121 is a synthetic nucleotide sequence encoding a mature TIC7513 protein, mTIC7513 for expression in bacteria.

SEQ ID NO: 122 is an amino acid sequence of a mature TIC7513 protein, mTIC7513.

SEQ ID NO:123 is a synthetic nucleotide sequence encoding a mature TIC7518 protein, mTIC7518 for expression in bacteria.

SEQ ID NO:124 is an amino acid sequence of a mature TIC7518 protein, mTIC7518.

SEQ ID NO:125 is a synthetic nucleotide sequence encoding a mature TIC7524 protein, mTIC7524 for expression in bacteria.

SEQ ID NO: 126 is an amino acid sequence of a mature TIC7524 protein, mTIC7524.

SEQ ID NO:127 is a synthetic nucleotide sequence encoding a mature TIC7526 protein, mTIC7526 for expression in bacteria.

SEQ ID NO: 128 is an amino acid sequence of a mature TIC7526 protein, mTIC7526.

SEQ ID NO:129 is a synthetic nucleotide sequence encoding a mature TIC7528 protein, mTIC7528 for expression in bacteria.

SEQ ID NO: 130 is an amino acid sequence of a mature TIC7528 protein, mTIC7528.

SEQ ID NO:131 is a synthetic nucleotide sequence encoding a mature TIC7535 protein, mTIC7535 for expression in bacteria.

SEQ ID NO:132 is an amino acid sequence of a mature TIC7535 protein, mTIC7535.

DETAILED DESCRIPTION OF THE INVENTION

The problem in the art of agricultural pest control can be characterized as a need for new toxin proteins that are efficacious against target pests, exhibit broad spectrum toxicity against target pest species, are capable of being expressed in plants without causing undesirable agronomic issues, and provide an alternative mode of action compared to current toxins that are used commercially in plants. Novel insecticidal proteins exemplified by TIC3668 are disclosed herein, and address each of these needs, particularly against a broad spectrum of Coleopteran and Lepidopteran insect pests, and more particularly against corn rootworm pest species.

Reference in this application to "TIC3668", "TIC3668 protein", "TIC3668 protein toxins", "TIC3668 toxin proteins", "TIC3668-related toxins", "TIC3668-related toxin class or family", "TIC3668-related toxin proteins", "TIC3668-type proteins", "TIC3668-like proteins, "TIC3668-related toxin polypeptides", "TIC3668-related pesticidal proteins", or "TIC3668-type insect inhibitory polypeptide" and the like, refer to any novel insect inhibitory protein that comprises, that consists of, that is substantially homologous to, that is similar to, or that is derived from any insect inhibitory polypeptide sequence of TIC3668 (SEQ ID NO:2) and insect inhibitory segments thereof, or combinations thereof, that confer activity against Coleopteran pests and Lepidopteran pests, including any protein exhibiting insect inhibitory activity if alignment of such protein with TIC3668 (SEQ ID NO:2), TIC3669 (SEQ ID NO:4). TIC3670 (SEQ ID NO:6), TIC4076 (SEQ ID NO:8). TIC4078 (SEQ ID NO: 10), TIC4346 (SEQ ID NO: 14), TIC4826 (SEQ ID NO:16), TIC4861 (SEQ ID NO:18). TIC4862 (SEQ ID NO:20), TIC4863 (SEQ ID NO:22). TIC11239 (SEQ ID NO:74), TIC11243 (SEQ ID NO:76), TIC11256 (SEQ ID NO:78), TIC4544 (SEQ ID NO:80), TIC4545 (SEQ ID NO:82), TIC6871 (SEQ ID NO:84), TIC7429 (SEQ ID NO:86), TIC7497 (SEQ ID NO:88), TIC7511 (SEQ ID NO:90), TIC7513 (SEQ ID NO:92), TIC7518 (SEQ ID NO:94), TIC7524 (SEQ ID NO:96), TIC7526 (SEQ ID NO:98), TIC7528 (SEQ ID NO:100), and TIC7535 (SEQ ID NO:102) results in amino acid sequence identity of any fraction percentage from about 35% to about 100% percent. The TIC3668-type protein toxins disclosed in this application include TIC3668, TIC3669. TIC3670, TIC4076, TIC4078. TIC4346, TIC4826, TIC4861. TIC4862, TIC4863, TIC11239, TIC11243, TIC11256, TIC4544, TIC4545, TIC6871, TIC7429, TIC7497, TIC7511, TIC7513, TIC7518, TIC7524, TIC7526, TIC7528, TIC7535, and the collage TIC4260 protein (SEQ ID NO:12). The TIC3668-type protein class is intended to include the precursor forms as well as the mature length forms of the proteins.

The term "segment" or "fragment" is used in this application to describe consecutive amino acid or nucleic acid sequences that are shorter than the complete amino acid or nucleic acid sequence describing a TIC3668-type protein. A segment or fragment exhibiting insect inhibitory activity is also disclosed in this application if alignment of such segment or fragment, with the corresponding section of the TIC3668-type protein set forth in SEQ ID NO:2, results in amino acid sequence identity of any fraction percentage from about 35 to about 100 percent between the segment or fragment and the corresponding section of the TIC3668-type protein.

Reference in this application to the terms "active" or "activity", "pesticidal activity" or "insecticidal activity", "insect inhibitory" or "insecticidal" refer to efficacy of a toxic agent, such as a protein toxin, in inhibiting (inhibiting growth, feeding, fecundity, or viability), suppressing (suppressing growth, feeding, fecundity, or viability), controlling (controlling the pest infestation, controlling the pest feeding activities on a particular crop containing an effective amount of the TIC3668-type protein) or killing (causing the morbidity, mortality, or reduced fecundity of) a pest. These terms are intended to include the result of providing a pesticidally effective amount of a toxic protein to a pest where the exposure of the pest to the toxic protein results in morbidity, mortality, reduced fecundity, or stunting. These terms also include repulsion of the pest from the plant, a tissue of the plant, a plant part, seed, plant cells, or from the particular geographic location where the plant may be growing, as a result of providing a pesticidally effective amount of the toxic protein in or on the plant. In general, pesticidal activity refers to the ability of a toxic protein to be effective in inhibiting the growth, development, viability, feeding behavior, mating behavior, fecundity, or any measurable decrease in the adverse effects caused by an insect feeding on this protein, protein fragment, protein segment or polynucleotide of a particular target pest, including but not limited to insects of the order Lepidoptera or Coleoptera. The toxic protein can be produced by the plant or can be applied to the plant or to the environment within the location where the plant is located. The terms "bioactivity", "effective", "efficacious" or variations thereof are also terms interchangeably utilized in this application to describe the effects of proteins of the present invention on target insect pests.

A pesticidally effective amount of a toxic agent, when provided in the diet of a target pest, exhibits pesticidal activity when the toxic agent contacts the pest. A toxic agent can be a pesticidal protein or one or more chemical agents known in the art. Insecticidal chemical agents and insecticidal protein agents can be used alone or in combinations with each other. Chemical agents include but are not limited to dsRNA molecules targeting specific genes for suppression in a target pest, organochlorides, organophosphates, carbamates, pyrethroids, neonicotinoids, and ryanoids. Insecticidal protein agents include the protein toxins set forth in this application, as well as other proteinaceous toxic agents including those that target Lepidopteran and Coleopteran, as well as protein toxins that are used to control other plant pests such as Cry proteins available in the art for use in controlling Hemipteran and Homopteran species.

It is intended that reference to a pest, particularly a pest of a crop plant, means insect pests of crop plants, particularly those that are controlled by the TIC3668-related protein toxin class. However, reference to a pest can also include Hemipteran and Homopteran insect pests of plants, as well as nematodes and fungi when toxic agents targeting these pests are co-localized or present together with one or more proteins of the TIC3668-related protein toxin class.

The individual proteins which comprise the TIC3668-related protein class are related by common function and exhibit insecticidal activity towards insect pests from the Coleoptera and Lepidoptera insect species, including adults, pupae, larvae, and neonates. The insects of the order Lepidoptera include, but are not limited to, armyworms, cutworms, loopers, and heliothines in the Family Noctuidae, e.g., fall armyworm (*Spodoptera frugiperda*), beet armyworm (*Spodoptera exigua*), bertha armyworm (*Mamestra configurata*), black cutworm (*Agrotis ipsilon*), cabbage looper (*Trichoplusia ni*), soybean looper (*Pseudoplusia includens*), velvetbean caterpillar (*Anticarsia gemmatalis*), green cloverworm (*Hypena scabra*), tobacco budworm (*Heliothis virescens*), granulate cutworm (*Agrotis subterranea*), armyworm (*Pseudaletia unipuncta*), western cutworm (*Agrotis orthogonia*); borers, casebearers, webworms, coneworms, cabbageworms and skeletonizers from the Family Pyralidae, e.g., European corn borer (*Ostrinia nubilalis*), navel orangeworm (*Amyelois transitella*), corn root webworm (*Crambus caliginosellus*), sod webworm (*Herpetogramma licarsisalis*), sunflower moth (*Homoeosoma electellum*), lesser cornstalk borer (*Elasmopalpus lignosellus*); leafrollers, budworms, seed worms, and fruit worms in the Family Tortricidae, e.g., codling moth (*Cydia pomonella*), grape berry moth (*Endopiza viteana*), oriental fruit moth (*Grapholita molesta*), sunflower bud moth (*Suleima helianthana*); and many other economically important Lepidoptera, e.g., diamondback moth (*Plutella xylostella*), pink bollworm (*Pectinophora gossypiella*) and gypsy moth (*Lymantria dispar*). Other insect pests of order Lepidoptera include, e.g., *Alabama argillacea* (cotton leaf worm), *Archips argyrospila* (fruit tree leaf roller), *Archips rosana* (European leafroller) and other *Archips* species, *Chilo suppressalis* (Asiatic rice borer, or rice stem borer), Cnaphalocrocis *medinalis* (rice leaf roller), *Crambus caliginosellus* (corn root webworm), *Crambus teterrellus* (bluegrass webworm), *Diatraea grandiosella* (southwestern corn borer), *Diatraea saccharalis* (surgarcane borer), *Earias insulana* (spiny bollworm), *Earias vittella* (spotted bollworm), *Helicoverpa armigera* (American bollworm), *Helicoverpa zea* (corn carworm or cotton bollworm), *Heliothis virescens* (tobacco budworm), *Herpetogramma licarsisalis* (sod webworm), *Lobesia botrana* (European grape vine moth), *Phyllocnistis citrella* (citrus leafminer), *Pieris brassicae* (large white butterfly), *Pieris rapae* (imported cabbageworm, or small white butterfly), *Plutella xylostella* (diamondback moth), *Spodoptera exigua* (beet armyworm), *Spodoptera litura* (tobacco cutworm, cluster caterpillar), and *Tuta absoluta* (tomato leafminer). The insects of the order Coleoptera include, but are not limited to, *Agriotes* spp., *Anthonomus* spp., *Atomaria linearis, Chaetocnema tibialis, Cosmopolites* spp., *Curculio* spp., *Dermestes* spp., *Diabrotica* spp., *Epil-*

*achna* spp., *Eremnus* spp., *Leptinotarsa decemlineata, Lissorhoptrus* spp., *Melolontha* spp., *Orycaephilus* spp., *Otiorhynchus* spp., *Phlyctinus* spp., *Popillia* spp., *Psylliodes* spp., *Rhizopertha* spp., Scarabeidae, *Sitophilus* spp., *Sitotroga* spp., *Tenebrio* spp., *Tribolium* spp. and *Trogoderma* spp, particularly when the pest is *Diabrotica virgifera virgifera* (Western Corn Rootworm, WCR), *Diabrotica barberi* (Northern Corn Rootworm, NCR), *Diabrotica virgifera zeae* (Mexican Corn Rootworm, MCR), *Diabrotica* balteata (Brazilian Corn Rootworm (BZR), *Diabrotica* undecimpunctata howardii (Southern Corn Rootworm, SCR) and a Brazilian Corn Rootworm complex (BCR) consisting of *Diabrotica viridula* and *Diabrotica speciosa*).

Reference in this application to an "isolated DNA molecule", "isolated polynucleotide molecule", or an equivalent term or phrase, is intended to mean that the DNA molecule is one that is present alone or in combination with other compositions, but not within its natural environment. For example, nucleic acid elements such as a coding sequence, intron sequence, untranslated leader sequence, promoter sequence, transcriptional termination sequence, and the like, that are naturally found within the DNA of the genome of an organism are not considered to be "isolated" so long as the element is within the genome of the organism and at the location within the genome in which it is naturally found. However, each of these elements, and subparts of these elements, would be "isolated" within the scope of this disclosure so long as the element is not within the genome of the organism and at the location within the genome in which it is naturally found. Similarly, a nucleotide sequence encoding a insecticidal protein or any naturally occurring insecticidal variant of that protein would be an isolated nucleotide sequence so long as the nucleotide sequence was not within the DNA of the bacterium from which the sequence encoding the protein is naturally found. A synthetic nucleotide sequence encoding the amino acid sequence of the naturally occurring insecticidal protein would be considered to be isolated for the purposes of this disclosure. For the purposes of this disclosure, any transgenic nucleotide sequence, i.e., the nucleotide sequence of the DNA inserted into the genome of the cells of a plant or bacterium, or present in an extrachromosomal vector would be considered to be an isolated nucleotide sequence whether it is present within the plasmid or similar structure used to transform the cells, within the genome of the plant or bacterium, or present in detectable amounts in tissues, progeny, biological samples or commodity products derived from the plant or bacterium.

As described further in this application, an open reading frame (ORF) (SEQ ID NO:1) encoding TIC3668 (SEQ ID NO:2) was discovered in DNA obtained from *Brevibacillus laterosporus* strain EG5552. Other bacterial genomes were then screened for sequences encoding TIC3668-related protein. Several other open reading frames were identified in these other bacterial genomes encoding amino acid sequences resembling the EG5552 TIC3668 protein, including the TIC3668-like proteins TIC3669 which was discovered in DNA obtained from *Brevibacillus laterosporus* strain EG5551 (SEQ ID NO:3 encoding SEQ ID NO:4), TIC3670 which was discovered in DNA obtained from *Brevibacillus laterosporus* strain EG5553 (SEQ ID NO:5 encoding SEQ ID NO:6). TIC4076 which was discovered in DNA obtained from *Brevibacillus laterosporus* strain ATCC6456 (SEQ ID NO:7 encoding SEQ ID NO:8). TIC4078 which was discovered in DNA obtained from *Brevibacillus laterosporus* strain EG4227 (SEQ ID NO:9 encoding SEQ ID NO:10), TIC4346 which was discovered in DNA obtained from

*Brevibacillus laterosporus* strain EG5551 (SEQ ID NO:13 encoding SEQ ID NO:14), TIC4826 which was discovered in DNA obtained from *Brevibacillus laterosporus* strain AG0021D10 (SEQ ID NO:15 encoding SEQ ID NO:16), TIC4861 (SEQ ID NO:17 encoding SEQ ID NO:18), TIC4862 (SEQ ID NO: 19 encoding SEQ ID NO:20) and TIC4863 (SEQ ID NO:21 encoding SEQ ID NO:22) which were discovered in DNA obtained from *Brevibacillus laterosporus* strain EG4227, TIC11239 which was discovered in DNA obtained from *Brevibacillus laterosporus* strain DSC004653 (SEQ ID NO:73 encoding SEQ ID NO:74), TIC11243 which was discovered in DNA obtained from *Brevibacillus laterosporus* strain DSC006878 (SEQ ID NO:75 encoding SEQ ID NO:76), TIC11256 which was discovered in DNA obtained from *Brevibacillus laterosporus* strain DSC010447 (SEQ ID NO:77 encoding SEQ ID NO:78), TIC4544 (SEQ ID NO:79 encoding SEQ ID NO:80) and TIC4545 (SEQ ID NO:81 encoding SEQ ID NO:82) which were discovered in DNA obtained from *Brevibacillus laterosporus* strain EG5551, TIC6871 which was discovered in DNA obtained from *Brevibacillus laterosporus* strain DSC004348 (SEQ ID NO:83 encoding SEQ ID NO:84), TIC7429 which was discovered in DNA obtained from *Brevibacillus laterosporus* strain DSC007446 (SEQ ID NO:85 encoding SEQ ID NO:86), TIC7497 which was discovered in DNA obtained from *Brevibacillus laterosporus* strain DSC007646 (SEQ ID NO:87 encoding SEQ ID NO:88), TIC7511 which was discovered in DNA obtained from *Brevibacillus laterosporus* strain AG0107C08 (SEQ ID NO:89 encoding SEQ ID NO:90), TIC7513 which was discovered in DNA obtained from *Brevibacillus laterosporus* strain DSC004494 (SEQ ID NO:91 encoding SEQ ID NO:92), TIC7518 which was discovered in DNA obtained from *Brevibacillus laterosporus* strain DSC004344 (SEQ ID NO:93 encoding SEQ ID NO:94), TIC7524 which was discovered in DNA obtained from *Brevibacillus laterosporus* strain DSC004820 (SEQ ID NO:95 encoding SEQ ID NO:96), TIC7526 which was discovered in DNA obtained from *Brevibacillus laterosporus* strain DSC005166 (SEQ ID NO:97 encoding SEQ ID NO:98), TIC7528 which was discovered in DNA obtained from *Brevibacillus laterosporus* strain DSC005474 (SEQ ID NO:99 encoding SEQ ID NO:100), and TIC7535 which was discovered in DNA obtained from *Brevibacillus laterosporus* strain DSC007651 (SEQ ID NO:101 encoding SEQ ID NO:102). One additional TIC3668-like protein, TIC4260 (SEQ ID NO: 11 encoding SEQ ID NO:12), was created by combining the naturally occurring amino acid sequence variation from five different native TIC3668-like proteins to create a collage protein.

The respective coding sequences were cloned and expressed in microbial host cells to produce recombinant proteins for use in insect bioassays. As described further in this application, it is shown that these proteins exhibit bioactivity against *Diabrotica* species, including Western Corn Rootworm (WCR, *Diabrotica virgifera virgifera*) and Northern Corn Rootworm (NCR, *Diabrotica barberi*); as well as Lepidopteran species, including Western European Corn Borer (ECB, *Ostrinia nubialis*), Southwestern Corn Borer (SWC, *Diatraea grandiosella*), and Soybean Looper (SBL, *Chrysodeixis includens*).

A surprising feature of the TIC3668-type proteins is the presence of a N-terminal amino acid segment corresponding to amino acid position 1 to 23 for TIC3668, TIC3669, TIC3670, TIC4076, TIC4078, TIC4260, TIC4346, TIC4826, TIC4863, TIC11239, TIC11243, TIC11256, TIC4544, TIC4545, TIC6871, TIC7429, TIC7497, TIC7511, TIC7513, TIC7518, TIC7524, TIC7526, TIC7528, and TIC7535; 1 to 12 for TIC4861; and 1 to 21 for TIC4862. Each of these N-terminal amino acid segments may be omitted from the respective protein and the polynucleotide sequence encoding the respective segment may also be omitted. When expressed in planta, omission of these respective segments surprisingly resulted in an increase of insecticidal activity against corn rootworm species compared to expression of the full-length protein toxin containing the omitted segment. Protein toxin segments lacking the N-terminal amino acid segments referred to above are referred to herein as "mature TIC3668-type toxin proteins". In general, reference to the mature version of a TIC3668-type protein is annotated herein with the letter "m" preceding the name of the toxin to differentiate reference to the mature sequence from the full length native sequence. For example, the mature version of the amino acid sequence for TIC3668 (SEQ ID NO: 2) is mTIC3668 (SEQ ID NO:23). The mature versions for TIC3668 (SEQ ID NO:2), TIC3669 (SEQ ID NO:4), TIC3670 (SEQ ID NO:6), TIC4076 (SEQ ID NO:8), TIC4078 (SEQ ID NO: 10). TIC4346 (SEQ ID NO: 14), TIC4826 (SEQ ID NO: 16), TIC4861 (SEQ ID NO:18), TIC4862 (SEQ ID NO:20). TIC4863 (SEQ ID NO:22), TIC11239 (SEQ ID NO:74), TIC11243 (SEQ ID NO:76), TIC11256 (SEQ ID NO:78), TIC4544 (SEQ ID NO:80), TIC4545 (SEQ ID NO:82), TIC6871 (SEQ ID NO:84), TIC7429 (SEQ ID NO:86), TIC7497 (SEQ ID NO:88), TIC7511 (SEQ ID NO:90), TIC7513 (SEQ ID NO:92), TIC7518 (SEQ ID NO:94), TIC7524 (SEQ ID NO:96), TIC7526 (SEQ ID NO:98), TIC7528 (SEQ ID NO: 100), and TIC7535 (SEQ ID NO:102) are mTIC3669 (SEQ ID NO:24), mTIC3670 (SEQ ID NO:25), mTIC4076 (SEQ ID NO:26), mTIC4078 (SEQ ID NO:27), mTIC4260 (SEQ ID NO:28), mTIC4346 (SEQ ID NO:29), mTIC4826 (SEQ ID NO:30), mTIC11239 (SEQ ID NO:104), mTIC11243 (SEQ ID NO:106), mTIC11256 (SEQ ID NO:108), mTIC4544 (SEQ ID NO:110), mTIC4545 (SEQ ID NO:112), mTIC6871 (SEQ ID NO:114), mTIC7429 (SEQ ID NO:116), mTIC7497 (SEQ ID NO:118), mTIC7511 (SEQ ID NO:120), mTIC7513 (SEQ ID NO:122), mTIC7518 (SEQ ID NO:124), mTIC7524 (SEQ ID NO:126), mTIC7526 (SEQ ID NO:128), mTIC7528 (SEQ ID NO:130), and mTIC7535 (SEQ ID NO:132), respectively. The full-length proteins TIC4861 (SEQ ID NO:18), TIC4862 (SEQ ID NO:20) and TIC4863 (SEQ ID NO:22) are sequence length variants of each other and differ only in the length of their N-terminal amino acid segment. Removal of the N-terminal amino acid segment in TIC4861, TIC4862, and TIC4863 creates an identical mature amino acid sequence for mTIC4861, mTIC4862, and mTIC4863. Thus, the amino acid sequences for mTIC4861, mTIC4862, and mTIC4863 are encoded by the same polynucleotide sequence (mTIC4861, SEQ ID NO:31). The mature TIC3668-like protein sequences are encoded by SEQ ID NO:64 (encoding mTIC3668), SEQ ID NO:65 (encoding mTIC3669), SEQ ID NO:66 (encoding mTIC3670), SEQ ID NO:67 (encoding mTIC4076), SEQ ID NO:68 (encoding mTIC4078), SEQ ID NO:69 (encoding mTIC4260), SEQ ID NO:70 (encoding mTIC4346), SEQ ID NO:71 (encoding mTIC4826), SEQ ID NO. 72 (encoding mTIC4861, mTIC4862, and mTIC4863), SEQ ID NO: 103 (encoding mTIC11239), SEQ ID NO: 105 (encoding mTIC11243), SEQ ID NO:107 (encoding mTIC11256), SEQ ID NO:109 (encoding mTIC4544), SEQ ID NO:111 (encoding mTIC4545), SEQ ID NO:113 (encoding mTIC6871), SEQ ID NO:115 (encoding mTIC7429), SEQ ID NO:117 (encoding mTIC7497), SEQ ID NO:119 (encoding mTIC7511), SEQ ID NO:121 (encoding mTIC7513), SEQ ID NO:123 (encoding mTIC7518), SEQ ID NO:125 (encoding mTIC7524), SEQ ID NO: 127 (encoding mTIC7526), SEQ ID NO: 129 (encoding mTIC7528), and SEQ ID NO:131 (encoding mTIC7535) for expression in bacterial hosts.

Additional members to the TIC3668-type family can be created by using the naturally occurring amino acid variations from some or all family members to create novel proteins of a higher level of amino acid sequence diversity and with novel properties. Variants of the TIC3668-type protein toxin class were produced by aligning the amino acid sequences of TIC3668-type family members and combining differences at the amino acid sequence level into a novel amino acid sequence and making appropriate changes to the polynucleotides encoding these variants. One such example is TIC4260. SEQ ID NO:11 is the polynucleotide sequence encoding the TIC4260 protein (SEQ ID NO: 12). The mature protein (mTIC4260, SEQ ID NO:28) is encoded by the polynucleotide sequence of SEQ ID NO:43.

Fragments of the TIC3668-type protein toxins can be truncated forms wherein one or more amino acids are deleted from the N-terminal end, C-terminal end, the middle of the protein, or combinations thereof with insect inhibitory activity. These fragments can be naturally occurring or synthetic variants of TIC3668, TIC3669, TIC3670, TIC4260, TIC4076, TIC4078, TIC4346, TIC4826, TIC4861, TIC4862 TIC4863, TIC11239, TIC11243, TIC11256, TIC4544, TIC4545, TIC6871, TIC7429, TIC7497, TIC7511, TIC7513, TIC7518, TIC7524, TIC7526, TIC7528, or TIC7535 but should retain or improve the insect inhibitory activity of TIC3668, TIC3669, TIC3670, TIC4260, TIC4076, TIC4078, TIC4346, TIC4826, TIC4861, TIC4862 TIC4863, TIC11239, TIC11243, TIC11256, TIC4544, TIC4545, TIC6871, TIC7429, TIC7497, TIC7511, TIC7513, TIC7518, TIC7524, TIC7526, TIC7528, or TIC7535. Truncated N-terminal or C-terminal deletion variants include, but are not limited to, TIC3668, TIC3669, TIC3670, TIC4260, TIC4076, TIC4078, TIC4346, TIC4826, TIC4861, TIC4862 TIC4863, TIC11239, TIC11243, TIC11256, TIC4544, TIC4545, TIC6871, TIC7429, TIC7497, TIC7511, TIC7513, TIC7518, TIC7524, TIC7526, TIC7528, or TIC7535 proteins that lack amino acid residues from either the N-terminus and/or the C-terminus. For example, N-terminal amino acid residues 1 to 23 of a TIC3668 protein can be deleted resulting in a toxin protein having amino acids 24-317 of SEQ ID NO:2. Removing 10 or 20 amino acids from the C-terminal amino acid end of a TIC3668 protein resulted in a loss of insecticidal activity, while removing a single amino acid did not affect activity.

Proteins of the TIC3668-type protein class, and proteins that resemble the proteins of the TIC3668-type protein class, can be identified by comparison to each other using various computer based algorithms known in the art (see Tables 1 and 2). Amino acid sequence identities reported herein are a result of a Clustal W alignment using these default parameters: Weight matrix: blosum, Gap opening penalty: 10.0, Gap extension penalty: 0.05, Hydrophilic gaps: On, Hydrophilic residues: GPSNDQERK, Residue-specific gap penalties: On (Thompson, et al. (1994) Nucleic Acids Research, 22:4673-4680). Percent amino acid identity is further calculated by the product of 100% multiplied by (amino acid identities/length of subject protein). Other alignment algorithms are also available in the art and provide results similar to those obtained using a Clustal W alignment.

It is intended that a protein exhibiting insect inhibitory activity against a Lepidopteran insect species is a member of the TIC3668-type protein toxin class if the protein is used in a query, e.g., in a Clustal W alignment, and at least one of the proteins of the present invention as set forth as mTIC4260 is identified as hits in such alignment in which the query protein exhibits at least about 85% to about 100% amino acid sequence identity along the length of the query protein, that is 85%, 86%, 87%, 88%, 89%, 90%, 91%, 92%, 93%, 94%, 95%, 96%, 97%, 98%, 99%, 100%, or any fraction percentage in this range; or at least one of the proteins of the present invention as set forth as mTIC3668 is identified as hits in such alignment in which the query protein exhibits at least about 89% to about 100% amino acid sequence identity along the length of the query protein, that is 89%, 90%, 91%, 92%, 93%, 94%, 95%, 96%, 97%, 98%, 99%, 100%, or any fraction percentage in this range; or at least one of the proteins of the present invention as set forth as mTIC3669 and/or mTIC3670 are identified as hits in such alignment in which the query protein exhibits at least about 90% to about 100% amino acid sequence identity along the length of the query protein, that is 90%, 91%, 92%, 93%, 94%, 95%, 96%, 97%, 98%, 99%, 100%, or any fraction percentage in this range; or at least one of the proteins of the present invention as set forth as mTIC4826 is identified as a hit in such alignment in which the query protein exhibits at least about 91% to about 100% amino acid sequence identity along the length of the query protein, that is 91%, 92%, 93%, 94%, 95%, 96%, 97%, 98%, 99%, 100%, or any fraction percentage in this range.

It is intended that a protein exhibiting insect inhibitory activity against a Coleopteran insect species is a member of the TIC3668-type protein toxin class if the protein is used in a query, e.g., in a Clustal W alignment, and at least one of the proteins of the present invention as set forth as mTIC3668, mTIC3669, mTIC3670, mTIC4076, mTIC4078, mTIC4260, mTIC4346, mTIC4826, mTIC4861, mTIC4862, mTIC4863, mTIC11239, mTIC11243, mTIC11256, mTIC4544, mTIC4545, mTIC6871, mTIC7429, mTIC7497, mTIC7511, mTIC7513, mTIC7518, mTIC7524, mTIC7526, mTIC7528, and mTIC7535 are identified as hits in such alignment in which the query protein exhibits at least about 35% to about 100% amino acid identity along the length of the query protein that is about 35%, 40%, 50%, 60%, 70%, 75%, 76%, 77%, 78%, 79%, 80%, 81%, 82%, 83%, 84%, 85%, 85%, 87%, 88%, 89%, 90%, 91%, 92%, 93%, 94%, 95%, 96%, 97%, 98%, 99%, 100%, or any fraction percentage in this range.

Exemplary proteins of the TIC3668-type protein toxin class were aligned with each other using a Clustal W algorithm. A pair-wise matrix of percent amino acid sequence identities for each pair of the full-length proteins, TIC3668, TIC3670, TIC3669, TIC4076, TIC4346, TIC4861, TIC4862, TIC4863, TIC4826, TIC4078, and TIC4260 was created, as reported in Table 1. A pair-wise matrix of percent amino acid sequence identities for each pair of the mature-length proteins, mTIC4076, mTIC4346, mTIC4826, mTIC4861, mTIC4862, mTIC4863, mTIC3668, mTIC3670, mTIC3669, mTIC4078, and mTIC4260 was created, as reported in Table 2. A pair-wise matrix of percent amino acid sequence identities for the mature-length proteins, mTIC11239, mTIC11243, mTIC11256, mTIC4544, mTIC4545, mTIC6871, mTIC7429, mTIC7497, mTIC7511, mTIC7513, mTIC7518, mTIC7524, mTIC7526, mTIC7528, mTIC7535 in comparison with mTIC3670 was created, as reported in Table 3.

TABLE 1

Pair-wise matrix display of exemplary full-length proteins

| SEQ ID NO: | M | N | | | | | | | | | | |
|---|---|---|---|---|---|---|---|---|---|---|---|---|
| | | 2 | 6 | 4 | 8 | 14 | 18 | 20 | 22 | 16 | 10 | 12 |
| 2 | TIC3668 | — | 99.4 (315) | 97.8 (310) | 96.2 (305) | 97.2 (308) | 93.1 (295) | 95.6 (303) | 96.5 (306) | 97.2 (308) | 94.3 (299) | 96.2 (305) |
| 6 | TIC3670 | 99.4 (315) | — | 98.4 (312) | 96.8 (307) | 97.2 (308) | 93.7 (297) | 96.2 (305) | 97.2 (308) | 97.8 (310) | 95 (301) | 95.6 (303) |
| 4 | TIC3669 | 97.8 (310) | 98.4 (312) | — | 96.8 (307) | 96.8 (307) | 93.4 (296) | 96.2 (305) | 97.2 (308) | 97.5 (309) | 94.6 (300) | 95.3 (302) |
| 8 | TIC4076 | 96.2 (305) | 96.8 (307) | 96.8 (307) | — | 98.4 (312) | 94.3 (299) | 97.2 (308) | 98.1 (311) | 98.1 (311) | 96.2 (305) | 93.4 (296) |
| 14 | TIC4346 | 97.2 (308) | 97.2 (308) | 96.8 (307) | 98.4 (312) | — | 94.3 (299) | 97.2 (308) | 98.1 (311) | 98.7 (313) | 96.2 (305) | 93.7 (297) |
| 18 | TIC4861 | 96.4 (295) | 97.1 (297) | 96.7 (296) | 97.7 (299) | 97.7 (299) | — | 99.7 (305) | 99.7 (305) | 98.4 (301) | 95.4 (292) | 92.5 (283) |
| 20 | TIC4862 | 96.2 (303) | 96.8 (305) | 96.8 (305) | 97.8 (308) | 97.8 (308) | 96.8 (305) | — | 99.7 (314) | 98.4 (310) | 95.2 (300) | 92.4 (291) |
| 22 | TIC4863 | 96.5 (306) | 97.2 (308) | 97.2 (308) | 98.1 (311) | 98.1 (311) | 96.2 (305) | 99.1 (314) | — | 98.7 (313) | 95.6 (303) | 92.7 (294) |
| 16 | TIC4826 | 97.2 (308) | 97.8 (310) | 97.5 (309) | 98.1 (311) | 98.7 (313) | 95 (301) | 97.8 (310) | 98.7 (313) | — | 95.9 (304) | 93.4 (296) |
| 10 | TIC4078 | 94.3 (299) | 95 (301) | 94.6 (300) | 96.2 (305) | 96.2 (305) | 92.1 (292) | 94.6 (300) | 95.6 (303) | 95.9 (304) | — | 96.2 (305) |
| 12 | TIC4260 | 96.2 (305) | 95.6 (303) | 95.3 (302) | 93.4 (296) | 93.7 (297) | 89.3 (283) | 91.8 (291) | 92.7 (294) | 93.4 (296) | 96.2 (305) | — |

Table Description: Clustal W alignment between (X) versus (Y) are reported in a pair-wise matrix. Columns under (N) refer to SEQ ID NO. Column (M) refers to protein name (TIC#). The percent amino acid identity between all pairs is calculated and is represented by the first number in each box. The second number (in parentheses) in each box represents the number of identical amino acids between the pair.

TABLE 2

Pair-wise matrix display of exemplary mature proteins

| SEQ ID NO: | M | N | | | | | | | | |
|---|---|---|---|---|---|---|---|---|---|---|
| | | 26 | 29 | 30 | 31 | 23 | 25 | 24 | 27 | 28 |
| 26 | mTIC4076 | — | 98.3 (290) | 98 (289) | 98 (289) | 96.3 (284) | 96.9 (286) | 96.6 (285) | 96.3 (284) | 93.2 (275) |
| 29 | mTIC4346 | 98.3 (290) | — | 98.6 (291) | 98 (289) | 97.3 (287) | 97.3 (287) | 96.6 (285) | 96.3 (284) | 93.6 (276) |
| 30 | mTIC4826 | 98 (289) | 98.6 (291) | — | 98.6 (291) | 97.3 (287) | 98 (289) | 97.3 (287) | 95.9 (283) | 93.2 (275) |
| 31 | mTIC4861 mTIC4862 mTIC4863 | 98 (289) | 98 (289) | 98.6 (291) | — | 96.6 (285) | 97.3 (287) | 96.9 (286) | 95.6 (282) | 92.5 (273) |
| 23 | mTIC3668 | 96.3 (284) | 97.3 (287) | 97.3 (287) | 96.6 (285) | — | 99.3 (293) | 98 (289) | 93.9 (277) | 95.9 (283) |
| 25 | mTIC3670 | 96.9 (286) | 97.3 (287) | 98 (289) | 97.3 (287) | 99.3 (293) | — | 98.6 (291) | 94.6 (279) | 95.3 (281) |
| 24 | mTIC3669 | 96.6 (285) | 96.6 (285) | 97.3 (287) | 96.9 (286) | 98 (289) | 98.6 (291) | — | 94.6 (279) | 95.3 (281) |
| 27 | mTIC4078 | 96.3 (284) | 96.3 (284) | 95.9 (283) | 95.6 (282) | 93.9 (277) | 94.6 (279) | 94.6 (279) | — | 95.9 (283) |
| 28 | mTIC4260 | 93.2 (275) | 93.6 (276) | 93.2 (275) | 92.5 (273) | 95.9 (283) | 95.3 (281) | 95.3 (281) | 95.9 (283) | — |

Table Description: Clustal W alignment between (X) versus (Y) are reported in a pair-wise matrix. Columns under (N) refer to SEQ ID NO. Column (M) refers to protein name (TIC#). The percent amino acid identity between all pairs is calculated and is represented by the first number in each box. The second number (in parentheses) in each box represents the number of identical amino acids between the pair.

TABLE 3

Pair-wise matrix display of exemplary mature proteins in comparison to mTIC3670

| SEQ ID NO: | M | 128 | 132 | 114 | 106 | 118 | 25 | 126 | 130 | 108 | 136 | 112 | 116 | 110 | 134 | 122 | 124 |
|---|---|---|---|---|---|---|---|---|---|---|---|---|---|---|---|---|---|
| 128 | mTIC7518 | — | 99.7 (294) | 99.7 (294) | 98.3 (290) | 98 (289) | 97.3 (287) | 97.3 (287) | 97.6 (288) | 96.9 (286) | 96.6 (285) | 96.3 (284) | 96.9 (286) | 97.6 (288) | 97.6 (287) | 97.3 (287) | 95.6 (282) |
| 132 | mTIC7526 | 99.7 (294) | — | 99.3 (293) | 98 (289) | 97.6 (288) | 96.9 (286) | 96.9 (286) | 97.3 (287) | 96.6 (285) | 96.3 (284) | 95.9 (283) | 96.6 (285) | 97.3 (287) | 97.3 (287) | 96.9 (286) | 95.3 (281) |
| 114 | mTIC4545 | 99.7 (294) | 99.3 (293) | — | 98.6 (291) | 98.3 (290) | 97.6 (288) | 97.6 (288) | 98 (289) | 97.3 (287) | 96.9 (286) | 96.6 (285) | 97.3 (287) | 98 (289) | 98 (289) | 97.6 (288) | 95.9 (283) |
| 106 | mTIC11239 | 98.3 (290) | 98 (289) | 98.6 (291) | — | 99 (292) | 99 (292) | 99 (292) | 99.3 (293) | 98.6 (291) | 98.3 (290) | 98 (289) | 98.6 (291) | 98 (289) | 98.6 (291) | 98.3 (290) | 96.6 (285) |
| 118 | mTIC7429 | 98 (289) | 97.6 (288) | 98.3 (290) | 99 (292) | — | 99 (292) | 99 (292) | 99 (292) | 98.6 (291) | 98.3 (290) | 98 (289) | 98.6 (291) | 98 (289) | 98.6 (291) | 98.3 (290) | 96.6 (285) |
| 25 | mTIC3670 | 97.3 (287) | 96.9 (286) | 97.6 (288) | 99 (292) | 99 (292) | — | 100 (295) | 99.7 (294) | 99.7 (294) | 99.3 (293) | 98.3 (290) | 99 (292) | 98.6 (291) | 99 (292) | 98.6 (291) | 96.9 (286) |
| 126 | mTIC7513 | 97.3 (287) | 96.9 (286) | 97.6 (288) | 99 (292) | 99 (292) | 100 (295) | — | 99.7 (294) | 99.7 (294) | 99.3 (293) | 98.3 (290) | 99 (292) | 98.6 (291) | 99 (292) | 98.6 (291) | 96.9 (286) |
| 130 | mTIC7524 | 97.6 (288) | 97.3 (287) | 98 (289) | 99.3 (293) | 99 (292) | 99.7 (294) | 99.7 (294) | — | 99.3 (293) | 99 (292) | 98 (289) | 98.6 (291) | 98.3 (290) | 98.6 (291) | 98.3 (290) | 96.6 (285) |
| 108 | mTIC11243 | 96.9 (286) | 96.6 (285) | 97.3 (287) | 98.6 (291) | 98.6 (291) | 99.7 (294) | 99.7 (294) | 99.3 (293) | — | 99.7 (294) | 98.6 (291) | 99.3 (293) | 98.3 (290) | 98.6 (291) | 98.3 (290) | 96.6 (285) |
| 136 | mTIC7535 | 96.6 (285) | 96.3 (284) | 96.9 (286) | 98.3 (290) | 98.3 (290) | 99.3 (293) | 99.3 (293) | 99 (292) | 99.7 (294) | — | 99.7 (290) | 99 (292) | 98 (289) | 99 (292) | 98.6 (291) | 96.9 (286) |
| 112 | mTIC4544 | 96.3 (284) | 95.9 (283) | 96.6 (285) | 98 (289) | 98 (289) | 98.3 (290) | 98.3 (290) | 98 (289) | 98.6 (291) | 98.3 (290) | — | 99.3 (293) | 97.6 (288) | 98 (289) | 98.3 (290) | 96.9 (286) |
| 116 | mTIC6871 | 96.9 (286) | 96.6 (285) | 97.3 (287) | 98.6 (291) | 98.6 (291) | 99 (292) | 99 (292) | 98.6 (291) | 99.3 (293) | 99 (292) | 99.3 (293) | — | 98.3 (290) | 98.6 (291) | 98.3 (290) | 96.9 (286) |
| 110 | mTIC11256 | 97.6 (288) | 97.3 (287) | 98 (289) | 98 (289) | 98 (289) | 98.6 (291) | 98.6 (291) | 98.3 (290) | 98.3 (290) | 98 (289) | 97.6 (288) | 98.3 (290) | — | 98 (289) | 97.6 (288) | 96.6 (285) |
| 134 | mTIC7528 | 97.6 (288) | 97.3 (287) | 98 (289) | 98.6 (291) | 98.6 (291) | 99 (292) | 99 (292) | 98.6 (291) | 98.6 (291) | 99 (292) | 98 (289) | 98.6 (291) | 98 (289) | — | 99.7 (294) | 98 (289) |
| 122 | mTIC7497 | 97.3 (287) | 96.9 (286) | 97.6 (288) | 98.3 (290) | 98.3 (290) | 98.6 (291) | 98.6 (291) | 98.3 (290) | 98.3 (290) | 98.6 (291) | 98.3 (290) | 98.3 (290) | 97.6 (288) | 99.7 (294) | — | 98.3 (290) |
| 124 | mTIC7511 | 95.6 (282) | 95.3 (281) | 95.9 (283) | 96.6 (285) | 96.6 (285) | 96.9 (286) | 96.9 (286) | 96.6 (285) | 96.6 (285) | 96.9 (286) | 96.9 (286) | 96.9 (286) | 96.6 (285) | 98 (289) | 98.3 (290) | — |

Table Description: Clustal W alignment between (X) versus (Y) are reported in a pair-wise matrix. Columns under (N) refer to SEQ ID NO. Column (M) refers to protein name (TIC#). The percent amino acid identity between all pairs is calculated and is represented by the first number in each box. The second number (in parentheses) in each box represents the number of identical amino acids between the pair.

The full-length and mature proteins of the TIC3668-type protein toxin class can also be related by primary structure (conserved amino acid motifs), by length (about 295 amino acids for the mature proteins and about 317 amino acids for the full-length proteins) and by other characteristics. The full-length proteins, TIC3668, TIC3670, TIC3669, TIC4076, TIC4346, TIC4861, TIC4862, TIC4863, TIC4826, TIC4078, and TIC4260 from the present invention have a measured mass of about 35k-Daltons when run on protein gels under denaturing conditions, and the mature proteins have a measured mass of about 32 kDa. Characteristics of the full-length and mature forms of the TIC3668-type protein toxin class, for example, TIC3668, TIC3670, TIC3669, TIC4076, TIC4346, TIC4861, TIC4862, TIC4863, TIC4826, TIC4078, and TIC4260 are reported in Tables 4 and 5.

TABLE 4

| | | | | | Characteristics of Full-length Protein | | | |
|---|---|---|---|---|---|---|---|---|
| Protein | Molecular Weight (in Daltons) | Amino Acid Length | Isoelectric Point | Charge at PH 7.0 | No. of Strongly Basic (—) Amino Acids | No. of Strongly Acidic Amino Acids | No. of Hydrophobic Amino Acids | No. of Polar Amino Acids |
| TIC3668 | 34770.96 | 317 | 9.049 | 5.229 | 34 | 29 | 95 | 111 |
| TIC3669 | 34769.91 | 317 | 8.898 | 4.231 | 34 | 30 | 95 | 111 |
| TIC3670 | 34788.89 | 320 | 8.898 | 4.231 | 34 | 30 | 93 | 112 |
| TIC4076 | 34652.83 | 317 | 8.721 | 3.232 | 32 | 29 | 95 | 112 |
| TIC4078 | 34676.86 | 317 | 8.936 | 4.397 | 32 | 28 | 96 | 110 |
| TIC4260 | 34743.98 | 317 | 9.077 | 5.395 | 33 | 28 | 96 | 109 |
| TIC4826 | 34734.97 | 317 | 8.899 | 4.231 | 33 | 29 | 95 | 111 |
| TIC4861 | 33448.24 | 306 | 8.439 | 2.233 | 31 | 29 | 87 | 110 |
| TIC4862 | 34392.43 | 315 | 8.439 | 2.233 | 31 | 29 | 94 | 112 |
| TIC4863 | 34648.77 | 317 | 8.899 | 4.231 | 33 | 29 | 94 | 112 |
| TIC4346 | 34717.95 | 317 | 8.437 | 2.235 | 32 | 30 | 97 | 109 |

TABLE 5

| | | | | | No. of Strongly Basic Amino Acids | No. of Strongly Acidic Amino Acids | No. of Hydrophobic Amino Acids | No. of Polar Amino Acids |
|---|---|---|---|---|---|---|---|---|
| Protein | Molecular Weight (in Daltons) | Amino Acid Length | Isoelectric Point | Charge at PH 7.0 | | | | |
| mTIC3668 | 32317.06 | 295 | 8.722 | 3.064 | 32 | 29 | 83 | 104 |
| mTIC3669 | 32303.95 | 295 | 8.436 | 2.067 | 32 | 30 | 82 | 105 |
| mTIC3670 | 32334.99 | 295 | 8.436 | 2.067 | 32 | 30 | 81 | 105 |
| mTIC4076 | 32186.87 | 295 | 8.000 | 1.068 | 30 | 29 | 82 | 106 |
| mTIC4078 | 32222.96 | 295 | 8.466 | 2.233 | 30 | 28 | 84 | 103 |
| mTIC4260 | 32290.07 | 295 | 8.747 | 3.230 | 31 | 28 | 84 | 102 |
| mTIC4826 | 32269.01 | 295 | 8.436 | 2.066 | 31 | 29 | 82 | 105 |
| mTIC4861 mTIC4862 mTIC4863 | 32182.81 | 295 | 8.436 | 2.066 | 31 | 29 | 81 | 106 |
| mTIC4346 | 32251.99 | 295 | 7.092 | 0.071 | 30 | 30 | 84 | 103 |

The proteins of the disclosed TIC3668-type protein toxin class represent a new class of insecticidal proteins. With reference to Table 6, all of the numbers above the diagonal line corresponding to 100% identity, represent the number of amino acid differences between the corresponding proteins being compared at the intersection of that particular row and column. The numbers below the diagonal line corresponding to 100% identity represent the percent identity of the corresponding proteins being compared at the intersection of that particular row and column. The mature length members of this protein class exhibit no greater than 90.54% amino acid identity to any other insecticidal protein known in the art, as demonstrated in the alignment provided in Table 6.

The insecticidal protein exhibiting the nearest identity to any of the mature length proteins of the present invention is SEQ ID NO:50 in U.S. Patent Application Publication number 20110030093 (AXMI-209) with 90.5% sequence identity to mTIC4076, mTIC4346, mTIC4826, and mTIC4863. This disclosure only teaches activity against Lepidoptera, while exemplary proteins of the present invention demonstrate activity against Coleoptera. HOUDD3_BRELA, F7TVP6_BRELA, and U4WSU1_BRELA are unannotated protein sequences predicted from the open reading frame in genome sequences reported as having been obtained from *B. laterosporus*. No insecticidal activity is reported for these proteins.

TABLE 6

Alignment of Mature Length TIC3668 Proteins to Prior Art Proteins

| | | 1 | 2 | 3 | 4 | 5 | 6 | 7 | 8 | 9 | 10 | 11 | 12 | 13 |
|---|---|---|---|---|---|---|---|---|---|---|---|---|---|---|
| mTIC3668 | 1 | 100 | 6 | 2 | 11 | 18 | 12 | 8 | 8 | 10 | 36 | 32 | 32 | 33 |
| mTIC3669 | 2 | 98.0 | 100 | 4 | 10 | 16 | 14 | 10 | 8 | 9 | 35 | 32 | 32 | 32 |
| mTIC3670 | 3 | 99.3 | 98.6 | 100 | 9 | 16 | 14 | 8 | 6 | 8 | 34 | 30 | 30 | 31 |
| mTIC4076 | 4 | 96.3 | 96.6 | 97.0 | 100 | 11 | 20 | 5 | 6 | 6 | 30 | 28 | 30 | 29 |
| mTIC4078 | 5 | 93.9 | 94.6 | 94.6 | 96.3 | 100 | 12 | 11 | 12 | 13 | 37 | 34 | 36 | 34 |
| mTIC4260 | 6 | 95.9 | 95.3 | 95.3 | 93.2 | 95.9 | 100 | 19 | 20 | 22 | 48 | 44 | 44 | 43 |
| mTIC4346 | 7 | 97.3 | 96.6 | 97.3 | 98.3 | 96.3 | 93.6 | 100 | 4 | 6 | 30 | 26 | 28 | 29 |
| mTIC4826 | 8 | 97.3 | 97.3 | 98.0 | 98.0 | 95.9 | 93.2 | 98.6 | 100 | 4 | 30 | 24 | 24 | 25 |
| mTIC4863 | 9 | 96.6 | 97.0 | 97.3 | 98.0 | 95.6 | 92.5 | 98.0 | 98.6 | 100 | 30 | 28 | 28 | 27 |
| AXMI-209 | 10 | 88.6 | 89.0 | 89.3 | 90.5 | 88.3 | 84.9 | 90.5 | 90.5 | 90.4 | 100 | 6 | 8 | 7 |
| H0UDD3_BRELA | 11 | 89.9 | 89.9 | 90.5 | 91.2 | 89.3 | 86.1 | 91.8 | 92.4 | 91.2 | 98.1 | 100 | 2 | 3 |
| F7TVP6_BRELA | 12 | 89.9 | 89.9 | 90.5 | 90.5 | 88.6 | 86.1 | 91.2 | 92.4 | 91.2 | 97.5 | 99.4 | 100 | 3 |
| U4WSU1_BRELA | 13 | 89.6 | 89.9 | 90.2 | 90.9 | 89.3 | 86.4 | 90.9 | 92.1 | 91.5 | 97.8 | 99.1 | 99.1 | 100 |

Table 7 below presents additional TIC3668-related toxins. With reference to Table 7, all of the numbers above the diagonal line corresponding to 100% identity, represent the number of amino acid differences between the corresponding proteins being compared at the intersection of that particular row and column. The numbers below the diagonal line corresponding to 100% identity represent the percent identity of the corresponding proteins being compared at the intersection of that particular row and column. The mature length members of these proteins in the TIC3668-related toxin class also exhibit no greater than 90.5% amino acid identity to AXMI-209 (SEQ ID NO:50 in U.S. Patent Application Publication number 20110030093).

by common function and exhibit insecticidal activity towards Coleoptera and Lepidoptera insect species, including adults, pupae, larvae and neonates.

Recombinant polynucleotide compositions that encode TIC3668-type proteins are contemplated. For example, TIC3668-type proteins can be expressed with recombinant DNA constructs in which a polynucleotide molecule with an ORF encoding the protein is operably linked to genetic expression elements such as a promoter and any other regulatory element necessary for expression in the system for which the construct is intended. Non-limiting examples include a plant-functional promoter operably linked to the TIC3668-type protein encoding sequences for expression of

TABLE 7

| Mature Toxin | | 1 | 2 | 3 | 4 | 5 | 6 | 7 | 8 | 9 | 10 | 11 | 12 | 13 | 14 | 15 | 17 |
|---|---|---|---|---|---|---|---|---|---|---|---|---|---|---|---|---|---|
| mTIC7513 | 1 | 100 | 1 | 3 | 3 | 1 | 2 | 5 | 3 | 4 | 3 | 4 | 8 | 9 | 7 | 34 | 9 |
| mTIC7524 | 2 | 99.7 | 100 | 2 | 3 | 2 | 3 | 6 | 4 | 5 | 4 | 5 | 7 | 8 | 6 | 35 | 10 |
| mTIC11239 | 3 | 99 | 99.3 | 100 | 3 | 3 | 5 | 6 | 4 | 5 | 4 | 6 | 5 | 6 | 4 | 35 | 10 |
| mTIC7429 | 4 | 99 | 99 | 99 | 100 | 3 | 5 | 6 | 4 | 5 | 4 | 6 | 6 | 7 | 5 | 33 | 10 |
| mTIC11243 | 5 | 99.7 | 99.3 | 98.6 | 98.6 | 100 | 1 | 4 | 2 | 5 | 4 | 5 | 9 | 10 | 8 | 35 | 10 |
| mTIC7535 | 6 | 99.3 | 99 | 98.3 | 98.3 | 99.7 | 100 | 5 | 3 | 4 | 3 | 6 | 10 | 11 | 9 | 36 | 9 |
| mTIC4544 | 7 | 98.3 | 98 | 98 | 98 | 98.6 | 98.3 | 100 | 2 | 5 | 6 | 7 | 11 | 12 | 10 | 36 | 9 |
| mTIC6871 | 8 | 99 | 98.6 | 98.6 | 98.6 | 99.3 | 99 | 99.3 | 100 | 5 | 4 | 5 | 9 | 10 | 8 | 34 | 9 |
| mTIC7497 | 9 | 98.6 | 98.3 | 98.3 | 98.3 | 98.3 | 98.6 | 98.3 | 98.3 | 100 | 1 | 7 | 8 | 9 | 7 | 34 | 5 |
| mTIC7528 | 10 | 99 | 98.6 | 98.6 | 98.6 | 98.6 | 99 | 98 | 98.6 | 99.7 | 100 | 6 | 7 | 8 | 6 | 33 | 6 |
| mTIC11256 | 11 | 98.6 | 98.3 | 98 | 98 | 98.3 | 98 | 97.6 | 98.3 | 97.6 | 98 | 100 | 7 | 8 | 6 | 31 | 10 |
| mTIC7518 | 12 | 97.3 | 97.6 | 98.3 | 98 | 96.9 | 96.6 | 96.3 | 96.9 | 97.3 | 97.6 | 97.6 | 100 | 1 | 1 | 30 | 13 |
| mTIC7526 | 13 | 96.9 | 97.3 | 98 | 97.6 | 96.6 | 96.3 | 95.9 | 96.6 | 96.9 | 97.3 | 97.3 | 99.7 | 100 | 2 | 31 | 14 |
| mTIC4545 | 14 | 97.6 | 98 | 98.6 | 98.3 | 97.3 | 96.9 | 96.6 | 97.3 | 97.6 | 98 | 98 | 99.7 | 99.3 | 100 | 31 | 12 |
| AXMI-209 | 15 | 89.3 | 89 | 89 | 89.6 | 89 | 88.6 | 88.6 | 89.3 | 89.3 | 89.6 | 90.2 | 90.5 | 90.2 | 90.2 | 100 | 29 |
| mTIC7511 | 16 | 96.9 | 96.6 | 96.6 | 96.6 | 96.6 | 96.9 | 96.9 | 96.9 | 98.3 | 98 | 96.6 | 95.6 | 95.3 | 95.9 | 29 | 100 |

The TIC3668 proteins disclosed in this application exhibit activity in diet bioassays against Coleoptera, including WCR. In some cases Lepidopteran activity is also observed.

As described further in the Examples of this application, polynucleotide sequences encoding TIC3668 toxin proteins were designed for use in plants. Exemplary polynucleotides that were designed for expression in plants and encode the full-length of the insect inhibitory TIC3668, TIC3669, TIC3670, TIC4260, TIC4076, TIC4078, TIC4346, TIC4826, TIC4861, TIC4862, and TIC4863 proteins are set forth in SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, and SEQ ID NO:51. Exemplary polynucleotides that were designed for expression in plants and encode a mature form of the insect inhibitory mTIC3668, mTIC3669, mTIC3670, mTIC4260, mTIC4076, mTIC4078, mTIC4346, mTIC4826, mTIC4861, mTIC4862, and mTIC4863 proteins are set forth in SEQ ID NO:33, SEQ ID NO:35, SEQ ID NO:37, SEQ ID NO:39, SEQ ID NO:41, SEQ ID NO:43, SEQ ID NO:45, SEQ ID NO:47, and SEQ ID NO:49.

Expression cassettes and vectors containing these polynucleotide sequences were constructed and introduced into corn plant cells in accordance with transformation methods and techniques known in the art. Transformed cells were regenerated into transformed plants that were observed to be expressing TIC3668 toxin proteins. To test pesticidal activity, bioassays were performed in the presence of Lepidopteran or Coleopteran pest larvae using plant leaf disks obtained from the transformed plants.

The insect inhibitory activity of exemplary members of the TIC3668-type protein toxin class is described in more detail in the Examples. The exemplary proteins are related the protein in plants or a Bt-functional promoter operably linked to a TIC3668-type protein encoding sequence for expression of the protein in a Bt bacterium or other Bacillus species. Other elements can be operably linked to the TIC3668-type protein encoding sequences including, but not limited to, enhancers, introns, untranslated leaders, encoded protein immobilization tags (HIS-tag), translocation peptides (i.e., plastid transit peptides, signal peptides), polypeptide sequences for post-translational modifying enzymes, ribosomal binding sites, and RNAi target sites. Exemplary recombinant polynucleotide molecules provided herewith include, but are not limited to, a heterologous promoter operably linked to a polynucleotide such as SEQ ID NO:1, SEQ ID NO:3, SEQ ID NO:5, SEQ ID NO:7, SEQ ID NO:9, SEQ ID NO:11, SEQ ID NO:13, SEQ ID NO: 15, SEQ ID NO: 17, SEQ ID NO: 19, SEQ ID NO:21, SEQ ID NO:73, SEQ ID NO:75, SEQ ID NO: 77, SEQ ID NO: 79, SEQ ID NO: 81, SEQ ID NO: 83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, and SEQ ID NO:101 that encodes the respective polypeptides or proteins having the amino acid sequence as set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO: 100, and SEQ ID NO:102. The codons of a recombinant polynucleotide molecule encoding for proteins disclosed herein can be substituted by synonymous codons (known in the art as a silent substitution). Non-limiting examples for modified polynucleotides encoding any of the TIC3668-type proteins disclosed in this application are set forth in SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, and SEQ ID NO:51 for the full-length protein sequences and SEQ ID NOs:33, SEQ ID NO:35, SEQ ID NO:37, SEQ ID NO:39, SEQ ID NO:41, SEQ ID NO:43, SEQ ID NO:45, SEQ ID NO:47, and SEQ ID NO:49 for the mature protein sequences.

A recombinant DNA construct comprising TIC3668-type protein encoding sequences can further comprise a region of DNA that encodes for one or more insect inhibitory agents which can be configured to concomitantly express or co-express with a DNA sequence encoding a TIC3668-type protein, a protein different from a TIC3668-type protein, an insect inhibitory dsRNA molecule, or an ancillary protein. Ancillary proteins include, but are not limited to, co-factors, enzymes, binding-partners, or other agents that function to aid in the effectiveness of an insect inhibitory agent, for example, by aiding its expression, influencing its stability in plants, optimizing free energy for oligomerization, augmenting its toxicity, and increasing its spectrum of activity. An ancillary protein may facilitate the uptake of one or more insect inhibitory agents, for example, or potentiate the toxic effects of the toxic agent.

A recombinant DNA construct can be assembled so that all proteins or dsRNA molecules are expressed from one promoter or each protein or dsRNA molecules is under separate promoter control or some combination thereof. The proteins of this invention can be expressed from a multi-gene expression system in which one or more proteins of the TIC3668-proteins are expressed from a common nucleotide segment which also contains other open reading frames and promoters, depending on the type of expression system selected. For example, a bacterial multi-gene expression system can utilize a single promoter to drive expression of multiply-linked/tandem open reading frames from within a single operon (i.e., polycistronic expression). In another example, a plant multi-gene expression system can utilize multiply-unlinked expression cassettes each expressing a different protein or other agent such as one or more dsRNA molecules Recombinant polynucleotides or recombinant DNA constructs comprising a TIC3668-type protein encoding sequence can be delivered to host cells by vectors, e.g., a plasmid, baculovirus, synthetic chromosome, virion, cosmid, phagemid, phage, or viral vector. Such vectors can be used to achieve stable or transient expression of a TIC3668-type protein encoding sequence in a host cell, or subsequent expression of the encoded polypeptide. An exogenous recombinant polynucleotide or recombinant DNA construct that comprises a TIC3668-type protein encoding sequence and that is introduced into a host cell is referred herein as a "transgene".

Transgenic bacteria, transgenic plant cells, transgenic plants, and transgenic plant parts that contain a recombinant polynucleotide that expresses any one or more of the TIC3668-type protein encoding sequences are provided herein. The term "bacterial cell" or "bacterium" can include, but is not limited to, an *Agrobacterium*, a *Bacillus*, an *Escherichia*, a *Salmonella*, a *Pseudomonas*, or a *Rhizobium* cell. The term "plant cell" or "plant" can include but is not limited to a monocotyledon, dicotyledon, alfalfa, banana, barley, bean, broccoli, cabbage, *brassica*, carrot, cassava, castor, cauliflower, celery, chickpea, Chinese cabbage, citrus, coconut, coffee, corn, clover, cotton, a cucurbit, cucumber, Douglas fir, eggplant, cucalyptus, flax, garlic, grape, hops, leek, lettuce, Loblolly pine, millets, melons, nut, oat, olive, onion, ornamental, palm, pasture grass, pea, peanut, pepper, pigeonpea, pine, potato, poplar, pumpkin, *Radiata* pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat plant cell or plant. In certain embodiments, transgenic plants and transgenic plant parts regenerated from a transgenic plant cell are provided. In certain embodiments, the transgenic plants can be obtained from a transgenic seed, by cutting, snapping, grinding or otherwise disassociating the part from the plant. In certain embodiments, the plant part can be a seed, a boll, a leaf, a flower, a stem, a root, or any portion thereof, or a non-regenerable portion of a transgenic plant part. As used in this context, a "non-regenerable" portion of a transgenic plant part is a portion that can not be induced to form a whole plant or that can not be induced to form a whole plant that is capable of sexual and/or asexual reproduction. In certain embodiments, a non-regenerable portion of a plant part is a portion of a transgenic seed, boll, leaf, flower, stem, or root.

Methods of making transgenic plants that comprise insect, Coleoptera- or Lepidoptera-inhibitory amounts of a TIC3668-type protein are provided. Such plants can be made by introducing a recombinant polynucleotide that encodes any of the TIC3668-type proteins provided in this application into a plant cell, and selecting a plant derived from said plant cell that expresses an insect, Coleoptera- or Lepidoptera-inhibitory amount of the TIC3668-type proteins. Plants can be derived from the plant cells by regeneration, seed, pollen, or meristem transformation techniques. Methods for transforming plants are known in the art.

Processed plant products, wherein the processed product comprises a detectable amount of a TIC3668-type protein, an insect inhibitory segment or fragment thereof, or any distinguishing portion thereof, are also disclosed in this application. In certain embodiments, the processed product is selected from the group consisting of plant parts, plant biomass, oil, meal, sugar, animal feed, flour, flakes, bran, lint, hulls, processed seed, and seed. In certain embodiments, the processed product is non-regenerable. The plant product can comprise commodity or other products of commerce derived from a transgenic plant or transgenic plant part, where the commodity or other products can be tracked through commerce by detecting nucleotide segments or expressed RNA or proteins that encode or comprise distinguishing portions of a TIC3668-type protein.

Plants expressing the TIC3668 proteins can be crossed by breeding with transgenic events expressing other toxin proteins and/or expressing other transgenic traits such as herbicide tolerance genes, genes conferring yield or stress tolerance traits, and the like, or such traits can be combined in a single vector so that the traits are all linked.

TIC3668-type protein-encoding sequences and sequences having a substantial percentage identity to TIC3668-type protein-encoding sequences can be identified using methods known to those of ordinary skill in the art such as polymerase chain reaction (PCR), thermal amplification and hybridization. For example, the proteins of the TIC3668-type protein toxin class can be used to produce antibodies that bind specifically to this class of proteins, and can be used to screen for and to find other members of the class.

Further, nucleotide sequences encoding the TIC3668-type protein toxin class (and reverse complement sequences) can be used as probes and primers for screening to identify other members of the class using thermal-cycle or isothermal amplification and hybridization methods. Specifically, oligonucleotides derived from sequences as set forth in any of SEQ ID NOs:52 through 61 can be used to determine the presence or absence of a TIC3668-type transgene in a deoxyribonucleic acid sample derived from a commodity product. Given the sensitivity of certain nucleic acid detection methods that employ oligonucleotides, it is anticipated that oligonucleotides derived from sequences as set forth in any of SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, and SEQ ID NO:61 can be used to detect a TIC3668, TIC3669, TIC3670, TIC4076, TIC4078, or TIC4260 transgene in commodity products derived from pooled sources where only a fraction of the commodity product is derived from a transgenic plant containing any of SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, and SEQ ID NO:61. It is further recognized that such oligonucleotides can be used to introduce nucleotide sequence variation in each of SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, and SEQ ID NO:61. Such "mutagenesis" oligonucleotides are useful for identification of TIC3668, TIC3669, TIC3670, TIC4076, TIC4078, or TIC4260, amino acid sequence variants exhibiting a range of insect inhibitory activity or varied expression in transgenic plant host cells.

Nucleotide sequence homologs, e.g., insecticidal proteins encoded by nucleotide sequences that hybridize to each or any of the sequences disclosed in this application under stringent hybridization conditions, are also an embodiment of the present invention. The invention also provides a method for detecting a first nucleotide sequence that hybridizes to a second nucleotide sequence, wherein the first nucleotide sequence (or its reverse complement sequence) encodes an insecticidal protein or insecticidal fragment thereof and hybridizes under stringent hybridization conditions to the second nucleotide sequence. In such case, the second nucleotide sequence can be any of the nucleotide sequences disclosed in the TIC3668-type protein toxin class under stringent hybridization conditions. Nucleotide coding sequences hybridize to one another under appropriate hybridization conditions and the proteins encoded by these nucleotide sequences cross react with antiserum raised against any one of the other proteins. Stringent hybridization conditions are known in the art and may vary according to the desired application and outcome and may encompass a variety of reagents and conditions. For instance, washes at higher temperatures constitute more stringent conditions. In certain embodiments, hybridization conditions of the present invention may comprise at least hybridization at 42° C. followed by two washes for five minutes each at room temperature with 2×SSC, 0.1% SDS, followed by two washes for thirty minutes each at 65° C. in 0.5×SSC, 0.1% SDS; or hybridization at 68° C., followed by washing at 68° C., in 2×SSC containing 0.1% SDS; or hybridization from 4 to 12 hours in 50% formamide, 1 M NaCl, and 1% SDS at 37 C, and a wash in 0.1×SSC at 60 C-65 C.

One skilled in the art will recognize that, due to the redundancy of the genetic code, many other sequences are capable of encoding such related proteins, and those sequences, to the extent that they function to express insecticidal proteins either in Bacillus strains or in plant cells, are embodiments of the present invention, recognizing of course that many such redundant coding sequences will not hybridize under these conditions to the native Bacillus sequences encoding TIC3668. This application contemplates the use of these, and other identification methods known to those of ordinary skill in the art, to identify TIC3668-type protein-encoding sequences and sequences having a substantial percentage identity to TIC3668-type protein-encoding sequences.

This disclosure also contemplates the use of molecular methods known in the art to engineer and clone commercially useful proteins comprising chimeras of proteins from pesticidal proteins; e.g., the chimeras may be assembled from segments of the TIC3668-type proteins to derive additional useful embodiments including assembly of segments of TIC3668-type proteins with segments of diverse proteins different from TIC3668 and related proteins. The TIC3668-type protein class may be subjected to alignment to each other and to other Bacillus pesticidal proteins (whether or not these are closely or distantly related phylogenetically), and segments of each such protein may be identified that are useful for substitution between the aligned proteins, resulting in the construction of chimeric proteins. Such chimeric proteins can be subjected to pest bioassay analysis and characterized for the presence or absence of increased bioactivity and/or expanded target pest spectrum compared to the parent proteins from which each such segment in the chimera was derived. The pesticidal activity of the polypeptides may be further engineered for activity to a particular pest or to a broader spectrum of pests by swapping domains or segments with other proteins or by using directed evolution methods known in the art.

Methods of controlling insects, in particular Lepidoptera or Coleoptera infestations of crop plants, with proteins from the TIC3668 toxin protein class are also disclosed in this application. Such methods can comprise growing a plant comprising an insect-, Coleoptera- or Lepidoptera-inhibitory amount of a protein of the TIC3668 toxin protein class. In certain embodiments, such methods can further comprise any one or more of: (i) applying any composition comprising or encoding a protein of the TIC3668-type protein toxin class to a plant or a seed that gives rise to a plant; and (ii) transforming a plant or a plant cell that gives rise to a plant with a polynucleotide encoding a protein of the TIC3668-type protein toxin class. In general, it is contemplated that any protein in the TIC3668-type protein toxin class can be provided in a composition, provided in a microorganism, or provided in a transgenic plant to confer insect inhibitory activity against Lepidopteran or Coleopteran insects.

In certain embodiments, a recombinant polypeptide of the TIC3668-type protein toxin class is the insecticidally active ingredient of an insect inhibitory composition prepared by culturing recombinant Bacillus or any other recombinant bacterial cell transformed to express a TIC3668-type protein toxin under conditions suitable to express and produce proteins of the TIC3668-type protein toxin class. Such a composition can be prepared by desiccation, lyophilization, homogenization, extraction, filtration, centrifugation, sedimentation, or concentration of a culture of such recombinant cells expressing/producing said recombinant polypeptide. Such a process can result in a Bacillus or other entomopathogenic bacterial cell extract, cell suspension, cell homogenate, cell lysate, cell supernatant, cell filtrate, or cell pellet. By obtaining the recombinant polypeptides so produced, a composition that includes the recombinant polypeptides can include bacterial cells, bacterial spores, and parasporal inclusion bodies and can be formulated for various uses, including as agricultural insect inhibitory spray products or as insect inhibitory formulations in diet bioassays.

In one embodiment, to reduce the likelihood of resistance development, an insect inhibitory composition comprising one or more proteins from the TIC3668-type protein toxin class can further comprise at least one additional polypeptide that exhibits insect inhibitory activity against the same Lepidopteran or Coleopteran insect species, but which is different from the TIC3668-type protein toxin. Possible additional polypeptides for such a composition include an insect inhibitory protein and an insect inhibitory dsRNA molecule. One example for the use of such ribonucleotide sequences to control insect pests is described in Baum, et al. (U.S. Patent Publication 2006/0021087 A1). Such additional polypeptide for the control of Lepidopteran pests may be selected from the group consisting of an insect inhibitory protein, such as, but not limited to, Cry1A (U.S. Pat. No. 5,880,275), Cry1Ab, Cry1Ac, Cry1A.105, Cry1Ac, Cry1B (U.S. patent Publication Ser. No. 10/525,318), Cry1C (U.S. Pat. No. 6,033,874), Cry1D, Cry1Da and variants thereof, Cry1E, Cry1F, and Cry1A/F chimeras (U.S. Pat. Nos. 7,070, 982; 6,962,705; and 6,713,063), Cry1G, Cry1H, Cry1I, Cry1J, Cry1K, Cry1L, Cry1-type chimeras such as, but not limited to, TIC836, TIC860, TIC867, TIC869 and TIC1100, Cry2A, Cry2Ab (U.S. Pat. No. 7,064,249), Cry2Ac, Cry4B, Cry6, Cry7, Cry8, Cry9, Cry15, Cry43A, Cry43B, Cry51Aa1, ET66, TIC400, TIC400, TIC800, TIC834, TIC1415, Vip3A, VIP3Ab, VIP3B, AXMI-184, AXMI-196, DIG-3, DIG-4, DIG-5, DIG-11, AfIP-1A and derivatives thereof (U.S. Patent Publication 2014-0033361 A1), AfIP-1B and derivatives thereof (U.S. Patent Publication 2014-0033361 A1), PIP-1APIP-1B (U.S. Patent Publication 2014-0007292 A1), PSEEN3174 (U.S. Patent Publication 2014-0007292 A1), AECFG-592740 (U.S. Patent Publication 2014-0007292 A1), Pput_1063 (U.S. Patent Publication 2014-0007292 A1), Pput_1064 (U.S. Patent Publication 2014-0007292 A1), GS-135 and derivatives thereof (U.S. Patent Publication 2012-0233726 A1), GS153 and derivatives thereof (U.S. Patent Publication 2012-0192310 A1), GS154 and derivatives thereof (U.S. Patent Publication 2012-0192310 A1), GS155 and derivatives thereof (U.S. Patent Publication 2012-0192310 A1), SEQ ID NO:2 and derivatives thereof as described in U.S. Patent Publication 2012-0167259 A1, SEQ ID NO:2 and derivatives thereof as described in U.S. Patent Publication 2012-0047606 A1, SEQ ID NO:2 and derivatives thereof as described in U.S. Patent Publication 2011-0154536 A1, SEQ ID NO:2 and derivatives thereof as described in U.S. Patent Publication 2011-0112013 A1, SEQ ID NO:2 and 4 and derivatives thereof as described in U.S. Patent Publication 2010-0192256 A1, SEQ ID NO:2 and derivatives thereof as described in U.S. Patent Publication 2010-0077507 A1, SEQ ID NO:2 and derivatives thereof as described in U.S. Patent Publication 2010-0077508 A1, SEQ ID NO:2 and derivatives thereof as described in U.S. Patent Publication 2009-0313721 A1, SEQ ID NO:2 or 4 and derivatives thereof as described in U.S. Patent Publication 2010-0269221 A1, SEQ ID NO:2 and derivatives thereof as described in U.S. Pat. No. 7,772,465 (B2), CF161_0085 and derivatives thereof as described in WO2014/008054 A2, Lepidopteran toxic proteins and their derivatives as described in US Patent Publications US2008-0172762 A1, US2011-0055968 A1, and US2012-0117690 A1; SEQ ID NO:2 and derivatives thereof as described in U.S. Pat. No. 7,510,878(B2), SEQ ID NO:2 and derivatives thereof as described in U.S. Pat. No. 7,812,129(B1); and other Lepidopteran-inhibitory proteins known to those of ordinary skill in the art. Such additional polypeptide for the control of Coleopteran pests may be selected from the group consisting of an insect inhibitory protein, such as, but not limited to, Cry3Bb (U.S. Pat. No. 6,501,009), Cry1C variants, Cry3A variants, Cry3, Cry3B, Cry34/35, 5307, Axmi184, Axmi205, AxmiR1, TIC407, TIC417, TIC431, TIC807, TIC853, TIC901, TIC1201, TIC3131, DIG-10, eHIPs (U.S. Patent Application Publication No. 2010/0017914) and other Colcopteran-inhibitory proteins known to those of ordinary skill in the art.

In other embodiments, such composition/formulation can further comprise at least one additional polypeptide that exhibits insect inhibitory activity to an insect that is not inhibited by an otherwise insect inhibitory protein of the present invention to expand the spectrum of insect inhibition obtained. For example, for the control of Hemipteran pests, combinations of insect inhibitory proteins of the present invention can be used with Hemipteran-active proteins such as TIC1415 (US Patent Application Publication No. 2013/0097735), TIC807 (U.S. Pat. No. 8,609,936), TIC834 (U.S. Patent Application Publication No. 2013/0269060) and other Hemipteran-active proteins known to those of ordinary skill in the art. Additional polypeptides for the control of Coleopteran, Lepidopteran, and Hemipteran insect pests can be found on the *Bacillus thuringiensis* toxin nomenclature website maintained by Neil Crickmore (on the world wide web at btnomenclature.info).

The possibility for insects to develop resistance to certain insecticides has been documented in the art. One insect resistance management strategy is to employ transgenic crops that express two distinct insect inhibitory agents that operate through different modes of action. Therefore, any insects with resistance to either one of the insect inhibitory agents can be controlled by the other insect inhibitory agent. Another insect resistance management strategy employs the use of plants that are not protected to the targeted Coleopteran or Lepidopteran pest species to provide a refuge for such unprotected plants. One particular example is described in U.S. Pat. No. 6,551,962, which is incorporated by reference in its entirety.

Other embodiments such as topically applied pesticidal chemistries that are designed for controlling pests that are also controlled by the proteins disclosed herein to be used with proteins in seed treatments, spray on, drip on, or wipe on formulations can be applied directly to the soil (a soil drench), applied to growing plants expressing the proteins disclosed herein, or formulated to be applied to seed containing one or more transgenes encoding one or more of the proteins disclosed. Such formulations for use in seed treatments can be applied with various stickers and tackifiers known in the art. Such formulations can contain pesticides that are synergistic in mode of action with the proteins disclosed, so that the formulation pesticides act through a different mode of action to control the same or similar pests that can be controlled by the proteins disclosed, or that such pesticides act to control pests within a broader host range or plant pest species that are not effectively controlled by the TIC3668-type protein toxin class.

The aforementioned composition/formulation can further comprise an agriculturally-acceptable carrier, such as a bait, a powder, dust, pellet, granule, spray, emulsion, a colloidal suspension, an aqueous solution, a *Bacillus* spore/crystal preparation, a seed treatment, a recombinant plant cell/plant tissue/seed/plant transformed to express one or more of the proteins, or bacterium transformed to express one or more of the proteins. Depending on the level of insect inhibitory or insecticidal inhibition inherent in the recombinant polypeptide and the level of formulation to be applied to a plant or diet assay, the composition/formulation can include various by weight amounts of the recombinant polypeptide, e.g.

from 0.0001% to 0.001% to 0.01% to 1% to 99% by weight of the recombinant polypeptide.

EXAMPLES

In view of the foregoing, those of skill in the art should appreciate that changes can be made in the specific aspects which are disclosed and still obtain a like or similar result without departing from the spirit and scope of the invention. Thus, specific structural and functional details disclosed herein are not to be interpreted as limiting. It should be understood that the entire disclosure of each reference cited herein is incorporated within the disclosure of this application.

Example 1

Discovery of the TIC3668-Related Protein Toxin Class

Bacterial strains exhibiting distinctive attributes, e.g., inferred toxicity, proteomic diversity, and morphological variations when compared with each other, were identified and prepared for genome sequencing using methods well known in the art. A protein TIC3668 (SEQ ID NO:2) exhibiting inhibitory activity against Coleopteran insects in in vitro bioassays was discovered from a *Brevibacillus laterosporus* (*B. laterosporus*) strain EG5552. Other strains were also found to contain proteins that resemble TIC3668. Polynucleotide segments encoding these proteins were cloned, and inserted into a recombinant host strain to test for expression.

Thermal amplification primers were designed to amplify a full-length copy of the gene from the total genomic DNA of different *B. laterosporus* bacterial strains, including EG5552. Separate thermal amplification products (amplicons) were generated from each strain and these were analyzed for the presence of open reading frames that could encode TIC3668-related proteins. Each amplicon was determined to have a single open reading frame, containing a translation initiation codon, followed in frame by a contiguous open reading frame, that terminated with an in-frame translation termination codon. The deduced amino acid sequences obtained from each of these additional different bacterial strains are set forth respectively in SEQ ID NO:2 (TIC3668), SEQ ID NO:4 (TIC3669), SEQ ID NO:6 (TIC3670), SEQ ID NO:8 (TIC4076), SEQ ID NO:10 (TIC4078), SEQ ID NO:14 (TIC4346), SEQ ID NO:16 (TIC4826), SEQ ID NO:18 (TIC4861), SEQ ID NO:20 (TIC4862), SEQ ID NO:22 (TIC4863) SEQ ID NO:74 (TIC11239), SEQ ID NO:76 (TIC11243), SEQ ID NO:78 (TIC11256), SEQ ID NO:80 (TIC4544), SEQ ID NO:82 (TIC4545), SEQ ID NO:84 (TIC6871), SEQ ID NO:86 (TIC7429), SEQ ID NO:88 (TIC7497), SEQ ID NO:90 (TIC7511), SEQ ID NO:92 (TIC7513), SEQ ID NO:94 (TIC7518), SEQ ID NO:96 (TIC7524), SEQ ID NO:98 (TIC7526), SEQ ID NO: 100 (TIC7528), and SEQ ID NO:102 (TIC7535). These amplicons were cloned into a recombinant *Bacillus thuringiensis* (Bt) plasmid expression vector downstream of a sporulation specific expression promoter and transformed into an acrystalliferous Bt host cell. The amplicons were also cloned into an *E. coli* expression system. The resulting recombinant strains were observed to express a recombinant protein.

Example 2

Coleopteran Activity of TIC3668-Related Protein Toxin Class

This Example illustrates inhibitory activity exhibited by TIC3668-like proteins against Coleoptera.

Protein preparations produced from recombinant bacteria as described in Example 1, for the full-length proteins of TIC3668, TIC3669, TIC3670, TIC4260, TIC4076 and TIC2462 were submitted for insect diet-overlay bioassays against Colorado Potato Beetle (*Leptinotarsa decemlineata*, CPB) and against at least one corn rootworm species. Known members of corn rootworm species are *Diabrotica virgifera virgifera* (Western Corn Rootworm, WCR), *Diabrotica barberi* (Northern Corn Rootworm, NCR), *Diabrotica virgifera zeae* (Mexican Corn Rootworm, MCR), *Diabrotica* balteata (Brazilian Corn Rootworm (BZR), *Diabrotica* undecimpunctata howardii (Southern Corn Rootworm, SCR) and a Brazilian Corn Rootworm complex (BCR) consisting of *Diabrotica viridula* and *Diabrotica speciosa*).

As demonstrated in Table 8, the results show that TIC3668, TIC3669, TIC3670, TIC4260, and TIC4076 exhibited mortality against corn rootworm. TIC2462 (SEQ ID NO:62 encoding SEQ ID NO:63), a protein closely related to the AXMI-209 protein (compared to TIC2462, >99% identical at the amino acid level, and exhibiting only two amino acid differences), did not exhibit mortality against corn rootworm, thus distinguishing the activity of the TIC3668-like protein toxin class from proteins resembling AXMI-209. Surprisingly, mortality against Colorado Potato Beetle, a species typically tested in bioassays as an indicator of Coleopteran activity, was not observed for any of the proteins tested.

TABLE 8

Observed Mortality against Coleopteran Insect Pests of Exemplary Proteins.

| Toxin | Corn Rootworm | CPB |
|---|---|---|
| TIC2462 | – | – |
| TIC3668, TIC3669, TIC3670 | + | – |
| TIC4260, TIC4076 | + | – |
| TIC4078 | NT | – |
| TIC4346 | + | + |
| TIC4826, TIC4861, TIC4862, TIC4863 | NT | NT |

+ = Mortality observed
– = Mortality not observed
NT = Not tested

Example 3

Mature Form of the TIC3668 Protein Toxin

This Example illustrates the presence of a membrane transiting peptide at the amino terminus of the native proteins within the TIC3668 protein toxin class and the discovery of active mature toxin proteins of the TIC3668 protein toxin class.

Bioinformatic analysis using a SignalP program (Petersen, et. al (2011), Nature Methods, 8:785-786) of the amino acid sequence translation from the TIC3668 coding sequence (SEQ ID NO: 1) predicted the presence of a membrane transiting segment corresponding to the N-terminal first 23 amino acids.

Experiments were designed to confirm the presence of a membrane transiting segment within each member of the TIC3668-like protein toxin class. TIC3668 was cloned into a Bt host cell behind a non-sporulation specific Bt promoter. The resultant culture supernatants were tested for insecticidal activity. Three forms of protein corresponding to TIC3668 were recovered as a mixture from the supernatant. These different fragments of less than full length TIC3668 protein were later determined by mass spectrometry and N-terminal sequence analysis to contain at their respective amino termini, either amino acid 16, 19, or 24, as set forth in SEQ ID NO:2. Only a small amount of these three truncated forms of TIC3668 were detected in the culture media. The most abundant form of the protein detected was observed to have at its amino terminus the serine at position 24, as set forth in SEQ ID NO:2. Concentrated and purified protein from the culture supernatant exhibited bioactivity against WCR when tested in artificial diet bioassay.

Different expression constructs were created for identifying the smallest peptide segment for each TIC3668-type protein exhibiting insecticidal activity. These constructs were introduced into an acrystalliferous *B. thuringiensis* strain or an *E. coli* strain. One construct was designed for expression of the full length TIC3668 protein, as set forth in SEQ ID NO:2 from amino acid 1 through 317, in an acrystalliferous strain of Bt. Constructs were designed for expression of the full-length TIC3668 protein, and various shorter variant forms of the TIC3668 protein, in an *E. coli* expression system having a carboxy terminal HIS tag sequence (HHHHAHHH). The constructs designed for expression in *E. coli* consisted of: (1) a construct designed to express the full length TIC3668 protein as set forth in SEQ ID NO:2 from amino acid position 1 through 317; (2) a construct designed to express a TIC3668 variant protein having from amino acid 16 through 317 as set forth in SEQ ID NO:2; (3) a construct designed to express a TIC3668 variant protein from amino acid 24 through 317 as set forth in SEQ ID NO:2; (4) a construct designed to express a TIC3668 variant protein from amino acid 26 through amino acid 317 as set forth SEQ ID NO:2; (5) a construct designed to express TIC3668 variant protein from amino acid 28 through 317 as set forth in SEQ ID NO:2. Additionally a TIC3668 protein with an N-terminal 10-his tag and a TVMV (tobacco vein mottling virus) protease site (MHHHHHHHHHHHGTETVRFQ) was obtained from an *E. coli* expression system to produce a TIC3668 protein with a start at residue no. 24 as set forth in SEQ ID NO:2.

Protein was obtained from the supernatant of the Bt expression system and subjected to mass spectrometry and N-terminal sequence analysis. The Bt expression system produced the predicted TIC3668 mature toxin from acid 24-317 as set forth in SEQ ID NO:2. Protein was not observed in the *E. coli* supernatants. Protein was obtained from each of the respective *E. coli* expression constructs by osmotic shock to release proteins from the periplasm. Proteins produced from the constructs that were designed to contain amino acid 16 or 24 at the amino terminus of the less than full length protein were confirmed to contain these amino acids at their respective amino terminus. Protein produced from the construct designed to express the full length TIC3668 produced the mature length protein, containing the serine at position 24 as set forth in SEQ ID NO:2 at the amino terminus. Proteins produced from the constructs designed to contain either amino acid 26 or amino acid 28 as set forth in SEQ ID NO:2 as the N-terminal amino acid each surprisingly contained only amino acid 28 as the N-terminal amino acid, suggesting that processing that maintains amino acid number 24 as set forth in SEQ ID NO:2 at the N-terminus may be important for toxin stability.

Protein samples obtained from these expression system analyses were submitted for testing against Western Corn Rootworm larvae in insect diet-overlay bioassays, as described in Example 2. Certain N-terminal truncations from this study were determined to exhibit decreased bioactivity. Specifically, it was observed that the insecticidal activity was significantly reduced when the amino terminal amino acid was 26 or 28, as set forth in SEQ ID NO:2. It can be extrapolated that other TIC3668 protein family members that are N-terminally truncated to be shorter than the mature protein (starting at amino acid residue no. 24 for TIC3668, TIC3669. TIC3670, TIC4076, TIC4078, TIC4260, TIC4346, TIC4826, TIC4863, TIC11239, TIC11243, TIC11256, TIC4544, TIC4545, TIC6871, TIC7429, TIC7497, TIC7511, TIC7513, TIC7518, TIC7524, TIC7526, TIC7528, and TIC7535; starting at amino acid 13 for TIC4861; and starting at amino acid 22 for TIC4862), are the shortest version of the tested TIC3668-type proteins to show insecticidal activity against WCR. All variants of TIC3668 of equal length or longer than the mature protein showed high activity against WCR, even at relatively low concentrations. The data also demonstrates that the *E. coli* processing of TIC3668 varies by construct design.

Example 4

Synthesis of Genes Encoding TIC3668-Type
Proteins for Expression in Plants

Nucleotide sequences encoding full-length and mature versions of a TIC3668 protein, a TIC3669 protein, a TIC3670, a TIC4076, TIC4078, a TIC4260 protein, a TIC4346 protein, a TIC4826 protein, a TIC4861 protein, a TIC4862 protein, and a TIC4863 protein were designed. Nucleotide sequences encoding TIC3668, TIC3669, and TIC3670 were synthesized according to methods generally described in U.S. Pat. No. 5,500,365, avoiding certain inimical problem sequences such as ATTTA and A/T rich plant polyadenylation sequences while preserving the amino acid sequence of the native *B. laterosperous* protein. These nucleotide sequences are provided herein as SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, and SEQ ID NO:51 for the full-length sequences and SEQ ID NO:33, SEQ ID NO:35, SEQ ID NO:37, SEQ ID NO:39, SEQ ID NO:41, SEQ ID NO:43, SEQ ID NO:45, SEQ ID NO:47, and SEQ ID NO:49 for the mature sequences.

Example 5

Expression Cassettes for Expression of
TIC3668-Type Proteins in Plants

A variety of plant expression cassettes were designed with the sequences as set forth in SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO: 46, SEQ ID NO:47, SEQ ID NO:48, SEQ ID NO:49, SEQ ID NO:50, and SEQ ID NO:51. Such expression cassettes are useful for transient expression in plant protoplasts or transformation of plant cells. Typical expression cassettes were designed with respect to the eventual placement of the protein within the cell. One set of expression cassettes was designed in a manner to allow the protein to be translated with the native N-terminal segment. Another set of expression cassettes was designed to allow the expression of the protein without the N-terminal segment (i.e., the mature length protein). Another set of expression cassettes was designed to have a transit peptide expressed in-frame and operably linked to the mature length toxin protein, to allow targeting to an organelle of the cell such as the chloroplast or plastid. All expression cassettes were designed to begin at the 5' end with a promoter which can be comprised of multiple contiguously linked promoter elements, enhancer elements or other expression elements known to those of ordinary skill in the art to boost the expression of the transgene. The promoter sequence was usually followed contiguously with one or more leader sequences 3' to the promoter. An intron sequence was provided 3' to the leader sequence to improve expression of the transgene. A coding sequence for the toxin or transit peptide and coding sequence for the toxin was located 3' of the promoter, leader and intron configuration. A 3'UTR sequence was provided 3' of the coding sequence to facilitate termination of transcription and provides sequences important for the polyadenylation of the resulting transcript. All of the elements described above were arranged contiguously with often additional sequence provided for the construction of the expression cassette such as restriction endonuclease sites or ligation independent cloning sites.

Example 6

Transformation Vectors Containing TIC3668-Type Protein Expression Cassette

*Agrobacterium*-mediated transformation vectors were constructed to deliver DNA to the plant genome that expresses the TIC3668, mTIC3668, TIC3669, mTIC3669, TIC3670, and mTIC3670 proteins. Expression cassettes were cloned into suitable vectors between the *Agrobacterium* border sequences such that they would be transferred to the genome of a host plant cell by *Agrobacterium* hosts containing the construct vectors along with a selectable marker gene. More specifically, the restriction fragment containing the entire cytosolic expression cassette encoding one of the proteins referenced above was cloned into an *Agrobacterium* plant transformation vector. Similarly, the restriction fragment containing the entire plastid targeted expression cassette was cloned into an *Agrobacterium* plant transformation vector. The vectors containing the TIC3668-type protein expression cassettes (i.e., untargeted cassette or targeted cassettes) are introduced into *Agrobacterium* by electroporation or by tri-parental mating.

Expression cassettes containing artificial genes encoding TIC4076, TIC4078, TIC4260, TIC4346, TIC4826, TIC4861, TIC4862, and TIC4863, each with and without sequences encoding the N terminal 23 amino acids present in the native *B. laterosperous* open reading frame (amino acids 1-23 as set forth in SEQ ID NO:2), are cloned into suitable vectors between the *Agrobacterium* border sequences so that they are transferred to the genome of a host cell and tested for expression and bioactivity of the encoded protein.

Example 7

Coleopteran Activity of TIC3668-Type Proteins in Plants

This Example illustrates inhibitory activity exhibited by TIC3668-like proteins against Coleoptera, such as corn rootworm larvae, when expressed in plants and provided as a diet to the respective insect pest.

R0 transgenic corn plants expressing TIC3668, mTIC3668, TIC3669, mTIC3669, TIC3670, and mTIC3670 proteins were produced using vectors containing the expression cassettes described in Example 5.

F1 transgenic corn plants were grown from seed produced by pollinating ears of non-transformed wild-type commercial germplasm plants with pollen from R0 transformants. After being transferred to soil in caged pots, F1 plants were infested with neonate corn rootworm insects and grown for 13 days under controlled conditions. Root damage ratings (RDR) were determined using the Oleson, et al. rating scale of 0-3, where 0 means no injury and 3 means three or more nodes are pruned to within 1.5 inches of the stalk (J. D. Oleson, Y-L. Park, T. M. Nowatzki, J. J. Tollefson, "Node-Injury Scale to Evaluate Root Injury by Corn Rootworms", *Journal of Economic Entomology,* 98(1):1-8, 2005). Insect mortality was assessed by counting the number of third instar larvae remaining at the end of the growth period.

In a first set of experiments, plants expressing the full-length TIC3668, TIC3669, and TIC3670 proteins were tested against WCR. Some of the events showed a statistical significant reduction in node injury compared to the negative control with an average root damage rating (RDR) value between 2 and 2.5, but no commercially significant activity was observed for the full-length proteins.

Figure 3:
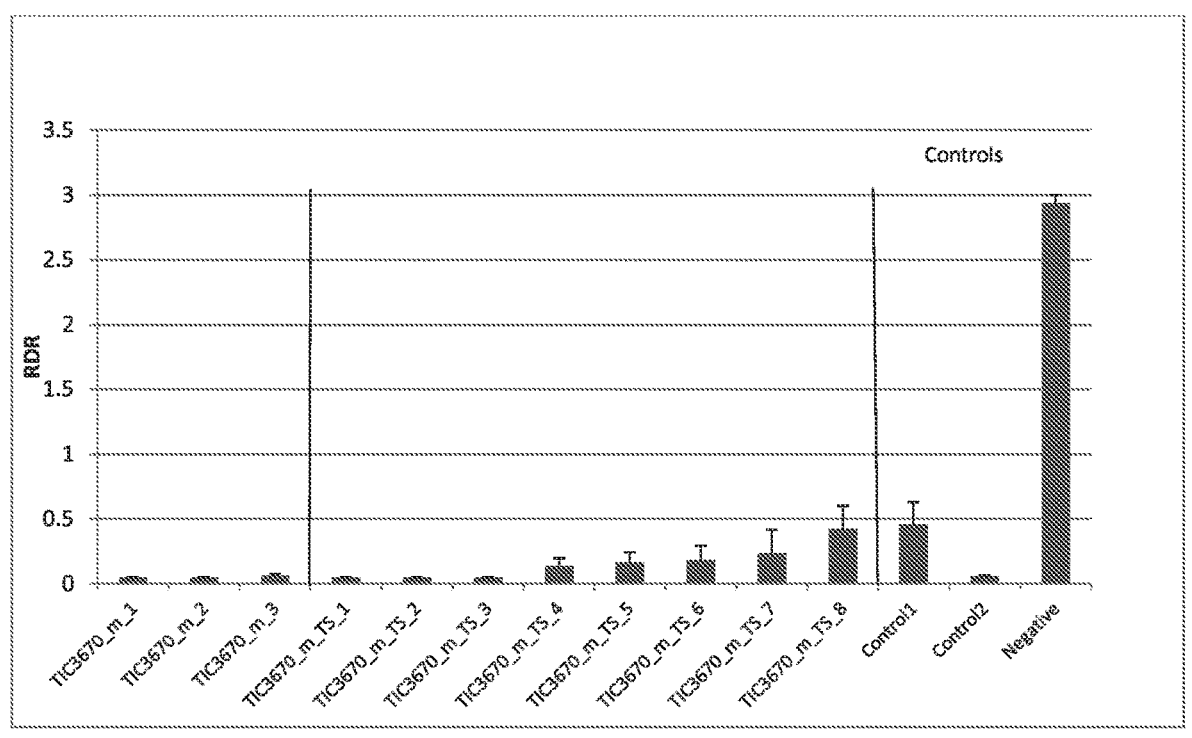
FIG. 3 illustrates in planta WCR inhibitory activity of an exemplary chloroplast targeted and non-targeted mature length TIC-3668-type protein.

In a second set of experiments, mature proteins mTIC3668 (SEQ ID NO:23), mTIC3669 (SEQ ID NO:24), and mTIC3670 (SEQ ID NO:25), with or without a chloroplast targeting peptide, were expressed in corn plants and tested against WCR. Significant WCR mortality was observed which each mature protein. Each plant expressing mTIC3668, mTIC3669, and mTIC3670, in the presence and absence of additional targeting sequences, showed a statistical significant reduction of node injury compared to the negative control. FIG. 2 depicts the average RDR values for several events for mTIC3668 and mTIC3669 proteins and FIG. 3 depicts the average RDR value for several events for mTIC3670 when expressed in F1 corn plants regardless of whether the protein was targeted to the chloroplast. "TS" in the event name of FIGS. 2 and 3 indicates the presence of a targeting sequence. Commercially significant activity was observed for many of these events expressing mature proteins mTIC3668, mTIC3669, and mTIC3670.

Surprisingly, removal of the membrane transiting segment (amino acids 1-23 as set forth in SEQ ID NO:2) from TIC3668-like proteins increased the efficacy against corn rootworm when expressed in corn plants. When expressed in plants, the mature length TIC3668-like proteins demonstrated higher levels of insecticidal activity against Coleopteran pests than the full-length proteins.

Example 8

Insecticidal Activity of TIC3668-Related Proteins, Expressed in Corn, Against Cry3Bb1 Resistant WCR This Example illustrates insecticidal activity exhibited by TIC3668-like proteins against a strain of Western Corn Rootworm (WCR) that has developed resistance to the Bt toxin Cry3Bb1. F1 transgenic corn plants expressing mTIC3668, mTIC3669 or mTIC3670, produced using methods as described in Example 7, were infested with 2000 WCR eggs of the Hopkinton strain per plant.

The Hopkinton strain of Western Corn Rootworm (*Diabrotica virgifera virgifera* LeConte) is a non-diapausing strain with field-evolved resistance to Cry3Bb1 expressed in corn plants. The strain originated from adult WCR samples obtained from fields that had been planted to Cry3Bb1 corn for seven consecutive years. The population was backcrossed with a non-diapausing WCR strain three times and selected for Cry3Bb1 resistance three times (Gassmann, et al. (2011) PLOS ONE 6(7): e22629; Gassmann, et al. (2012) GM Crops Food 3(3): 235-244). The colony was obtained from the laboratory of Dr. Aaron Gassman at Iowa State University, and is maintained by the Monsanto Biotech Entomology group in Chesterfield, MO.

Following infestation, the WCR-Hopkinton strain eggs hatched within 48 hours and the neonates began feeding on the roots. After 24 days, the roots were removed from the soil and corn root damage was evaluated as described in Example 7, using the 0-3 scale. As shown in Table 9, the plants expressing mTIC3668, mTIC3669 and mTIC3670 were highly effective at protecting corn roots from damage in the presence of Hopkinton strain WCR neonates compared to control plants, thus overcoming the WCR resistance to the Cry3Bb1 toxin.

TABLE 9

Average RDR in Transgenic Corn Plants Infested with Cry3Bb1 Resistant WCR

| Toxin | N | Average RDR (0-3) | Standard Error |
|---|---|---|---|
| mTIC3668 | 18 | 0.06 | 0.004 |
| mTIC3669 | 15 | 0.05 | 1.82e-10 |
| mTIC3670 | 14 | 0.05 | 1.95e-10 |
| Negative Control | 6 | 2.14 | 0.24 |

N: number of plants evaluated

Example 9

Insecticidal Activity of TIC3668-Related Proteins, Expressed in Corn, Against Natural Infestation of WCR in Field Test Sites This Example illustrates reduced root damage effectiveness exhibited by transgenic corn plants expressing TIC3668-like proteins against natural WCR infestations in Midwestern U.S. farm fields.

F1 transgenic corn plants expressing mTIC3668, mTIC3669 or mTIC3670, produced using methods as described in Example 7, were planted at five locations in Midwestern U.S. during late April to early May. Trials at these locations relied on existing natural infestations for corn rootworm pressure. Root digging, for damage assessment, was completed by the end of July. Rootworm damage was determined according to the node-injury scale, as described in Example 7.

Results from the root dig trials indicated that under practical conditions for farming in an open field, plants expressing mTIC3668, mTIC3669 and mTIC3670 were highly effective at protecting corn roots from damage in the presence of natural corn rootworm pressure. Table 10 shows the number of plants evaluated (N), the mean RDR and standard error for test plants when locations are combined.

TABLE 10

Mean RDR in Transgenic Corn Plants Tested in Farm Field with Natural WCR Infestation

| Toxin | N | Mean RDR (0-3) | Standard Error |
|---|---|---|---|
| mTIC3668 | 755 | 0.144 | 0.009 |
| mTIC3669 | 1108 | 0.159 | 0.008 |
| mTIC3670 | 1311 | 0.120 | 0.007 |
| Negative Control | 362 | 1.426 | 0.047 |

Example 10

Lepidopteran Activity of TIC3668-Related Protein Toxin Class

This Example illustrates inhibitory activity exhibited by TIC3668-like proteins against Lepidoptera. Protein preparations, as described in Example 1, for the full-length proteins of TIC3668, TIC3669 TIC3670, TIC4076, and TIC4078 were submitted for insect diet-overlay bioassays against Black Cutworms (BCW, *Agrotis ipsilon*), Western Bean Cutworm (WBC, *Striacosta albicosta*), Corn Earworms (CEW, *Helicoverpa zea*), European Corn Borers (ECB, *Ostrinia nubilalis*), Sugarcane Borer (SCB, *Diatraea saccharalis*), Southwestern Corn Borer (SWC, *Diatraea grandiosella*), cabbage looper (CLW, *Trichoplusia ni*), soybean looper (SBL, *Chrysodeixis includes*), and Fall Armyworm (FAW, *Spodoptera frugiperda*). Protocols and methods of preparing and performing inhibitory protein bioassays are known in the art.

Activity against certain Lepidopteran insect pests was observed for certain TIC3668-type proteins as demonstrated in Table 11.

TABLE 11

Observed Stunting against Lepidopteran Insect Pests of Exemplary Proteins.

| Toxin | ECB | SWC | BCW | FAW | CEW | SBL |
|---|---|---|---|---|---|---|
| TIC3668 | ++ | + | NT | – | – | – |
| TIC3669 | + | + | NT | – | – | – |
| TIC3670 | ++ | ++ | NT | – | – | + |
| TIC4076 | – | +++ | – | – | – | + |
| TIC4346 | + | + | NT | + | + | + |
| TIC4078 | NT | NT | NT | – | – | + |
| TIC4260, TIC4826 TIC4861, | NT | NT | NT | NT | NT | NT |

+ = Stunting observed
++ = Stunting and mortality
– = Mortality not observed
NT = Not tested Example 11

Lepidopteran Activity of TIC3668-Type Proteins in Plants

This example illustrates the inhibitory activity of the TIC3668-type proteins to ECB, SWC, BCW, FAW, CEW, SBL when expressed in plants and provided as a diet to respective insect pest.

Bioassays against Lepidopteran pests using plant leaf disks were performed similarly as described in U.S. Pat. No. 8,344,207 on TIC3668, TIC3669, and TIC3670 expressing R0 corn plants. The leaf damage rating (LDR) was assigned a rating score based upon the percent of the leaf disc devoured by the insect on a scale from 0 (0% eaten) to 11 (greater than 50%) eaten. Rating score steps increase incrementally by 5%. R0 plants which do not contain insecticidal proteins served as negative controls. The cytosolic expression of the full-length TIC3668-type protein reduced feeding damage against CEW, FAW and SWC relative to the untransformed control. Cytosolic expression of the TIC3670 protein reduced feeding damage against SWC relative to the untransformed control.

Example 12

Creation of the Collage Protein TIC4260

This Example teaches the creation of a novel gene sequence based on the family members of TIC3668. The amino acid variation from five of the native TIC3668-type proteins was combined to create a novel collage protein, TIC4260 (SEQ ID NO:12), that exhibits a different amino acid sequence diversity compared to the naturally occurring proteins. FIG. 1 depicts the alignment of five native TIC3668-type proteins with TIC4260. Positions of sequence diversity are highlighted in gray shading in this sequence alignment. An artificial polynucleotide sequence was constructed (SEQ ID NO:11) that encodes the TIC4260 protein. The mature TIC4260 protein (mTIC4260, SEQ ID NO:28) is encoded by the polynucleotide sequence as set forth in SEQ ID NO:43.

Similar alignments of other TIC3668-type proteins can be made in order to create novel proteins exhibiting Lepidoptera and/or Coleoptera toxic activity. These novel proteins are expressed, purified and tested against Lepidopteran and Coleopteran inspects in diet bioassays. Expression cassettes for these novel proteins are created and transformed into plants to express these proteins to control Lepidopteran and Coleopteran pests of plants.

Example 13

Assay of Activity of Full-Length and Mature TIC3668-Type Proteins

This Example illustrates the bioactivity of additional TIC3668-type toxin proteins, TIC11239, TIC11243, TIC11256, TIC4544, TIC4545, TIC6871, TIC7429, TIC7497, TIC7511, TIC7513, TIC7518, TIC7524, TIC7526, TIC7528, and TIC7535 against at least one corn rootworm species. Known members of corn rootworm species are *Diabrotica virgifera virgifera* (Western Corn Rootworm, WCR), *Diabrotica barberi* (Northern Corn Rootworm, NCR), *Diabrotica virgifera zeae* (Mexican Corn Rootworm, MCR), *Diabrotica balteata* (Brazilian Corn Rootworm (BZR), *Diabrotica* undecimpunctata howardii (Southern Corn Rootworm, SCR) and a Brazilian Corn Rootworm complex (BCR) consisting of *Diabrotica viridula* and *Diabrotica speciosa*).

Coding sequences encoding full length and mature forms of TIC11239, TIC11243, TIC11256, TIC4544, TIC4545, TIC6871, TIC7429, TIC7497, TIC7511, TIC7513, TIC7518, TIC7524, TIC7526, TIC7528, and TIC7535 were expressed in *Bacillus thuringiensis* (Bt) and *Escherichia coli* (*E. coli*) and used in a diet bioassay against at least one corn rootworm species. The full length toxins TIC11239, TIC11243, TIC11256, TIC4544, TIC4545, TIC6871, TIC7429, TIC7497, TIC7511, TIC7513, TIC7518, TIC7524, TIC7526, TIC7528, and TIC7535 were expressed in Bt, while the mature toxins, mTIC11239, mTIC11243, mTIC11256, mTIC4544, mTIC4545, mTIC6871, mTIC7429, mTIC7497, mTIC7511, mTIC7513, mTIC7518, mTIC7524, mTIC7526, mTIC7528, and mTIC7535 were expressed in *E. coli*. Preparations of each toxin protein were added to an insect diet and presented to corn rootworm neonates. Mortality and stunting were evaluated by comparing the growth and development of the neonates on the diet and compared to untreated controls fed a diet lacking toxin. The bioactivity for each full length and mature protein is provided in Table 12 below, wherein "+" indicates activity (mortality and growth inhibition), "NA" indicates no activity was observed for the sample, and "NT" indicates not tested.

TABLE 12

Activity of TIC3668-type proteins against corn rootworm species.

| Full Length Toxin | | | Mature Toxin | | |
| --- | --- | --- | --- | --- | --- |
| Toxin | Protein SEQ ID NO: | Corn Rootworm | Toxin | Protein SEQ ID NO: | Corn Rootworm |
| TIC11239 | 74 | + | mTIC11239 | 104 | + |
| TIC11243 | 76 | NA | mTIC11243 | 106 | + |
| TIC11256 | 78 | + | mTIC11256 | 108 | + |
| TIC4544 | 80 | + | mTIC4544 | 110 | NT |
| TIC4545 | 82 | + | mTIC4545 | 112 | NT |
| TIC6871 | 84 | + | mTIC6871 | 114 | NT |
| TIC7429 | 86 | + | mTIC7429 | 116 | NT |
| TIC7497 | 88 | + | mTIC7497 | 118 | + |
| TIC7511 | 90 | + | mTIC7511 | 120 | + |
| TIC7513 | 92 | + | mTIC7513 | 122 | NT |
| TIC7518 | 94 | + | mTIC7518 | 124 | NT |
| TIC7524 | 96 | NA | mTIC7524 | 126 | + |
| TIC7526 | 98 | + | mTIC7526 | 128 | + |
| TIC7528 | 100 | + | mTIC7528 | 130 | + |
| TIC7535 | 102 | NA | mTIC7535 | 132 | + |

As can be seen in Table 12, the full length toxins, TIC11239, TIC11256, TIC4544, TIC4545, TIC6871, TIC7429, TIC7497, TIC7511, TIC7513, TIC7518, TIC7526, and TIC7528 demonstrated activity against at least one corn rootworm species when expressed in Bt. The mature toxins, mTIC11239, mTIC11243, mTIC11256, mTIC7497, mTIC7511, mTIC7524, mTIC7526, mTIC7528, and mTIC7535 also demonstrated activity against at least one corn rootworm species.

All of the compositions and methods disclosed and claimed herein can be made and executed without undue experimentation in light of the present disclosure. While the compositions and methods of this invention have been described in terms of the foregoing illustrative embodiments, it will be apparent to those of skill in the art that variations, changes, modifications, and alterations may be applied to the composition, methods, and in the steps or in the sequence of steps of the methods described herein, without departing from the true concept, spirit, and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

It should be apparent to those skilled in the art that these different, improved sequence variations can be combined to create variants which are also within the scope of this invention.

5

All publications and published patent documents cited in the specification are incorporated herein by reference to the same extent as if each individual publication or patent application was specifically and individually indicated to be incorporated by reference.

What is claimed is:

1. A recombinant polynucleotide molecule encoding an insect inhibitory polypeptide comprising:

(a) the amino acid sequence of SEQ ID NO:78 or SEQ ID NO:108; or (b) an amino acid sequence having at least 98% identity to the amino acid sequence of SEQ ID NO:78 or SEQ ID NO:108, and wherein the recombinant polynucleotide molecule is operably linked to a heterologous promoter.

2. The recombinant polynucleotide molecule of claim 1 comprising:

(a) the nucleotide sequence of SEQ ID NO:77 or SEQ ID NO:107; or (b) a nucleotide sequence having at least 98% identity to the nucleotide sequence of SEQ ID NO: 77 or SEQ ID NO:107.

3. An insect inhibitory recombinant polypeptide encoded by the recombinant polynucleotide molecule of claim 1.

4. The insect inhibitory recombinant polypeptide of claim 3, wherein said insect inhibitory recombinant polypeptide comprises an amino acid sequence having at least 99% identity to the amino acid sequence of SEQ ID NO: 78 or SEQ ID NO: 108.

5. The insect inhibitory recombinant polypeptide of claim 3, wherein said insect inhibitory recombinant polypeptide exhibits inhibitory activity against Western Corn Rootworm, Southern Corn Rootworm, Northern Corn Rootworm, Mexican Corn Rootworm, Brazilian Corn Rootworm, or Brazilian Corn Rootworm complex consisting of *Diabrotica viridula* and *Diabrotica speciosa*.

6. The insect inhibitory recombinant polypeptide according to claim 5, wherein said insect inhibitory recombinant polypeptide exhibits inhibitory activity against Western Corn Rootworm.

7. A host cell comprising the recombinant polynucleotide molecule of claim 1, wherein said host cell is selected from the group consisting of a bacterial host cell and a plant host cell.

8. An insect inhibitory composition comprising the recombinant polynucleotide molecule of claim 1.

9. The insect inhibitory composition of claim 8, further comprising a nucleotide sequence encoding at least one other pesticidal agent that is different from said insect inhibitory polypeptide.

10. The insect inhibitory composition of claim 9, wherein said at least one other pesticidal agent is selected from the group consisting of an insect inhibitory protein, an insect inhibitory dsRNA molecule, and an ancillary protein.

11. The insect inhibitory composition of claim 10, wherein said at least one other pesticidal agent exhibits activity against one or more pest species of the orders Lepidoptera, Coleoptera, or Hemiptera.

12. The insect inhibitory composition of claim 11, wherein said at least one other pesticidal agent is selected from the group consisting of a Cry1A, Cry1Ab, Cry1Ac, Cry1A.105, Cry1B, Cry1C, Cry1D, Cry1E, Cry1F, Cry1G, Cry1H, Cry1I, Cry1J, Cry1K, Cry1L, Cry2A, Cry2Ab, Cry3A, Cry3B, Cry4B, Cry6, Cry7, Cry8, Cry9, Cry15, Cry34, Cry35, Cry43A, Cry43B, Cry51Aa1, ET29, ET33, ET34, ET35, ET66, ET70, TIC400, TIC407, TIC417, TIC431, TIC800, TIC807, TIC834, TIC853, TIC900, TIC901, TIC1201, TIC1415, VIP3A, and VIP3B protein.

13. An insect inhibitory composition comprising the insect inhibitory recombinant polypeptide of claim 3 in an insect inhibitory effective amount.

14. A method of controlling a corn rootworm pest, said method comprising contacting said pest with an insect inhibitory amount of the insect inhibitory recombinant polypeptide of claim 3.

15. A seed comprising the recombinant polynucleotide molecule of claim 1.

16. A commodity product comprising the host cell of claim 7, said commodity product comprising a detectable amount of said recombinant polynucleotide or an insect inhibitory recombinant polypeptide encoded by said recombinant polynucleotide.

17. A method of producing seed comprising the recombinant polynucleotide molecule of claim 1, said method comprising:

(a) planting at least one seed comprising said recombinant polynucleotide molecule;

(b) growing plants from said seed; and (c) harvesting seed from said plants, wherein said harvested seed comprises said recombinant polynucleotide molecule.

18. A recombinant vector comprising the recombinant polynucleotide molecule of claim 1.

19. The recombinant vector of claim 18, wherein said vector is selected from the group consisting of a plasmid, a bacmid, a phagemid, and a cosmid.

20. A plant resistant to insect infestation, wherein the cells of said plant comprise the recombinant polynucleotide molecule of claim 1.

* * * * *